United States Patent

Maywald et al.

Patent Number: 5,399,544
Date of Patent: Mar. 21, 1995

[54] ISOXAZOLE- AND ISOTHIAZOLE-5-CARBOXAMIDES

[75] Inventors: Volker Maywald, Ludwigshafen; Peter Muenster, Neulussheim; Hartmann Koenig, Limburgerhof; Gerhard Hamprecht, Weinheim; Thomas Kuekenhoehner, Boehl-Iggelheim; Wolfgang Rohr, Wachenheim; Helmut Walter, Obrigheim; Karl-Otto Westphalen, Speyer; Matthias Gerber, Mutterstadt, all of Germany

[73] Assignee: BASF Aktiengesellschaft, Ludwigshafen, Germany

[21] Appl. No.: 117,102
[22] PCT Filed: Jan. 29, 1992
[86] PCT No.: PCT/EP92/00183
§ 371 Date: Sep. 14, 1993
§ 102(e) Date: Sep. 14, 1993
[87] PCT Pub. No.: WO92/16514
PCT Pub. Date: Oct. 1, 1992

[30] Foreign Application Priority Data

Mar. 14, 1991 [DE] Germany .................. 41 08 183.8

[51] Int. Cl.⁶ ............... C07D 261/18; C07D 275/02; A01N 43/80
[52] U.S. Cl. ................ 504/269; 504/271; 548/213; 548/214; 548/243; 548/248; 548/249
[58] Field of Search ............... 548/214, 243, 213, 248, 548/249; 504/269, 271

[56] References Cited

U.S. PATENT DOCUMENTS 5,201,932 4/1993 Maywald .................. 504/271
5,205,854 4/1993 Freund .................... 504/191

Primary Examiner—Robert Gerstl
Attorney, Agent, or Firm—Keil & Weinkauf

[57] ABSTRACT

Isoxazole- and isothiazole-5-carboxamides of the formula

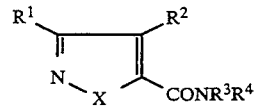

where X is oxygen or sulfur, $R^1$ is hydrogen, substituted or unsubstituted alkyl, cycloalkyl, cycloalkenyl, alkenyl (may be epoxidized at the double bond), alkynyl, alkoxy, a heterocyclic radical or phenyl, $R^2$ is a derivative carboxylic acid function and $R^3$ and $R^4$ have the meanings given in the disclosure, and herbicidal agents containing compounds I.

5 Claims, No Drawings

ISOXAZOLE- AND ISOTHIAZOLE-5-CARBOXAMIDES

The present invention relates to carboxamides of the formula I

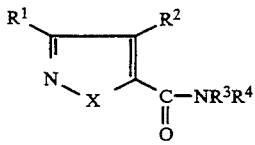

where
X is oxygen or sulfur;
$R^1$ is hydrogen, $C_1$–$C_6$-alkyl which can carry from one to five halogen atoms and/or one or two of the following:
$C_1$–$C_3$-alkoxy, $C_1$–$C_3$-haloalkoxy, cyano or phenyl which can be up to trisubstitued by halogen, $C_1$–$C_3$-alkyl, $C_1$–$C_3$-haloalkyl, $C_1$–$C_3$-alkoxy, $C_1$–$C_3$-haloalkoxy, cyano or nitro;
$C_3$–$C_8$-cycloalkyl-substituted $C_1$–$C_6$-alkyl;
$C_3$–$C_6$-cycloalkyl or $C_3$–$C_6$-cycloalkenyl, each of which can be mono- to trisubstituted by $C_1$–$C_4$-alkyl or halogen;
$C_2$–$C_6$-alkenyl whose double bond can be epoxidized, or $C_2$–$C_6$-alkynyl, where both groups can be mono- to trisubstitute by halogen, $C_1$–$C_3$-alkoxy and/or monosubstituted by cyclopropyl or phenyl, where the phenyl can additionally carry up to three of the following substituents:
$C_1$–$C_4$-alkyl, $C_1$–$C_4$-haloalkyl, $C_1$–$C_4$-alkoxy, $C_1$–$C_4$-haloalkoxy, halogen, cyano or nitro;
$C_1$–$C_4$-alkoxy;
a 5- or 6-membered heterocyclic radical with one or two hereto atoms selected from oxygen, sulfur and nitrogen, which can carry one or two of the following substituents:
$C_1$–$C_3$-alkyl, halogen, $C_1$–$C_3$-alkoxy, carboxyl or $C_1$–$C_3$-alkoxycarbonyl;
phenyl which can carry from one to three of the following:
$C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, $C_1$–$C_3$-haloalkylthio, halogen, nitro and cyano,
$R^2$ is haloformyl, $COYR^5$ or $CONR^6R^7$, where
Y is oxygen or sulfur
$R^5$ is $C_1$–$C_6$-alkyl which carries one of the following:
$C_5$–$C_6$-cycloalkaniminoxy, a 5- or 6-membered saturated or aromatic heterocyclic radical with from one to three hetero atoms selected from oxygen, sulfur and nitrogen, except unsubstituted thienyl, furyl, tetrahydrofuryl and pyridyl, it not being possible for two oxygen and/or sulfur atoms to be directly adjacent, and where the heterocycles can also carry one or two of the following substituents: halogen, $C_1$–$C_3$-alkyl, $C_1$–$C_3$-alkoxy or $C_1$–$C_3$-alkoxycarbonyl,
—$CR^{10}$=$N$—$R^{11}$ where
$R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyloxy, each of which can carry up to three halogen atoms and/or one phenyl with, if desired, up to three of the following: halogen, nitro, cyano, $C_1$–$C_3$-alkyl or $C_1$–$C_3$-alkoxy; phenoxy which can carry up to three of the following substituents:
halogen, nitro, cyano, $C_1$–$C_3$-alkyl or $C_1$–$C_3$-alkoxy;
$C_1$–$C_6$-alkylamino, di($C_1$–$C_6$-alkyl)amino or phenylamino, where the aromatic ring can carry up to three of the following halogen, nitro, cyano, $C_1$–$C_3$-alkyl or $C_1$–$C_3$-alkoxy;
$R^5$ is also a 5- or 6-membered saturated or aromatic heterocyclic radical with one or two hereto atoms selected from oxygen, sulfur or nitrogen, it not being possible for two oxygen and/or sulfur atoms to be directly adjacent, and where the heterocycles can carry one or two of the following substituents: halogen, $C_1$–$C_3$-alkyl, $C_1$–$C_3$-alkoxy or $C_1$–$C_3$-alkoxycarbonyl;
a 5- or 6-membered saturated-or aromatic heterocyclic radical with three hereto atoms selected from oxygen, sulfur or nitrogen, it not being possible for two oxygen and/or sulfur atoms to be directly adjacent, and where the heterocycles can carry one-or two of the following substituents: halogen, $C_1$–$C_3$-alkyl, $C_1$–$C_3$-alkoxy or $C_1$–$C_3$-alkoxycarbonyl;
$C_3$–$C_8$haloalkynyl;
—$N$=$CR^8R^9$ where $R^8$ is $C_1$–$C_3$-alkoxy, $C_1$–$C_4$-haloalkyl, $C_1$–$C_3$-alkoxy-$C_1$–$C_5$-alkyl or phenyl-$C_1$–$C_5$-alkyl, it being possible for the phenyl in turn to be mono- to trisubstituted by halogen, nitro, cyano, $C_1$–$C_3$-alkyl, $C_1$–$C_3$-haloalkyl, $C_1$–$C_3$-alkoxy or $C_1$–$C_3$-haloalkoxy and $R^9$ is $C_1$–$C_4$-alkyl;

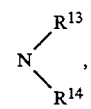

where
$R^3$ is hydrogen or $C_1$–$C_5$-alkyl and
$R^{14}$ is $C_1$–$C_5$-alkyl which can be substituted by $C_1$–$C_4$-alkanoyl or benzoyl which can be substituted by halogen or $C_1$–$C_3$-alkyl;
—W—Z where W is a $C_2$–$C_4$-alkylene chain, ethoxyethylene, 2-butenylene or 2-butynylene, and Z is a part of the molecule which is bonded in the ω position to W and which represents the same part of the molecule which is linked to W in the α position of W;
$R^6$ is hydrogen, $C_1$–$C_5$-alkyl or $C_3$–$C_8$-cycloalkyl and $R^7$ is —$C(OR^{12})$=NH or —$C(OR^{12})$=N—($C_1$–$C_4$)-alkyl, where $R^{12}$ is $C_1$–$C_4$-alkyl,
$R^3$ is hydrogen;
$C_1$–$C_6$-alkyl which can carry from one to three of the following substituents: hydroxyl, halogen, $C_1$–$C_4$-alkoxy, $C_1$–$C_4$-alkylthio or di-($C_1$–$C_4$)-alkylamino;
$C_3C_8$-cycloalkyl which can be mono- to trisubstituted by halogen, $C_1$–$C_4$-alkyl and partially or completely halogenated $C_1$–$C_4$-alkyl;
$R^4$ is hydrogen, hydroxyl, $C_1$–$C_4$-alkoxy;
$C_1$–$C_6$-alkyl which can carry from one to three of the following halogen, cyano, $C_1$–$C_4$-alkoxy, partially or completely halogenated $C_1$–$C_4$-alkoxy, $C_1$–$C_4$-alkylthio, partially or completely halogenated $C_1$–$C_4$-alkylthio, di-$C_1$–$C_4$-alkylamino, $C_3$–$C_8$-cycloalkyl or phenyl, where the phenyl ring in turn can carry one to three of the following halogen, cyano, nitro, $C_1$–$C_4$-alkyl, partially or completely halogenated $C_1$–$C_4$-alkyl, $C_1$–$C_4$-alkoxy, $C_1$–$C_4$-alkylthio or partially or completely halogenated $C_1$–$C_4$-alkoxy or $C_1$–$C_4$-alkylthio;
$C_3$–$C_8$-cycloalkyl which can carry from one to three of the following: halogen, nitro, cyano, $C_1$–$C_6$-alkyl, partially or completely halogenated $C_1$–$C_6$-alkyl, $C_1$–$C_4$- alkoxy or partially or completely halogenated $C_1$-$C_4$-alkoxy;

$C_3$-$C_6$-alkenyl whose double bond can be epoxidized, or $C_3$-$C_6$-alkynyl, each of which can be mono- to trisubstituted by halogen and/or monosubstituted by phenyl, where the phenyl in turn can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro;

di-($C_1$-$C_4$)-alkylamino;

a 5- or 6-membered heterocyclic, saturated or aromatic radical with one or two hereto atoms selected from oxygen, sulfur and nitrogen, which can be mono- to trisubstituted by $C_1$-$C_4$-alkyl or halogen;

phenyl which can carry from one to four of the followings $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro, cyano, formyl, $C_2$-$C_4$-alkanoyl, $C_2$-$C_4$-haloalkanoyl or $C_1$-$C_4$-alkoxycarbonyl;

naphthyl which can be mono- to trisubstituted by $C_1$-$C_4$alkyl or halogen; or $R^3$ and $R^4$ together form a tetra- to heptamethylene chain which can be interrupted by oxygen, sul fur or N-methyl, or —$(CH_2)_3$—CO—, with the proviso that $R^5$ is not $C_3$-$C_6$-haloalkynyl when $R^1$ is unsubstituted or substituted $C_2$-$C_6$-alkenyl, whose double bond can be epoxidized, unsubstituted or substituted $C_3$-$C_6$-cycloalkenyl, unsubstituted or substituted $C_2$-$C_6$-alkynyl or $C_3$-$C_8$-cycloalkyl-substituted $C_1$-$C_5$-alkyl;

and the environmentally acceptable salts of the compound I.

The present invention also relates to herbicidal agents which contain the compounds I as active ingredients and to the processes for preparing the compounds I.

Herbicidal isoxazole- and isothiazole-5-carboxamides and their derivatives are disclosed in DE-A-3,812,225. Despite the intrinsically good herbicidal activity of the known products, it is an object of the present invention to provide compounds with-improved properties, especially with regard to crop selectivity or environmental behavior.

We have found that this object is achieved by the isoxazole- and isothiazole-5-carboxamide defined in the introduction.

The carboxamides of the formula I according to the invention can be prepared in a variety of ways, preferably by the following processes:

1. Process for synthesizing the isoxazole- and isothiazole-5-carboxamides of the formula I, according to the invention, where $R^2$ is carboxyl starts from dialkyl isoxazole- and isothiazole-4,5-dicarboxylates of the formula II, with various substituents in position 3, respectively. The latter are initially hydrolyzed with one equivalent of an aqueous base to the monocarboxylic acids III which are then converted in a conventional manner into the halides IV or other activated forms of the carboxylic acid and subsequently amidated with an amine Va. The ester moiety in position 4 is then hydrolyzed in a conventional manner. This process has been described in detail in DE-A 38 12 225.

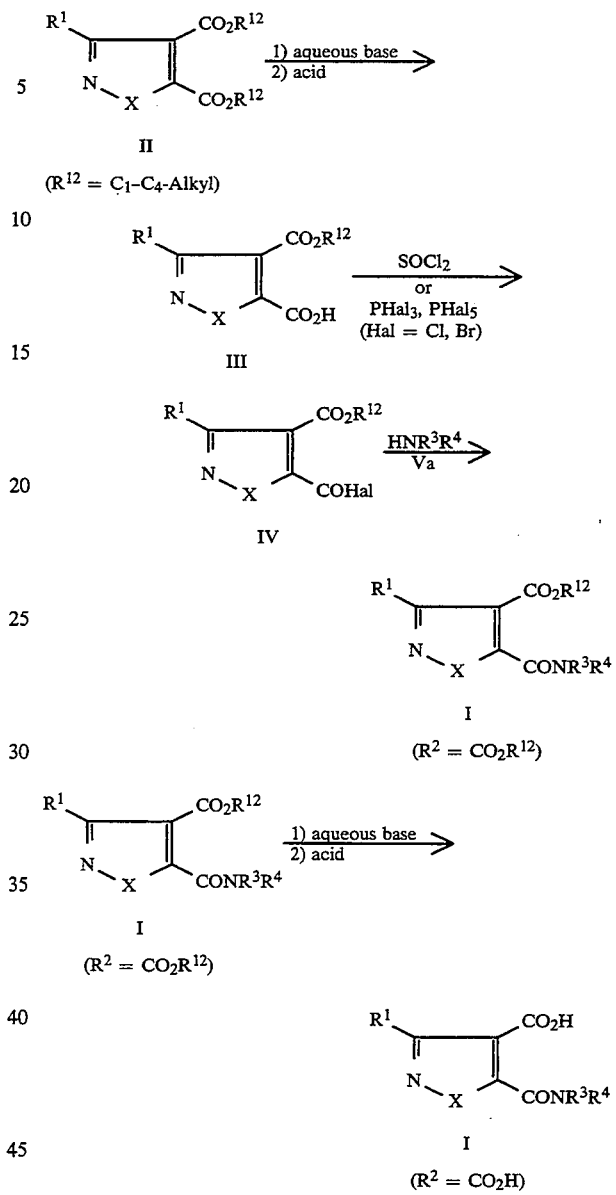

Esterification of the carboxylic acid (I with $R^2=CO_2H$) or halogenation in a conventional manner results in the corresponding acid derivative.

The dialkyl isoxazole- and isothiazole-4,5-dicarboxylates II required for this process are disclosed in the literature, and can be prepared by methods disclosed in the literature or can be obtained, for example, in the following ways:

a) a very widely applicable process for synthesizing dialkyl isoxazole-4,5-dicarboxylates of the formula II, with various substituents, where $R^1$ is, for example, hydrogen, unsubstituted or substituted alkyl, cycloalkyl, alkenyl, cycloalkenyl, alkynyl, phenyl or heterocyclyl, comprises reacting an appropriately substituted aldoxime of the formula VI in the presence of hypohalite with dialkyl acetylenedicarboxylate VII. In this reaction the aldoxime VI is oxidized by the hypohalite to the corresponding nitrile oxide. The nitrile oxide is a reactive 1,3-dipol which undergoes a cycloaddition with the dipolarophile present in the reaction medium, the dialkyl acetylene dicarboxylate VII.

It is expedient to react equimolar amounts of the aldoxime VI and the acetylenedicarboxylate VII with the hypohalite. The hypohalite can be added to the reaction mixture in stoichiometric amounts but it is usually mixed into the reaction mixture in a slight excess, up to two-fold. It may be advantageous for technical reasons to limit the conversion by using less than the stoichiometric amount of hypohalite, e.g. from 50 to 90 mol % hypohalite based on VI. It is likewise possible to use greater or less than the stoichiometric amounts of reactants VI or VII.

The hypohalites generally used are hypobromites and hypochlorites, preferably the latter. It is possible to employ for this purpose aqueous solutions of hypochlorous or hypobromous acid, but preferably alkali metal or alkaline earth metal hypochlorites or hypobromites are used, for example, sodium hypochlorite, potassium hypochlorite, calcium hypochlorite, magnesium hypochlorite, strontium hypochlorite, barium hypochlorite or the corresponding hypobromite. Sodium, potassium and calcium hypochlorite are particularly preferred, specifically in the form of their commercially available aqueous solutions.

Examples of suitable solvents for the process are alcohols such as methanol, ethanol, propanol or isopropanol, ketones such as acetone or methyl ethyl ketone, ethers such as diethyl ether, methyl tertbutyl ether, tetrahydrofuran or dioxane, hydrocarbons such as penfane, hexane, cyclohexane, petroleum ether, white oils or naphtha, aliphatic halohydrocarbons such as methylene chloride, chloroform, tetrachloromethane dichloroethane, trichloroethane, tetrachloroethane or perchloroethane, aromatic compounds such as benzene, toluene, xylenes or chlorobenzenes, esters such as-ethyl acetate, and dimethylformamide, N-methylpyrrolidone, dimethyl sulfoxide, sulfolane etc.

The reaction can be carried out at a wide range of temperatures. As a rule, the reaction takes place even at $-15°$ C. or below, and the upper temperature limit is determined in principle only by the boiling point of the solvent because the reaction is expediently carried out under atmospheric pressure. The reaction is preferably carried out at from 0 to 40° C. It can also be carried out under elevated pressure, especially under autogenous pressure, but a reaction under atmospheric pressure is preferred.

The aldoximes VI required for this process are known or can be prepared by known processes (e.g. Houben-Weyl, Methoden der organischen Chemie, Vol. 10/4, pages 55–56, Thieme Verlag, Stuttgart 1968) by reacting the appropriate aldehydes with hydroxylamine. The aldoximes VI can, of course, be used either in the form of their E or Z isomers or as a mixture thereof. The acetylenedicarboxylates are commercially available or can be prepared by conventional methods ( e.g. Organic Syntheses Coll. Vol. 4, page 329).

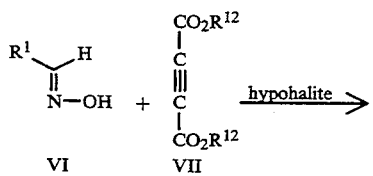

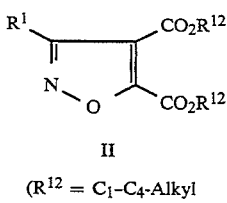

($R^{12} = C_1$–$C_4$-Alkyl)

b) Dialkyl isoxazole-4,5-dicarboxylates of the formula II where $R^1$ is hydroxymethyl and $R^2$ is $C_1$–$C_4$-alkyl are obtained by initially carrying out the cycloaddition, under the conditions described in a), of an aldoxime of the formula VI where $R^1$ is acetoxymethyl in the presence of sodium hypochlorite with dialkyl acetylenedicarboxylate VII ($R^{12}$=$C_1$–$C_4$-alkyl), and subsequently removing the acetoxy group by hydrolysis. The procedure for this is expediently such that from 1 to 2 times the molar amount of sodium methylate is added to the dialkyl acetoxy-methylisoxazole-4,5-dicarboxylate II (R=acetoxy-methyl) in methanol at about 20°–65° C.

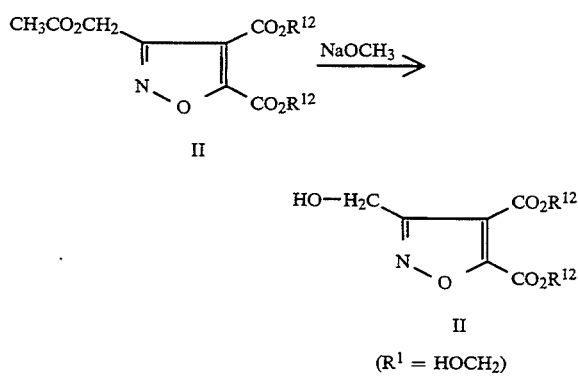

($R^1$ = $HOCH_2$)

Dialkyl 3-halomethylisoxazole-4,5-dicarboxylates can be obtained, for example, from the dialkyl 3-hydroxmethylisozazole-4,5-dicarboxylates II ($R^1$=HO—$CH_2$). The procedure for this is expediently such that an inorganic acid chloride is added dropwise to the dialkyl 3-hydroxymethylisoxazole-4,5-dicarboxylate in an inert solvent. The inorganic acid chloride can also act as solvent. The reaction is generally carried out at from 20° C. to the boiling point of the solvent. Suitable solvents are halohydrocarbons such as dichloromethane, chloroform, 1,2-dichloroethane and chlorobenzene, aromatic hydrocarbons such as benzene, toluene and xylene, and ethers such as tetrahydrofuran and dioxane.

Examples of inorganic acid chlorides which are used are thionyl chloride, phosphorus oxychloride, phosphorus trichloride, phosphorus pentachloride and phosphorus tribromide.

$C_1$–$C_3$-alkoxyalkyl, $C_1$–$C_3$-haloalkoxyalkyl- or cyanoalkyl-substituted dialkyl isoxazole-4,5-dicarboxylares can be obtained, for example, from the dialkyl 3-halomethylisoxazole-4,5-dicarboxylates by replacing the halide in a known manner by appropriate nucleophilic radicals.

2. Compounds of the formula I where $R^2$ is COHal are obtained, for example, by reacting a carboxylic acid of the formula I where $R^2$ is COOH in a conventional manner with an inorganic acid chloride such as thionyl chloride, phosphorus trihalide or phosphorus pentahalide. In this case it is expedient to employ from 1 to 5 mole equivalents, preferably 1 to 2 mole equivalents, of the inorganic acid halide. The reaction can be carried out without solvent or in the presence of an inert organic solvent such as benzene or toluene at from room temperature to the boiling point of the inorganic acid halide or of the inert organic solvent. In some cases it may be advantageous to add a catalyst Such as dimethylformamide or 4-dimethylaminopyridine. After the reaction is complete it is possible to isolate the acid halide in a conventional manner, e.g. by removing the excess inorganic acid chloride and the organic solvent by distillation.

3. Compounds of the formula I where $R^2$ is $COYR^5$ or $CONR^6R^7$ are obtained, for example by reacting a carboxylic acid I ($R^2$=COOH) with an alcohol or thiol VIII or with an amine Vb in the presence of a condensing agent, e.g. propanephosphonic anhydride (PPA) or dicyclohexylcarbodiimide (DCC) at from −20 to 70° C., preferably from 0 to 60° C.. The precursors are advantageously reacted in approximately the stoichiometric amount, preferably in the presence of an inert solvent such as tetrahydrofuran, dichloromethane, toluene or ethyl-acetate.

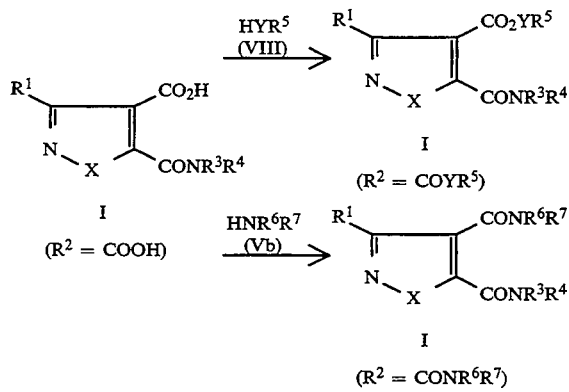

4. Another process for preparing compounds of the formula I where $R^2$ is $COYR^5$ or $CONR^6R^7$ is based on reacting an acid halide of the formula I ($Ra^2$=COHal) in a conventional manner with an alcohol or thiol VIII or an amine of the formula Vb. The procedure for this is expediently such that the halide I in an inert organic solvent is treated dropwise with a base, and then the alcohol or the thiol VIII or the amine Vb, preferably likewise dissolved in an inert organic solvent, is added dropwise. The reaction is generally complete after from 1 to 12 hours. The mixture can be worked up in a conventional manner, for example by hydrolysis with water and extraction of the final product with an organic solvent.

Suitable solvents are ethers such as diethyl ether, methyl tert-butyl ether, tetrahydrofuran and dioxane, halohydrocarbons such as dichloromethane, chloroform, 1,2-dichloroethane and chlorobenzene, or aromatic compounds such as benzene, toluene and xylene.

The reaction can be carried out at from −10 to 50° C., preferably 0 to 30° C.

It is preferable to use as-base tertiary amines such as pyridine, N,N-dimethylaniline or triethylamine.

The amines Vb required for processes 3 and 4 are known or can be prepared by known processes. The alcohols and thiols VIII are known in some cases. If $R^5$ is $C_1$-$C_6$-alkyl substituted by $-CR^{10}$=N-$R^{11}$, these alcohols and thiols can be prepared by one of the following known processes (shown by way of example for Y=O and $R^5$=-$CH_2CH$=$NOC_2H_5$):

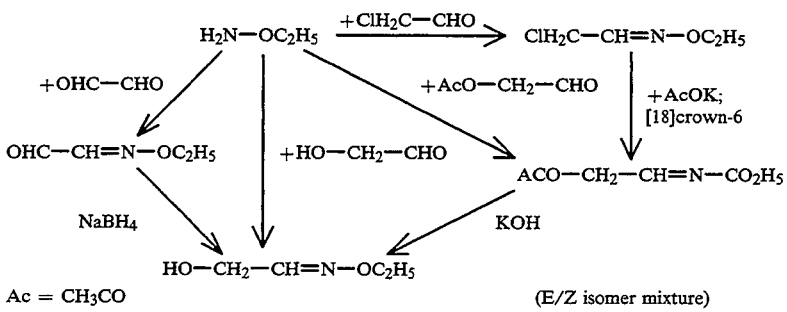

The following alcohols, for example, have been prepared by the said processes:
HO—$CH_2$—CH=N—$OCH_3$, HO—$CH_2$—C($CH_3$)=N—$OCH_3$, HO—$CH_2$—CH=N—$OCH_2$—CH=CHCl, HO—$CH_2$—CH=N—$OCH_2$—$C_6H_5$, HO—$CH_2$—C($CH_3$)=N—$OC_2H_5$, HO—$CH_2$—CH=N—$OCH_2$—CH=$CH_2$, HO—$CH_2$—C($CH_3$)=N—$OCH_2$—$C_6H_5$, HO—$CH_2$—C($CH_3$)=N—$OCH_2CH$=$CH_2$.

5. A process according to the invention for preparing compounds of the formula I where $R^5$ is $C_1$-$C_6$-alkyl which is substituted by —$CR^{10}$=N—$R^{11}$ comprises converting an isoxazole- or isothiazole-4-carboxylic acid of the formula I in an aprotic polar organic solvent with a base into the salt and then reacting the latter with about one equivalent of a substituted alkyl chloride IX (where A=$C_1$-$C_6$-alkyl). The reaction is generally complete after from 4 to 20 hours, and working up can be carried out in a Conventional manner by addition of water and extraction of the product-with an organic solvent. The reaction can be carried out at from 0 to 100° C., preferably from 20 to 60° C. A particularly suitable solvent is dimethyl sulfoxide.

The bases which are used are carbonates and alcoholates of alkali metals or alkaline earth metals, especially potassium carbonate and potassium tert-butylate.

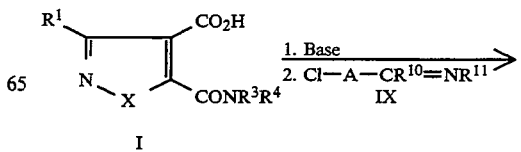

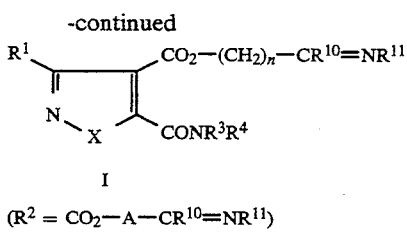

$(R^2 = CO_2-A-CR^{10}=NR^{11})$

6. Compounds of the formula I where $R^2$ is $COOR^5$ where $R^5$ is a cation such as an alkali metal, alkaline earth metal or ammonium ion are obtained by reacting a substituted isoxazole- or isothiazole-4-carboxylic acid I with one equivalent of the cation. If this is an inorganic cation such as sodium, potassium or calcium, it is expedient to dissolve or suspend the acid I in water or a lower alcohol and add one equivalent of the cation. The cation can be employed, for example, in the form of its hydroxide, carbonate or bicarbonate, preferably in the form of its hydroxide. The reaction is generally complete after a few minutes, and working up can be carried out in a conventional manner, for example by precipitation and filtration with suction or by concentration of the solution. To prepare ammonium salts, the acid I is dissolved or suspended in an organic solvent such as diethyl ether, tetrahydrofuran or dioxane and treated with one equivalent of ammonia, an amine or a tetraalkylammoniumhydroxide.

The following a mines-should be mentioned among those which can be employed: methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octodecylamine, methylethylamine, methylisopropylamine, methylhexylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanol-amine, N-ethylpropanolamine, N-butylethanolamine, allylamine, 2-butenylamine, 2-pentenylamine, 2,3-dimethyl-2-butenylamine, di-2 -butenylamine, 2 -hexenylamine, propylenediamine, tallow amine, cyclopentylamine, cyclohexylamine, dicyclohexylamine, piperidine, morpholine and pyrrolidine.

Examples of tetraalkylammonium hydroxides which can be employed are tetramethyl-, tetraethyl- or trimethylbenzylammonium hydroxide. As a rule, the salt of ammonia or organic amine precipitates from the solution and can be isolated by conventional methods. As an alternative, the salt can be obtained by concentration of the solution.

7. Compounds of the formula I where $R^1$ or $R^4$ is unsubstituted or substituted, epoxidized $C_2$-$C_5$-alkenyl are obtained, for example by epoxidation of carboxamides of the formula I where $R^1$ or $R^4$ is unsubstituted or substituted $C_2$-$C_5$-alkenyl in a conventional manner with suitable oxidizing agents (cf., for example, J. March, Advanced Organic Chemistry, Third Edition, John Wiley and Sons, 1985, p. 735).

Examples of the meanings of the substituents in the compounds I according to the invention are as follows:

X is oxygen or sulfur;

$R^1$ is hydrogen;

$C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, especially methyl, ethyl, propyl, 1-methylethyl, 1-methylpropyl and 1,1-dimethylethyl, it being possible for the alkyl to carry from one to five halogen atoms such as fluorine, chlorine, bromine and iodine, especially fluorine and chlorine and/or one or two of the following:

$C_1$-$C_3$-alkoxy such as methoxy-, ethoxy, propoxy and 1-methylethoxy, especially methoxy, ethoxy and 1-methylethoxy, $C_1$-$C_3$-haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy and pentafluoroethoxy, cyano or phenyl which can be up to trisubstituted by halogen as mentioned above, especially fluorine and chlorine, $C_1$-$C_3$-alkyl such as methyl, ethyl, propyl and 1-methylethyl, especially methyl and ethyl, $C_1$-$C_3$-haloalkyl such as difluoromethyl, trifluoromethyl, chlorodifluoromethyl, dichlorofluoromethyl, 1-fluoroethyl, 2-fluoroethyl, 2,2-difluoroethyl, 1,1,2,2-tetrafluoroethyl, 2,2,2-trifluoroethyl, 1-chloroethyl, 2-chloroethyl, 2,2,2-trichloroethyl, 2-chloro-1,1,2-trifluoroethyl and pentafluoroethyl, especially trifluoromethyl, $C_1$-$C_3$-alkoxy as mentioned above, especially methoxy and ethoxy, $C_1$-$C_3$-haloalkoxy as mentioned above, especially trifluoromethoxy, cyano or nitro;

$C_3$-$C_8$-cycloalkyl-substituted $C_1$-$C_6$-alkyl such as cyclopropylmethyl, 1-cyclopropylethyl, 2-cyclopropylethyl, 1-cyclopropyl-1-methylethyl, 2-cyclopropyl-1-methylethyl, cyclopentylmethyl, 1-cyclopentylethyl, 1-cyclopentylethyl, 1-cyclopentyl-1-methylethyl, cyclohexylmethyl, 1-cyclohexylethyl, 2-cyclohexylethyl, 1-cyclohexyl-1-methylethyl, especially cyclopropylmethyl, 1-cyclopropylethyl, 2-cyclopropylethyl, 1-cyclopropyl-1-methylethyl and 2-cyclopropyl-1-methylethyl, $C_3$-$C_8$-cycloalkyl such as cyclopropyl, cyclobutyl, cyclopentyl, cyclohexyl, cycloheptyl and cyclooctyl, especially cyclopropyl, cyclopentyl and cyclohexyl or $C_3$$C_6$-cycloalkenyl, especially 1-cyclopentenyt, 2-cyclopentenyl, 1-cyclohexenyl and 2-cyclohexenyl, each of which can be mono- to trisubstituted by $C_1$-$C_4$-alkyl as mentioned above, especially methyl, ethyl and 1-methylethyl, or halogen as mentioned above, especially fluorine and chlorine;

$C_2$-$C_5$-alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-ethyl-1-ethenyl, 1-pentenyl, 2-pentenyl, 3-pentenyl, 4-pentenyl, 1-methyl- 1-butenyl 2-methyl-1-butenyl, 3-methyl-2-butenyl, 1-methyl-2-butenyl, 2-methyl-2-butenyl, 2-methyl-2-butenyl, 1-methyl-3butenyl, 2-methyl-3-butenyl, 2-methyl-3-butenyl, 3-methyl-3-butenyl, 1-dimethyl-2-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2 -methyl- 1-pentenyl, 3-methyl- 1-pentenyl, 4-methyl- 1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, especially ethenyl, 1-propenyl, 2-propenyl, 1-methylethenyl, 1-butenyl, 2-butenyl, 3-butenyl, 1-methylpropenyl, 1-methyl-2-propenyl, 2-methyl-1-propenyl or 2-methyl-2-propenyl, whose double bond can be epoxidized, or $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-di-methyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, especially ethynyl, 1-propynyl and 2-propynyl, it being possible for both groups to be mono- to trisubstituted by halogen as mentioned above, especially fluorine, chlorine and iodine, $C_1$–$C_3$-alkoxy as mentioned above, especially methoxy and ethoxy and/or monosubstituted by cyclopropyl or phenyl, where the phenyl can additionally carry up to three of the following substituents $C_1$–$C_4$-alkyl as mentioned above, especially methyl and ethyl, $C_1$–$C_4$-alkoxy such as methoxy, ethoxy, propoxy, 1-methylethoxy, 1,1-dimethylethoxy, especially methoxy, $C_1$–$C_4$-haloalkoxy as mentioned above, especially trifluoromethoxy, halogen as mentioned above, especially fluorine and chlorine, cyano or nitro;

$C_1$–$C_4$-alkoxy, especially methoxy, ethoxy, propoxy, 1-methylethoxy, 1,1-dimethylethoxy;

a 5- or 6-membered heterocyclic radical with one or two hetero atoms selected from oxygen, sulfur and nitrogen such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazotyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, which can carry one or two of the following substituents $C_1$–$C_3$-alkyl as mentioned above, especially methyl, ethyl and 1-methylethyl, halogen as mentioned above, especially fluorine and chlorine, $C_1$–$C_3$-alkoxy as mentioned above, especially methoxyand ethoxy, carboxyl or $C_1$–$C_3$-alkoxycarbonyl such as methoxycarbonyl, ethoxycarbonyl and 1-methylethoxycarbonyl, especially methoxycarbonyl and ethoxycarbonyl;

phenyl which can carry from one to three of the following $C_1$–$C_3$-alkyl as mentioned above, especially methyl and ethyl, $C_1$-$C_3$-haloalkyl as mentioned above, especially trifluoromethyl, $C_1$–$C_3$-alkoxy as mentioned above, especially methoxy, $C_1$–$C_3$-haloalkoxy as mentioned above, especially trifluoromethoxy, $C_1$–$C_3$-alkylthio such as methylthio, ethylthio, propylthio, 1-methylethylthio, especially methylthio, $C_1$–$C_3$-haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2,2,2-trichloroethylthio and pentafluoroethylthio, especially trifluoromethylthio and pentafluoroethylthio, halogen as mentioned above, especially fluorine and chlorine, nitro and cyano, $R^2$ is fluoro-, chloro- or bromoformyl, $COYR^5$ or $CONR^6R^7$ where Y is oxygen or sulfur $R^5$ is $C_1$–$C_6$-alkyl, preferably $C_1$–$C_4$-alkyl such as methyl, ethyl, propyl, 1-methylethyl, butyl or 1,1-dimethylethyl, which caries one of the following: $C_5$–$C_6$-cycloalkaniminoxy such as cyclopentaniminoxy and cyclohexaniminoxy, a 5- or 6-membered saturated or aromatic heterocyclic radical with from one to three hetero atoms selected from oxygen, sulfur and nitrogen (except unsubstituted thienyl, furyl, tetrahydrofuryl and pyridyl), it not being possible for two oxygen and/or sulfur atoms to be directly adjacent, especially 2-tetrahydrofuranyl, 3-tetrahydrofuranyl, 2-tetrahydrothienyl, 3-tetrahydrothienyl, 2-tetrahydropyranyl, 3-tetrahydropyranyl, 4-etrahydropyranyl, 2-pyrrolidinyl, 3-pyrrolidinyl, 2-furanyl, 3-furanyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 2-oxazolyl, 30oxazolyl, 4-oxazolyl, 5-oxazolyl, 2-thiazolyl, 4-thizaolyl, 5-thiazolyl, 2-imidazolyl, 4-imidazolyl, 5-imidazolyl, 1-pyrazolyl, 3-pyrazolyl, 4-pyrazolyl, 5-pyrazolyl, 1,2,3-triazol- 1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,2,5-thiadiazol-4-yl, 1,3,4-thiadiazol-2-yl, 1,3,4-thiadiazol-5-yl, 1,2,3-oxadiazol-3-yl, 1,2,3-oxadiazol-5-yl, 1,2,4-oxadiazol-3-yl, 1,2,4-oxadiazol-5-yl, 1,2,5-oxadiazol-3-yl, 1,2,5-oxadiazol-4-yl, 1,3,4-oxadiazol-2-yl, 1,3,4-oxadiazol-2-yl, 2-pyridyl, 3-pyridyl, 4-pyridyl, 2-pyrimidyl, 4-pyrimidyl and 5-pyrimidyl, where the heterocycles can carry one or two of the following substituents: halogen such as fluorine, chlorine, bromine and iodine, especially fluorine and chlorine, $C_1$–$C_3$-alkyl, especially methyl, ethyl, propyl and 1-methylethyl, $C_1$–$C_3$- alkoxy, especially methoxy, ethoxy and 1-methylethoxy, or $C_1$–$C_3$-alkoxycarbonyl, especially methoxycarbonyl and ethoxycarbonyl;

—$CR^{10}$=N—$R^{11}$ where $R^{10}$ is hydrogen or branched or unbranched $C_1$–$C_5$-alkyl, especially $C_1$–$C_4$-alkyl such as methyl, ethyl, n-propyl, 1-methylethyl, n-butyl and 1,1-dimethylethyl, $R^{11}$ is $C_1$–$C_6$-alkoxy, $C_3$–$C_6$-alkenyloxy or $C_3$–$C_6$-alkynyloxy, especially $C_1$–$C_4$-alkoxy such as methoxy, ethoxy, n-propoxy, 1-methylethoxy, n-butoxy and 1,1-dimethy 1-ethoxy, and 2-propenyloxy, 2-butenyloxy, 2-propynyloxy an 2-butynyloxy, it being possible for these substituents to carry from one to three halogen atoms such as fluorine, chlorine, bromine and iodine, especially fluorine and chlorine, and/or one phenyl which is unsubstituted or mono- to trisubstituted by halogen as mentioned above, nitro, cyano, $C_1$–$C_3$-alkyl such as methyl, ethyl and n-propyl and/or $C_1$–$C_3$-alkoxy such as methoxy, ethoxy, n-propoxy and 1-methylethoxy; phenoxy which can carry from one to three of the following substituents:

nitro, cyano, halogen as mentioned above, $C_1$–$C_3$-alkyl as mentioned above and/or $C_1$–$C_3$-alkoxyl as mentioned above; branched or unbranched $C_1$–$C_6$-alkylamino, especially methylamino, ethylamino, di-($C_1$–$C_5$) -alkylamino, especially dimethylamino, methylethylamino or phenylamino, where the aromatic ring may be mono- to trisubstituted by nitro, cyano, halogen as mentioned above, $C_1$–$C_3$-alkyl as mentioned above and/or $C_1$–$C_3$-alkoxy as mentioned above;

$R^5$ is also a 5- or 6-membered saturated or aromatic heterocyclic radical with one or two hetero atoms selected from oxygen, sulfur and nitrogen, it not being possible for two oxygen and/or sulfur atoms to be directly adjacent, especially 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, where the heterocycles can carry one or two of the following substituents: halogen, especially fluorine and chlorine, $C_1$–$C_3$-alkyl, especially methyl, ethyl and 1-methylethyl, $C_1$–$C_3$-alkoxy, especially methoxy, ethoxy and 1-methylethoxy, or $C_1$–$C_3$-alkoxycarbonyl, especially methoxycarbonyl and ethoxycarbonyl;

a 5- or 6-membered saturated or aromatic heterocyclic radical with three hetero atoms selected from oxygen, sulfur and nitrogen, it not being possible for two oxygen and/or sulfur atoms to be directly adjacent, especially 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,2,5-thiadiazol-4-yl, 1,3,4-thiadiazol-2-yl, 1,3,4-thiadiazol-5-yl, 1,2,3-oxadiazol-3-yl, 1,2,3-oxadiazol-5-yl, 1,2,5-oxadiazol-3-yl, 1,2,5-oxadiazol-4-yl, 1,3,4-oxadiazol-2-yl, 1,3,4-oxadiazol-5-yl, where the heterocycles can carry one or two of the following substituents: halogen, especially fluorine and chlorine, $C_1$–$C_3$-alkyl, especially methyl, ethyl and 1-methylethyl, $C_1$–$C_3$-alkoxy, especially methoxy, ethoxy and 1-methylethoxy, or $C_1$–$C_3$-alkoxycarbonyl, especially methoxycarbonyl and ethoxycarbonyl;

$C_3$–$C_6$-haloalkynyl, especially $C_3$–$C_4$-haloalkynyl such as 1-methyl-3-iodo-2-propynyl and, preferably, 3-iodo-2-propynyl;

—N=$CR^8R^9$ where $R^8$ is $C_1$–$C_3$-alkoxy, especially methoxy, ethoxy and 1-methylethoxy, $C_1$–$C_4$-haloalkyl, especially fluoromethyl, difluoromethyl, trifluoromethyl, chlorodifluoromethyl, dichlorofluoromethyl, trichloromethyl, 1-fluoroethyl, 2-fluoroethyl, 1-chloroethyl, 2-chloroethyl, 2,2,2-trifluoroethyl, 2,2,2-trichloroethyl, $C_1$–$C_3$-alkoxy-$C_1$–$C_6$-alkyl, especially methoxymethyl, methoxyethyl, ethoxymethyl and ethoxyethyl or phenyl-$C_1$–$C_6$-alkyl, especially phenylmethyl, 1-phenylethyl and 2-phenylethyl, where the aromatic radical in turn can be mono- to trisubstituted by halogen, especially fluorine and chlorine, nitro, cyano, $C_1$–$C_3$-alkyl, especially methyl and ethyl, $C_1$–$C_3$-haloalkyl, especially trifluoromethyl, $C_1$–$C_3$-alkoxy, especially methoxyand ethoxy, or $C_1$–$C_3$-haloalkoxy, especially trifluoromethoxy, and $R^9$ is $C_1$–$C_4$-alkyl, especially methyl, ethyl and 1-methylethyl;

$NR^{13}R^{14}$ where $R^{13}$ is hydrogen or $C_1$–$C_6$-alkyl as mentioned above, especially methyl, ethyl, 1-methylethyl and 1,1-dimethylethyl and $R^{14}$ is $C_1$–$C_6$-alkyl as mentioned above, especially methyl, ethyl, 1-methylethyl and 1,1-dimethylethyl, which can be substituted by $C_1$–$C_4$-alkanoyl, especially formyl, acetyl and propionyl or benzoyl, which can be substituted by halogen, especially fluorine and chlorine, or $C_1$–$C_3$-alkyl, especially methyl;

—W—Z where

W is ethylene, n-propylene, n-butylene, ethoxyethylene, 2-butenylene or 2-butynylene, Z is a part of the molecule which is bonded in the position to W and which represents the same part of the molecule which is linked to W in the $\alpha$ position of W, for example

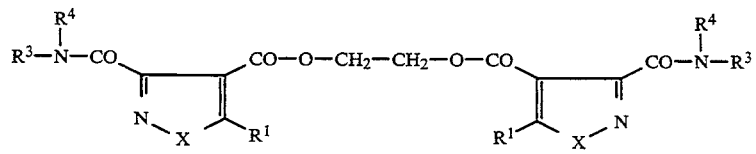

$R^6$ is hydrogen, $C_1$–$C_6$-alkyl, especially methyl, ethyl, 1-methylethyl and 1,1-dimethylethyl or $C_1$–$C_6$-cycloalkyl, especially cyclopropyl and cyclopentyl;

$R^7$ is —$C(OR^2)$=NH or —$C(OR^{12})$=N—($C_1$–$C_4$)-alkyl, where $C_1$–$C_4$-alkyl is as mentioned above, especially methyl, ethyl, 1-methylethyl and 1,1-dimethylethyl and $R^{12}$ is likewise $C_1$–$C_4$-alkyl as mentioned above, especially methyl and ethyl;

$R^3$ is hydrogen $C_1$–$C_6$-alkyl, preferably $C_1$–$C_4$-alkyl such as methyl, ethyl, 1-methylethyl and 1,1-dimethylethyl, which can carry from one to three of the following substituents hydroxyl, halogen, $C_1$–$C_4$-alkoxy such as methoxy and 1,1-dimethylethoxy, $C_1$–$C_4$-alkylthio such as methylthio and 1,1-dimethylethylthio or di-($C_1$–$C_4$)-alkylamino, preferably di-($C_1$–$C_2$)-alkylamino such as dimethylamino and diethylamino;

$C_3$–$C_8$-cycloalkyl, preferably-$C_3$–$C_6$cycloalkyl such as cyclopropyl, cyclopentyl and cyclohexyl, which can be mono- to trisubstituted by halogen such as fluorine, chlorine and bromine, $C_1$–$C_4$-alkyl such as methyl and 1,1-dimethylethyl or partially or completely halogenated $C_1$–$C_4$-alkyl such as fluoromethyl, trifluoromethyl, chlorodifluoromethyl, pentafluoroethyl and 2-chloro-1,1,2-trifluoroethyl;

$R^4$ is hydrogen, hydroxyl;

$C_1$–$C_4$-alkoxy such as methoxy, ethoxy, 1-methylethoxy, 1,1-dimethylethoxy; branched or unbranched $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, especially methyl, ethyl, propyl, 1-methylethyl and 1,1-dimethylethyl, which can carry from one to three of the following: halogen such as fluorine, chlorine and bromine, cyano, $C_1$–$C_4$-alkoxy such as methoxy, ethoxy and 1,1-dimethylethoxy, partially or completely halogenated $C_1$–$C_4$-alkoxy such as fluoromethoxy, trichloromethoxy, 2-chloro-1,1,2-trifluoroethoxy and pentafluoroethoxy, $C_1$–$C_4$-alkylthio such as methylthio, ethylthio and 1,1-dimethylethylthio, $C_1$–$C_4$-haloalkylthio such as fluoromethylthio, trichloromethylthio, 2-chloro-1,1,2-trifluoroethylthio and pentafluoroethylthio, di-($C_1$–$C_4$)alkylamino, especially di-($C_1$–$C_2$)-alkylamino such as dimethylamino and diethylamino, $C_3$–$C_8$-cycloalkyl, especially $C_3$–$C_6$-cycloalkyl such as cyclopropyl, cyclopentyl and cyclohexyl, or phenyl which in turn can carry up to three of the following: halogen such as fluorine, chlorine and bromine, cyano, nitro, $C_1$–$C_4$-alkyl such as methyl, ethyl and 1,1-dimethylethyl, $C_1$–$C_4$-haloalkyl such as fluoromethyl, trichloromethyl, 2-chloro-1,1,2-trifluoroethyl and pentafluoroethyl, $C_1$–$C_4$-alkoxy such as methoxy and 1,1-dimethylethoxy, partially or completely halogenated $C_1$–$C_4$-alkoxy such as fluoromethoxy, trichloromethoxy, 2-chloro-1,1,2-trifluoroethoxy and pentafluoroethoxy, $C_1$–$C_4$-alkylthio such as methylthio and 1,1-dimethylethylthio, or $C_1$–$C_4$-haloalkylthio such as fluoromethylthio, trichloromethylthio, 2-chloro-1,1,2-trifluoroethylthio and pentafluoroethylthio;

$C_3$–$C_8$-cycloalkyl, preferably $C_3$–$C_6$-cycloalkyl, especially cyclopropyl, cyclopentyl and cyclohexyl, each of which can carry from one to three of the following: halogen such as fluorine, chlorine and bromine, nitro, cyano, $C_1$–$C_6$-alkyl, preferably $C_1$–$C_4$-alkyl such as methyl, ethyl and 1,1-dimethylethyl, partially or completely halogenated $C_1$–$C_6$-alkyl, preferably $C_1$–$C_4$-haloalkyl such as fluoromethyl, trichloromethyl, 2-chloro-1,1,2-trifluoroethyl and pentafluoroethyl, $C_1$–$C_4$-alkoxy such as methoxy, 1,1-dimethylethoxy or partially or completely halogenated $C_1$–$C_4$-alkoxy such as fluoromethoxy, trichloromethoxy, 2-chloro-1,1,2-trifluoroethoxy and pentafluoroethoxy;

$C_3$–$C_5$-alkenyl, where the double bond can be epoxidized, or $C_3$–$C_6$-alkynyl, preferably $C_3$–$C_4$-alkenyl or $C_3$–$C_4$-alkynyl, such as 2-propenyl, 2-butenyl, 1,1-dimethyl-2-propenyl, 2-propynyl, 1,1-dimethyl-2-propynyl and 3-butynyl, each of which can be up to trisubstituted by halogen such as fluorine, chlorine or bromine and/or monosubstituted by phenyl which in turn can carry from one to three of the following substituents: halogen, especially fluorine and chlorine, cyano, nitro, $C_1$–$C_4$-alkyl such as methyl and 1,1-dimethylethyl, partially or completely halogenated $C_1$–$C_4$-alkyl such as fluoromethyl, trifluoromethyl, trichloromethyl, 2-chloro-1,1,2-trifluoroethyl and pentafluoroethyl, $C_1$–$C_4$-alkoxy such as methoxy and 1,1-dimethylethoxy, $C_1$–$C_4$-haloalkoxy such as fluoromethoxy, trifluoromethoxy, trichloromethoxy, 2-chloro-1,1,2-trifluoroethoxy and pentafluoroethoxy, $C_1$–$C_4$-alkylthio such as methylthio and 1,1-dimethylethylthio, partially or completely halogenated $C_1$–$C_4$-alkylthio such as fluoromethylthio, trifluoromethylthio, trichloromethylthio, 2-chloro-1,1,2-trifluoroethylthio and pentafluoroethylthio;

di ($C_1$–$C_4$) -alkylamino, preferably di-($C_1$–$C_2$)-alkylamino such as dimethylamino and diethylamino;

a 5- or 6-membered saturated or aromatic heterocyclic radical containing one or two hereto atoms selected from oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 3-pyridyl and 4-pyridyl, which can carry from one to three of the following substituents=$C_1$-C-alkyl as mentioned above, especially methyl, or halogen as mentioned above, especially fluorine and chlorine;

phenyl which can carry one to four of the following: $C_1$–$C_4$-alkyl as mentioned above, especially methyl, ethyl and 1-methylethyl; partially or completely halogenated $C_1$–$C_4$-alkyl as mentioned above, especially trifluoromethyl and chlorodifluoromethyl; $C_1$–$C_4$-alkoxy as mentioned above, especially methoxy and ethoxy; partially or completely halogenated $C_1$–$C_4$-alkoxy as mentioned above, especially trifluoromethoxy, trichloromethoxy and-pentafluoroethoxy; $C_1$–$C_4$-alkylthio as mentioned above, especially methylthio and ethylthio; partially or completely halogenated $C_1$–$C_4$-alkylthio as mentioned above, especially difluoromethylthio, trifluoromethylthio and pentafluoroethylthio, halogen as mentioned above, especially fluorine and chlorine, cyano, nitro, formyl, $C_1$–$C_4$-alkanoyl such as ethanoyl, propanoyl and 2-methylpropanoyl, especially ethanoyl, partially or completely halogenated $C_1$–$C_4$-alkanoyl such as trifluoroethanoyl, trichloroethanoyl, pentafluoropropanoyl, especially trifluoroethanoyl or $C_2$–$C_4$-alkoxycarbonyl such as methoxycarbonyl and ethoxycarbonyl;

naphthyl which can be mono- to trisubstituted by $C_1$-$C_4$-alkyl as mentioned above, especially methyl and ethyl, or halogen such as fluorine and chlorine;

$R^3$ and $R^4$ together are a $C_4$-$C_7$-methylene chain which can be interrupted by oxygen, sulfur or N-methyl, such as —(CH$_2$)$_3$—, —(CH$_2$)$_4$—, —(CH$_2$)$_5$—, —(CH$_2$)$_6$—, —CH$_2$—O—CH$_2$—, —CH$_2$—CH$_2$—O—CH$_2$—CH$_2$—, —CH$_2$—S—CH$_2$—, —CH$_2$—CH$_2$—S—CH$_2$—CH$_2$—, —CH$_2$—CH$_2$—N(CH$_3$)—CH$_2$—CH$_2$—, especially —(CH$_2$)$_5$— and —CH$_2$—CH$_2$—O—CH$_2$—CH$_2$—;

or —(CH$_2$)$_3$—CO—.

With a view to the intended use of the compounds I, the isoxazole- and isothiazole-5-carboxamides listed in the following table are of particular interest.

$$\underset{N\diagdown O}{R^1-}\!\!\overset{COOR^5}{\underset{CONHR^4}{=\!\!\!=}}\qquad I$$

| $R^1$ | $R^5$ | $R^4$ |
|---|---|---|
| H | CH$_2$—CH$_2$—O—N=⟨cyclobutylidene⟩ | 1,1-Dimethylethyl |
| Methyl | CH$_2$—CH$_2$—O—N=⟨cyclobutylidene⟩ | 1,1-Dimethylethyl |
| Ethyl | CH$_2$—CH$_2$—O—N=⟨cyclobutylidene⟩ | 1,1-Dimethylethyl |
| Propyl | CH$_2$—CH$_2$—O—N=⟨cyclobutylidene⟩ | 1,1-Dimethylethyl |
| 1-Methylethyl | CH$_2$—CH$_2$—O—N=⟨cyclobutylidene⟩ | 1,1-Dimethylethyl |
| 1-Methylpropyl | CH$_2$—CH$_2$—O—N=⟨cyclobutylidene⟩ | 1,1-Dimethylethyl |
| 1,1-Dimethylethyl | CH$_2$—CH$_2$—O—N=⟨cyclobutylidene⟩ | 1,1-Dimethylethyl |
| Cyclopropyl | CH$_2$—CH$_2$—O—N=⟨cyclobutylidene⟩ | 1,1-Dimethylethyl |
| Cyclopentyl | CH$_2$—CH$_2$—O—N=⟨cyclobutylidene⟩ | 1,1-Dimethylethyl |
| Cyclohexyl | CH$_2$—CH$_2$—O—N=⟨cyclobutylidene⟩ | 1,1-Dimethylethyl |
| 1-Methylcyclopropyl | CH$_2$—CH$_2$—O—N=⟨cyclobutylidene⟩ | 1,1-Dimethylethyl |
| Cyclopropylmethyl | CH$_2$—CH$_2$—O—N=⟨cyclobutylidene⟩ | 1,1-Dimethylethyl |
| 1-Cyclopropylethyl | CH$_2$—CH$_2$—O—N=⟨cyclobutylidene⟩ | 1,1-Dimethylethyl |
| Chloromethyl | CH$_2$—CH$_2$—O—N=⟨cyclobutylidene⟩ | 1,1-Dimethylethyl |
| 1-Chloroethyl | CH$_2$—CH$_2$—O—N=⟨cyclobutylidene⟩ | 1,1-Dimethylethyl |
| Methoxymethyl | CH$_2$—CH$_2$—O—N=⟨cyclobutylidene⟩ | 1,1-Dimethylethyl |

-continued

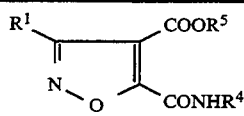

I

| R¹ | R⁵ | R⁴ |
|---|---|---|
| 1-Methylmethoxymethyl | CH₂—CH₂—O—N=⟨ | 1,1-Dimethylethyl |
| Ethenyl | CH₂—CH₂—O—N=⟨ | 1,1-Dimethylethyl |
| 1-Methylethenyl | CH₂—CH₂—O—N=⟨ | 1,1-Dimethylethyl |
| 1-Propenyl | CH₂—CH₂—O—N=⟨ | 1,1-Dimethylethyl |
| Methoxy | CH₂—CH₂—O—N=⟨ | 1,1-Dimethylethyl |
| Ethoxy | CH₂—CH₂—O—N=⟨ | 1,1-Dimethylethyl |
| 1,1-Dimethylethoxy | CH₂—CH₂—O—N=⟨ | 1,1-Dimethylethyl |
| Furanyl | CH₂—CH₂—O—N=⟨ | 1,1-Dimethylethyl |
| Thienyl | CH₂—CH₂—O—N=⟨ | 1,1-Dimethylethyl |
| 3-Methyl-isoxazol-5-yl | CH₂—CH₂—O—N=⟨ | 1,1-Dimethylethyl |
| 3-Ethyl-isoxazol-5-yl | CH₂—CH₂—O—N=⟨ | 1,1-Dimethylethyl |
| 3-(1-Methylethyl)-isoxazol-5-yl | CH₂—CH₂—O—N=⟨ | 1,1-Dimethylethyl |
| 5-Methyl-isoxazol-3-yl | CH₂—CH₂—O—N=⟨ | 1,1-Dimethylethyl |
| Phenyl | CH₂—CH₂—O—N=⟨ | 1,1-Dimethylethyl |
| 4-Fluorophenyl | CH₂—CH₂—O—N=⟨ | 1,1-Dimethylethyl |
| 4-Chlorophenyl | CH₂—CH₂—O—N=⟨ | 1,1-Dimethylethyl |
| 2,4-Dichlorophenyl | CH₂—CH₂—O—N=⟨ | 1,1-Dimethylethyl |
| H | CH₂—CH₂—O—N=⟨ | 1,1-Dimethyl-2-propynyl |
| Methyl | CH₂—CH₂—O—N=⟨ | 1,1-Dimethyl-2-propynyl |

-continued $$\underset{N\diagdown O}{\overset{R^1}{\diagup}}\underset{\diagdown CONHR^4}{\overset{COOR^5}{\diagup}} \qquad I$$

| R¹ | R⁵ | R⁴ |
|---|---|---|
| Ethyl | CH₂—CH₂—O—N=⟨ ⟩ | 1,1-Dimethyl-2-propynyl |
| Propyl | CH₂—CH₂—O—N=⟨ ⟩ | 1,1-Dimethyl-2-propynyl |
| 1-Methylethyl | CH₂—CH₂—O—N=⟨ ⟩ | 1,1-Dimethyl-2-propynyl |
| 1-Methylpropyl | CH₂—CH₂—O—N=⟨ ⟩ | 1,1-Dimethyl-2-propynyl |
| 1,1-Dimethylethyl | CH₂—CH₂—O—N=⟨ ⟩ | 1,1-Dimethyl-2-propynyl |
| Cyclopropyl | CH₂—CH₂—O—N=⟨ ⟩ | 1,1-Dimethyl-2-propynyl |
| Cyclopentyl | CH₂—CH₂—O—N=⟨ ⟩ | 1,1-Dimethyl-2-propynyl |
| Cyclohexyl | CH₂—CH₂—O—N=⟨ ⟩ | 1,1-Dimethyl-2-propynyl |
| 1-Methylcyclopropyl | CH₂—CH₂—O—N=⟨ ⟩ | 1,1-Dimethyl-2-propynyl |
| Cyclopropylmethyl | CH₂—CH₂—O—N=⟨ ⟩ | 1,1-Dimethyl-2-propynyl |
| 1-Cyclopropylethyl | CH₂—CH₂—O—N=⟨ ⟩ | 1,1-Dimethyl-2-propynyl |
| Chloromethyl | CH₂—CH₂—O—N=⟨ ⟩ | 1,1-Dimethyl-2-propynyl |
| 1-Chloroethyl | CH₂—CH₂—O—N=⟨ ⟩ | 1,1-Dimethyl-2-propynyl |
| Methoxymethyl | CH₂—CH₂—O—N=⟨ ⟩ | 1,1-Dimethyl-2-propynyl |
| 1-Methylmethoxymethyl | CH₂—CH₂—O—N=⟨ ⟩ | 1,1-Dimethyl-2-propynyl |
| Ethenyl | CH₂—CH₂—O—N=⟨ ⟩ | 1,1-Dimethyl-2-propynyl |
| 1-Methylethenyl | CH₂—CH₂—O—N=⟨ ⟩ | 1,1-Dimethyl-2-propynyl |
| 2-Propenyl | CH₂—CH₂—O—N=⟨ ⟩ | 1,1-Dimethyl-2-propynyl |

-continued $$\begin{array}{c} R^1 \diagdown \diagup COOR^5 \\ \| \\ N \diagdown_O \diagdown CONHR^4 \end{array} \qquad I$$

| R¹ | R⁵ | R⁴ |
|---|---|---|
| Methoxy | CH₂—CH₂—O—N=⬠ | 1,1-Dimethyl-2-propynyl |
| Ethoxy | CH₂—CH₂—O—N=⬠ | 1,1-Dimethyl-2-propynyl |
| 1,1-Dimethylethoxy | CH₂—CH₂—O—N=⬠ | 1,1-Dimethyl-2-propynyl |
| Furanyl | CH₂—CH₂—O—N=⬠ | 1,1-Dimethyl-2-propynyl |
| Thienyl | CH₂—CH₂—O—N=⬠ | 1,1-Dimethyl-2-propynyl |
| 3-Methyl-isoxazol-5-yl | CH₂—CH₂—O—N=⬠ | 1,1-Dimethyl-2-propynyl |
| 3-Ethyl-isoxazol-5-yl | CH₂—CH₂—O—N=⬠ | 1,1-Dimethyl-2-propynyl |
| 3-(1-Methylethyl)-isoxazol-5-yl | CH₂—CH₂—O—N=⬠ | 1,1-Dimethyl-2-propynyl |
| 5-Methyl-isoxazol-3-yl | CH₂—CH₂—O—N=⬠ | 1,1-Dimethyl-2-propynyl |
| Phenyl | CH₂—CH₂—O—N=⬠ | 1,1-Dimethyl-2-propynyl |
| 4-Fluorophenyl | CH₂—CH₂—O—N=⬠ | 1,1-Dimethyl-2-propynyl |
| 4-Chlorophenyl | CH₂—CH₂—O—N=⬠ | 1,1-Dimethyl-2-propynyl |
| 2,4-Dichlorophenyl | CH₂—CH₂—O—N=⬠ | 1,1-Dimethyl-2-propynyl |
| H | CH₂—CH₂—O—N=⬡ | 1,1-Dimethylethyl |
| Methyl | CH₂—CH₂—O—N=⬡ | 1,1-Dimethylethyl |
| Ethyl | CH₂—CH₂—O—N=⬡ | 1,1-Dimethylethyl |
| Propyl | CH₂—CH₂—O—N=⬡ | 1,1-Dimethylethyl |
| 1-Methylethyl | CH₂—CH₂—O—N=⬡ | 1,1-Dimethylethyl |
| 1-Methylpropyl | CH₂—CH₂—O—N=⬡ | 1,1-Dimethylethyl |

-continued

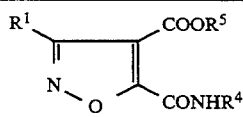

I

| R¹ | R⁵ | R⁴ |
|---|---|---|
| 1,1-Dimethylethyl | CH₂—CH₂—O—N=⌬ | 1,1-Dimethylethyl |
| Cyclopropyl | CH₂—CH₂—O—N=⌬ | 1,1-Dimethylethyl |
| Cyclopentyl | CH₂—CH₂—O—N=⌬ | 1,1-Dimethylethyl |
| Cyclohexyl | CH₂—CH₂—O—N=⌬ | 1,1-Dimethylethyl |
| 1-Methylcyclopropyl | CH₂—CH₂—O—N=⌬ | 1,1-Dimethylethyl |
| Cyclopropylmethyl | CH₂—CH₂—O—N=⌬ | 1,1-Dimethylethyl |
| 1-Cyclopropylethyl | CH₂—CH₂—O—N=⌬ | 1,1-Dimethylethyl |
| Chloromethyl | CH₂—CH₂—O—N=⌬ | 1,1-Dimethylethyl |
| 1-Chloroethyl | CH₂—CH₂—O—N=⌬ | 1,1-Dimethylethyl |
| Methoxymethyl | CH₂—CH₂—O—N=⌬ | 1,1-Dimethylethyl |
| 1-Methylmethoxymethyl | CH₂—CH₂—O—N=⌬ | 1,1-Dimethylethyl |
| Ethenyl | CH₂—CH₂—O—N=⌬ | 1,1-Dimethylethyl |
| 1-Methylethenyl | CH₂—CH₂—O—N=⌬ | 1,1-Dimethylethyl |
| 2-Propenyl | CH₂—CH₂—O—N=⌬ | 1,1-Dimethylethyl |
| Methoxy | CH₂—CH₂—O—N=⌬ | 1,1-Dimethylethyl |
| Ethoxy | CH₂—CH₂—O—N=⌬ | 1,1-Dimethylethyl |
| 1,1-Dimethylethoxy | CH₂—CH₂—O—N=⌬ | 1,1-Dimethylethyl |
| Furanyl | CH₂—CH₂—O—N=⌬ | 1,1-Dimethylethyl |

-continued

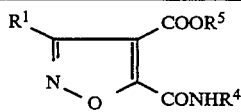

I

| R¹ | R⁵ | R⁴ |
|---|---|---|
| Thienyl | CH₂—CH₂—O—N=⟨⟩ | 1,1-Dimethylethyl |
| 3-Methyl-isoxazol-5-yl | CH₂—CH₂—O—N=⟨⟩ | 1,1-Dimethylethyl |
| 3-Ethyl-isoxazol-5-yl | CH₂—CH₂—O—N=⟨⟩ | 1,1-Dimethylethyl |
| 3-(1-Methylethyl)-isoxazol-5-yl | CH₂—CH₂—O—N=⟨⟩ | 1,1-Dimethylethyl |
| 5-Methyl-isoxazol-3-yl | CH₂—CH₂—O—N=⟨⟩ | 1,1-Dimethylethyl |
| Phenyl | CH₂—CH₂—O—N=⟨⟩ | 1,1-Dimethylethyl |
| 4-Fluorophenyl | CH₂—CH₂—O—N=⟨⟩ | 1,1-Dimethylethyl |
| 4-Chlorophenyl | CH₂—CH₂—O—N=⟨⟩ | 1,1-Dimethylethyl |
| 2,4-Dichlorophenyl | CH₂—CH₂—O—N=⟨⟩ | 1,1-Dimethylethyl |
| H | CH₂—CH₂—O—N=⟨⟩ | 1,1-Dimethyl-2-propynyl |
| Methyl | CH₂—CH₂—O—N=⟨⟩ | 1,1-Dimethyl-2-propynyl |
| Ethyl | CH₂—CH₂—O—N=⟨⟩ | 1,1-Dimethyl-2-propynyl |
| Propyl | CH₂—CH₂—O—N=⟨⟩ | 1,1-Dimethyl-2-propynyl |
| 1-Methylethyl | CH₂—CH₂—O—N=⟨⟩ | 1,1-Dimethyl-2-propynyl |
| 1-Methylpropyl | CH₂—CH₂—O—N=⟨⟩ | 1,1-Dimethyl-2-propynyl |
| 1,1-Dimethylethyl | CH₂—CH₂—O—N=⟨⟩ | 1,1-Dimethyl-2-propynyl |
| Cyclopropyl | CH₂—CH₂—O—N=⟨⟩ | 1,1-Dimethyl-2-propynyl |
| Cyclopentyl | CH₂—CH₂—O—N=⟨⟩ | 1,1-Dimethyl-2-propynyl |
| Cyclohexyl | CH₂—CH₂—O—N=⟨⟩ | 1,1-Dimethyl-2-propynyl |

-continued

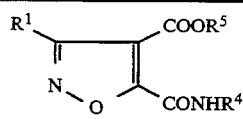
I

| R¹ | R⁵ | R⁴ |
|---|---|---|
| 1-Methylcyclopropyl | CH₂—CH₂—O—N=⟨cyclohexylidene⟩ | 1,1-Dimethyl-2-propynyl |
| Cyclopropylmethyl | CH₂—CH₂—O—N=⟨cyclohexylidene⟩ | 1,1-Dimethyl-2-propynyl |
| 1-Cyclopropylethyl | CH₂—CH₂—O—N=⟨cyclohexylidene⟩ | 1,1-Dimethyl-2-propynyl |
| Chloromethyl | CH₂—CH₂—O—N=⟨cyclohexylidene⟩ | 1,1-Dimethyl-2-propynyl |
| 1-Chloroethyl | CH₂—CH₂—O—N=⟨cyclohexylidene⟩ | 1,1-Dimethyl-2-propynyl |
| Methoxymethyl | CH₂—CH₂—O—N=⟨cyclohexylidene⟩ | 1,1-Dimethyl-2-propynyl |
| 1-Methylmethoxymethyl | CH₂—CH₂—O—N=⟨cyclohexylidene⟩ | 1,1-Dimethyl-2-propynyl |
| Ethenyl | CH₂—CH₂—O—N=⟨cyclohexylidene⟩ | 1,1-Dimethyl-2-propynyl |
| 1-Methylethenyl | CH₂—CH₂—O—N=⟨cyclohexylidene⟩ | 1,1-Dimethyl-2-propynyl |
| 2-Propenyl | CH₂—CH₂—O—N=⟨cyclohexylidene⟩ | 1,1-Dimethyl-2-propynyl |
| Methoxy | CH₂—CH₂—O—N=⟨cyclohexylidene⟩ | 1,1-Dimethyl-2-propynyl |
| Ethoxy | CH₂—CH₂—O—N=⟨cyclohexylidene⟩ | 1,1-Dimethyl-2-propynyl |
| 1,1-Dimethylethoxy | CH₂—CH₂—O—N=⟨cyclohexylidene⟩ | 1,1-Dimethyl-2-propynyl |
| Furanyl | CH₂—CH₂—O—N=⟨cyclohexylidene⟩ | 1,1-Dimethyl-2-propynyl |
| Thienyl | CH₂—CH₂—O—N=⟨cyclohexylidene⟩ | 1,1-Dimethyl-2-propynyl |
| 3-Methyl-isoxazol-5-yl | CH₂—CH₂—O—N=⟨cyclohexylidene⟩ | 1,1-Dimethyl-2-propynyl |
| 3-Ethyl-isoxazol-5-yl | CH₂—CH₂—O—N=⟨cyclohexylidene⟩ | 1,1-Dimethyl-2-propynyl |
| 3-(1-Methylethyl)-isoxazol-5-yl | CH₂—CH₂—O—N=⟨cyclohexylidene⟩ | 1,1-Dimethyl-2-propynyl |

-continued $$\underset{N\diagdown O}{\overset{R^1}{\diagup}}\genfrac{}{}{0pt}{}{COOR^5}{CONHR^4} \quad I$$

| R¹ | R⁵ | R⁴ |
|---|---|---|
| 5-Methyl-isoxazol-3-yl | CH₂—CH₂—O—N=⟨cyclohexyl⟩ | 1,1-Dimethyl-2-propynyl |
| Phenyl | CH₂—CH₂—O—N=⟨cyclohexyl⟩ | 1,1-Dimethyl-2-propynyl |
| 4-Fluorophenyl | CH₂—CH₂—O—N=⟨cyclohexyl⟩ | 1,1-Dimethyl-2-propynyl |
| 4-Chlorophenyl | CH₂—CH₂—O—N=⟨cyclohexyl⟩ | 1,1-Dimethyl-2-propynyl |
| 2,4-Dichlorophenyl | CH₂—CH₂—O—N=⟨cyclohexyl⟩ | 1,1-Dimethyl-2-propynyl |
| H | CH₂—CH=NOCH₃ | 1,1-Dimethylethyl |
| Methyl | CH₂—CH=NOCH₃ | 1,1-Dimethylethyl |
| Ethyl | CH₂—CH=NOCH₃ | 1,1-Dimethylethyl |
| Propyl | CH₂—CH=NOCH₃ | 1,1-Dimethylethyl |
| 1-Methylethyl | CH₂—CH=NOCH₃ | 1,1-Dimethylethyl |
| 1-Methylpropyl | CH₂—CH=NOCH₃ | 1,1-Dimethylethyl |
| 1,1-Dimethylethyl | CH₂—CH=NOCH₃ | 1,1-Dimethylethyl |
| Cyclopropyl | CH₂—CH=NOCH₃ | 1,1-Dimethylethyl |
| Cyclopentyl | CH₂—CH=NOCH₃ | 1,1-Dimethylethyl |
| Cyclohexyl | CH₂—CH=NOCH₃ | 1,1-Dimethylethyl |
| 1-Methylcyclopropyl | CH₂—CH=NOCH₃ | 1,1-Dimethylethyl |
| Cyclopropylmethyl | CH₂—CH=NOCH₃ | 1,1-Dimethylethyl |
| 1-Cyclopropylethyl | CH₂—CH=NOCH₃ | 1,1-Dimethylethyl |
| Chloromethyl | CH₂—CH=NOCH₃ | 1,1-Dimethylethyl |
| 1-Chloroethyl | CH₂—CH=NOCH₃ | 1,1-Dimethylethyl |
| Methoxymethyl | CH₂—CH=NOCH₃ | 1,1-Dimethylethyl |
| 1-Methylmethoxymethyl | CH₂—CH=NOCH₃ | 1,1-Dimethylethyl |
| Ethenyl | CH₂—CH=NOCH₃ | 1,1-Dimethylethyl |
| 1-Methylethenyl | CH₂—CH=NOCH₃ | 1,1-Dimethylethyl |
| 2-Propenyl | CH₂—CH=NOCH₃ | 1,1-Dimethylethyl |
| Methoxy | CH₂—CH=NOCH₃ | 1,1-Dimethylethyl |
| Ethoxy | CH₂—CH=NOCH₃ | 1,1-Dimethylethyl |
| 1,1-Dimethylethoxy | CH₂—CH=NOCH₃ | 1,1-Dimethylethyl |
| Furanyl | CH₂—CH=NOCH₃ | 1,1-Dimethylethyl |
| Thienyl | CH₂—CH=NOCH₃ | 1,1-Dimethylethyl |
| 3-Methyl-isoxazol-5-yl | CH₂—CH=NOCH₃ | 1,1-Dimethylethyl |
| 3-Ethyl-isoxazol-5-yl | CH₂—CH=NOCH₃ | 1,1-Dimethylethyl |
| 3-(1-Methylethyl)-isoxazol-5-yl | CH₂—CH=NOCH₃ | 1,1-Dimethylethyl |
| 5-Methyl-isoxazol-3-yl | CH₂—CH=NOCH₃ | 1,1-Dimethylethyl |
| Phenyl | CH₂—CH=NOCH₃ | 1,1-Dimethylethyl |
| 4-Fluorophenyl | CH₂—CH=NOCH₃ | 1,1-Dimethylethyl |
| 4-Chlorophenyl | CH₂—CH=NOCH₃ | 1,1-Dimethylethyl |
| 2,4-Dichlorophenyl | CH₂—CH=NOCH₃ | 1,1-Dimethylethyl |
| H | CH₂—CH=NOCH₃ | 1,1-Dimethyl-2-propynyl |
| Methyl | CH₂—CH=NOCH₃ | 1,1-Dimethyl-2-propynyl |
| Ethyl | CH₂—CH=NOCH₃ | 1,1-Dimethyl-2-propynyl |
| Propyl | CH₂—CH=NOCH₃ | 1,1-Dimethyl-2-propynyl |
| 1-Methylethyl | CH₂—CH=NOCH₃ | 1,1-Dimethyl-2-propynyl |
| 1-Methylpropyl | CH₂—CH=NOCH₃ | 1,1-Dimethyl-2-propynyl |
| 1,1-Dimethylethyl | CH₂—CH=NOCH₃ | 1,1-Dimethyl-2-propynyl |
| Cyclopropyl | CH₂—CH=NOCH₃ | 1,1-Dimethyl-2-propynyl |
| Cyclopentyl | CH₂—CH=NOCH₃ | 1,1-Dimethyl-2-propynyl |
| Cyclohexyl | CH₂—CH=NOCH₃ | 1,1-Dimethyl-2-propynyl |
| 1-Methylcyclopropyl | CH₂—CH=NOCH₃ | 1,1-Dimethyl-2-propynyl |
| Cyclopropylmethyl | CH₂—CH=NOCH₃ | 1,1-Dimethyl-2-propynyl |
| 1-Cyclopropylethyl | CH₂—CH=NOCH₃ | 1,1-Dimethyl-2-propynyl |
| Chloromethyl | CH₂—CH=NOCH₃ | 1,1-Dimethyl-2-propynyl |
| 1-Chloroethyl | CH₂—CH=NOCH₃ | 1,1-Dimethyl-2-propynyl |
| Methoxymethyl | CH₂—CH=NOCH₃ | 1,1-Dimethyl-2-propynyl |
| 1-Methylmethoxymethyl | CH₂—CH=NOCH₃ | 1,1-Dimethyl-2-propynyl |
| Ethenyl | CH₂—CH=NOCH₃ | 1,1-Dimethyl-2-propynyl |
| 1-Methylethenyl | CH₂—CH=NOCH₃ | 1,1-Dimethyl-2-propynyl |
| 2-Propenyl | CH₂—CH=NOCH₃ | 1,1-Dimethyl-2-propynyl |
| Methoxy | CH₂—CH=NOCH₃ | 1,1-Dimethyl-2-propynyl |
| Ethoxy | CH₂—CH=NOCH₃ | 1,1-Dimethyl-2-propynyl |

-continued

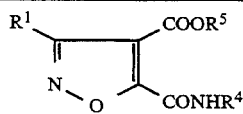

I

| R¹ | R⁵ | R⁴ |
|---|---|---|
| 1,1-Dimethylethoxy | $CH_2-CH=NOCH_3$ | 1,1-Dimethyl-2-propynyl |
| Furanyl | $CH_2-CH=NOCH_3$ | 1,1-Dimethyl-2-propynyl |
| Thienyl | $CH_2-CH=NOCH_3$ | 1,1-Dimethyl-2-propynyl |
| 3-Methyl-isoxazol-5-yl | $CH_2-CH=NOCH_3$ | 1,1-Dimethyl-2-propynyl |
| 3-Ethyl-isoxazol-5-yl | $CH_2-CH=NOCH_3$ | 1,1-Dimethyl-2-propynyl |
| 3-(1-Methylethyl)-isoxazol-5-yl | $CH_2-CH=NOCH_3$ | 1,1-Dimethyl-2-propynyl |
| 5-Methyl-isoxazol-3-yl | $CH_2-CH=NOCH_3$ | 1,1-Dimethyl-2-propynyl |
| Phenyl | $CH_2-CH=NOCH_3$ | 1,1-Dimethyl-2-propynyl |
| 4-Fluorophenyl | $CH_2-CH=NOCH_3$ | 1,1-Dimethyl-2-propynyl |
| 4-Chlorophenyl | $CH_2-CH=NOCH_3$ | 1,1-Dimethyl-2-propynyl |
| 2,4-Dichlorophenyl | $CH_2-CH=NOCH_3$ | 1,1-Dimethyl-2-propynyl |
| H | $CH_2-CH=NOCH_3$ | Cyclopropyl |
| Methyl | $CH_2-CH=NOCH_3$ | Cyclopropyl |
| Ethyl | $CH_2-CH=NOCH_3$ | Cyclopropyl |
| Propyl | $CH_2-CH=NOCH_3$ | Cyclopropyl |
| 1-Methylethyl | $CH_2-CH=NOCH_3$ | Cyclopropyl |
| 1-Methylpropyl | $CH_2-CH=NOCH_3$ | Cyclopropyl |
| 1,1-Dimethylethyl | $CH_2-CH=NOCH_3$ | Cyclopropyl |
| Cyclopropyl | $CH_2-CH=NOCH_3$ | Cyclopropyl |
| Cyclopentyl | $CH_2-CH=NOCH_3$ | Cyclopropyl |
| Cyclohexyl | $CH_2-CH=NOCH_3$ | Cyclopropyl |
| 1-Methylcyclopropyl | $CH_2-CH=NOCH_3$ | Cyclopropyl |
| Cyclopropylmethyl | $CH_2-CH=NOCH_3$ | Cyclopropyl |
| 1-Cyclopropylethyl | $CH_2-CH=NOCH_3$ | Cyclopropyl |
| Chloromethyl | $CH_2-CH=NOCH_3$ | Cyclopropyl |
| 1-Chloroethyl | $CH_2-CH=NOCH_3$ | Cyclopropyl |
| Methoxymethyl | $CH_2-CH=NOCH_3$ | Cyclopropyl |
| 1-Methylmethoxymethyl | $CH_2-CH=NOCH_3$ | Cyclopropyl |
| Ethenyl | $CH_2-CH=NOCH_3$ | Cyclopropyl |
| 1-Methylethenyl | $CH_2-CH=NOCH_3$ | Cyclopropyl |
| 2-Propenyl | $CH_2-CH=NOCH_3$ | Cyclopropyl |
| Methoxy | $CH_2-CH=NOCH_3$ | Cyclopropyl |
| Ethoxy | $CH_2-CH=NOCH_3$ | Cyclopropyl |
| 1,1-Dimethylethoxy | $CH_2-CH=NOCH_3$ | Cyclopropyl |
| Furanyl | $CH_2-CH=NOCH_3$ | Cyclopropyl |
| Thienyl | $CH_2-CH=NOCH_3$ | Cyclopropyl |
| 3-Methyl-isoxazol-5-yl | $CH_2-CH=NOCH_3$ | Cyclopropyl |
| 3-Ethyl-isoxazol-5-yl | $CH_2-CH=NOCH_3$ | Cyclopropyl |
| 3-(1-Methylethyl)-isoxazol-5-yl | $CH_2-CH=NOCH_3$ | Cyclopropyl |
| 5-Methyl-isoxazol-3-yl | $CH_2-CH=NOCH_3$ | Cyclopropyl |
| Phenyl | $CH_2-CH=NOCH_3$ | Cyclopropyl |
| 4-Fluorophenyl | $CH_2-CH=NOCH_3$ | Cyclopropyl |
| 4-Chlorophenyl | $CH_2-CH=NOCH_3$ | Cyclopropyl |
| 2,4-Dichlorophenyl | $CH_2-CH=NOCH_3$ | Cyclopropyl |
| H | $CH_2-CH=NOC_2H_5$ | 1,1-Dimethylethyl |
| Methyl | $CH_2-CH=NOC_2H_5$ | 1,1-Dimethylethyl |
| Ethyl | $CH_2-CH=NOC_2H_5$ | 1,1-Dimethylethyl |
| Propyl | $CH_2-CH=NOC_2H_5$ | 1,1-Dimethylethyl |
| 1-Methylethyl | $CH_2-CH=NOC_2H_5$ | 1,1-Dimethylethyl |
| 1-Methylpropyl | $CH_2-CH=NOC_2H_5$ | 1,1-Dimethylethyl |
| 1,1-Dimethylethyl | $CH_2-CH=NOC_2H_5$ | 1,1-Dimethylethyl |
| Cyclopropyl | $CH_2-CH=NOC_2H_5$ | 1,1-Dimethylethyl |
| Cyclopentyl | $CH_2-CH=NOC_2H_5$ | 1,1-Dimethylethyl |
| Cyclohexyl | $CH_2-CH=NOC_2H_5$ | 1,1-Dimethylethyl |
| 1-Methylcyclopropyl | $CH_2-CH=NOC_2H_5$ | 1,1-Dimethylethyl |
| Cyclopropylmethyl | $CH_2-CH=NOC_2H_5$ | 1,1-Dimethylethyl |
| 1-Cyclopropylethyl | $CH_2-CH=NOC_2H_5$ | 1,1-Dimethylethyl |
| Chloromethyl | $CH_2-CH=NOC_2H_5$ | 1,1-Dimethylethyl |
| 1-Chloroethyl | $CH_2-CH=NOC_2H_5$ | 1,1-Dimethylethyl |
| Methoxymethyl | $CH_2-CH=NOC_2H_5$ | 1,1-Dimethylethyl |
| 1-Methylmethoxymethyl | $CH_2-CH=NOC_2H_5$ | 1,1-Dimethylethyl |
| Ethenyl | $CH_2-CH=NOC_2H_5$ | 1,1-Dimethylethyl |
| 1-Methylethenyl | $CH_2-CH=NOC_2H_5$ | 1,1-Dimethylethyl |
| 2-Propenyl | $CH_2-CH=NOC_2H_5$ | 1,1-Dimethylethyl |
| Methoxy | $CH_2-CH=NOC_2H_5$ | 1,1-Dimethylethyl |
| Ethoxy | $CH_2-CH=NOC_2H_5$ | 1,1-Dimethylethyl |
| 1,1-Dimethylethoxy | $CH_2-CH=NOC_2H_5$ | 1,1-Dimethylethyl |
| Furanyl | $CH_2-CH=NOC_2H_5$ | 1,1-Dimethylethyl |
| Thienyl | $CH_2-CH=NOC_2H_5$ | 1,1-Dimethylethyl |
| 3-Methyl-isoxazol-5-yl | $CH_2-CH=NOC_2H_5$ | 1,1-Dimethylethyl |
| 3-Ethyl-isoxazol-5-yl | $CH_2-CH=NOC_2H_5$ | 1,1-Dimethylethyl |
| 3-(1-Methylethyl)-isoxazol-5-yl | $CH_2-CH=NOC_2H_5$ | 1,1-Dimethylethyl |
| 5-Methyl-isoxazol-3-yl | $CH_2-CH=NOC_2H_5$ | 1,1-Dimethylethyl |
| Phenyl | $CH_2-CH=NOC_2H_5$ | 1,1-Dimethylethyl |
| 4-Fluorophenyl | $CH_2-CH=NOC_2H_5$ | 1,1-Dimethylethyl |

-continued

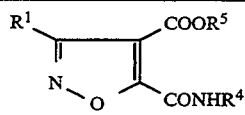

I

| R¹ | R⁵ | R⁴ |
|---|---|---|
| 4-Chlorophenyl | $CH_2-CH=NOC_2H_5$ | 1,1-Dimethylethyl |
| 2,4-Dichlorophenyl | $CH_2-CH=NOC_2H_5$ | 1,1-Dimethylethyl |
| H | $CH_2-CH=NOC_2H_5$ | 1,1-Dimethyl-2-propynyl |
| Methyl | $CH_2-CH=NOC_2H_5$ | 1,1-Dimethyl-2-propynyl |
| Ethyl | $CH_2-CH=NOC_2H_5$ | 1,1-Dimethyl-2-propynyl |
| Propyl | $CH_2-CH=NOC_2H_5$ | 1,1-Dimethyl-2-propynyl |
| 1-Methylethyl | $CH_2-CH=NOC_2H_5$ | 1,1-Dimethyl-2-propynyl |
| 1-Methylpropyl | $CH_2-CH=NOC_2H_5$ | 1,1-Dimethyl-2-propynyl |
| 1,1-Dimethylethyl | $CH_2-CH=NOC_2H_5$ | 1,1-Dimethyl-2-propynyl |
| Cyclopropyl | $CH_2-CH=NOC_2H_5$ | 1,1-Dimethyl-2-propynyl |
| Cyclopentyl | $CH_2-CH=NOC_2H_5$ | 1,1-Dimethyl-2-propynyl |
| Cyclohexyl | $CH_2-CH=NOC_2H_5$ | 1,1-Dimethyl-2-propynyl |
| 1-Methylcyclopropyl | $CH_2-CH=NOC_2H_5$ | 1,1-Dimethyl-2-propynyl |
| Cyclopropylmethyl | $CH_2-CH=NOC_2H_5$ | 1,1-Dimethyl-2-propynyl |
| 1-Cyclopropylethyl | $CH_2-CH=NOC_2H_5$ | 1,1-Dimethyl-2-propynyl |
| Chloromethyl | $CH_2-CH=NOC_2H_5$ | 1,1-Dimethyl-2-propynyl |
| 1-Chloroethyl | $CH_2-CH=NOC_2H_5$ | 1,1-Dimethyl-2-propynyl |
| Methoxymethyl | $CH_2-CH=NOC_2H_5$ | 1,1-Dimethyl-2-propynyl |
| 1-Methylmethoxymethyl | $CH_2-CH=NOC_2H_5$ | 1,1-Dimethyl-2-propynyl |
| Ethenyl | $CH_2-CH=NOC_2H_5$ | 1,1-Dimethyl-2-propynyl |
| 1-Methylethenyl | $CH_2-CH=NOC_2H_5$ | 1,1-Dimethyl-2-propynyl |
| 2-Propenyl | $CH_2-CH=NOC_2H_5$ | 1,1-Dimethyl-2-propynyl |
| Methoxy | $CH_2-CH=NOC_2H_5$ | 1,1-Dimethyl-2-propynyl |
| Ethoxy | $CH_2-CH=NOC_2H_5$ | 1,1-Dimethyl-2-propynyl |
| 1,1-Dimethylethoxy | $CH_2-CH=NOC_2H_5$ | 1,1-Dimethyl-2-propynyl |
| Furanyl | $CH_2-CH=NOC_2H_5$ | 1,1-Dimethyl-2-propynyl |
| Thienyl | $CH_2-CH=NOC_2H_5$ | 1,1-Dimethyl-2-propynyl |
| 3-Methyl-isoxazol-5-yl | $CH_2-CH=NOC_2H_5$ | 1,1-Dimethyl-2-propynyl |
| 3-Ethyl-isoxazol-5-yl | $CH_2-CH=NOC_2H_5$ | 1,1-Dimethyl-2-propynyl |
| 3-(1-Methylethyl)-isoxazol-5-yl | $CH_2-CH=NOC_2H_5$ | 1,1-Dimethyl-2-propynyl |
| 5-Methyl-isoxazol-3-yl | $CH_2-CH=NOC_2H_5$ | 1,1-Dimethyl-2-propynyl |
| Phenyl | $CH_2-CH=NOC_2H_5$ | 1,1-Dimethyl-2-propynyl |
| 4-Fluorophenyl | $CH_2-CH=NOC_2H_5$ | 1,1-Dimethyl-2-propynyl |
| 4-Chlorophenyl | $CH_2-CH=NOC_2H_5$ | 1,1-Dimethyl-2-propynyl |
| 2,4-Dichlorophenyl | $CH_2-CH=NOC_2H_5$ | 1,1-Dimethyl-2-propynyl |
| H | $CH_2-CH=NOC_2H_5$ | Cyclopropyl |
| Methyl | $CH_2-CH=NOC_2H_5$ | Cyclopropyl |
| Ethyl | $CH_2-CH=NOC_2H_5$ | Cyclopropyl |
| Propyl | $CH_2-CH=NOC_2H_5$ | Cyclopropyl |
| 1-Methylethyl | $CH_2-CH=NOC_2H_5$ | Cyclopropyl |
| 1-Methylpropyl | $CH_2-CH=NOC_2H_5$ | Cyclopropyl |
| 1,1-Dimethylethyl | $CH_2-CH=NOC_2H_5$ | Cyclopropyl |
| Cyclopropyl | $CH_2-CH=NOC_2H_5$ | Cyclopropyl |
| Cyclopentyl | $CH_2-CH=NOC_2H_5$ | Cyclopropyl |
| Cyclohexyl | $CH_2-CH=NOC_2H_5$ | Cyclopropyl |
| 1-Methylcyclopropyl | $CH_2-CH=NOC_2H_5$ | Cyclopropyl |
| Cyclopropylmethyl | $CH_2-CH=NOC_2H_5$ | Cyclopropyl |
| 1-Cyclopropylethyl | $CH_2-CH=NOC_2H_5$ | Cyclopropyl |
| Chloromethyl | $CH_2-CH=NOC_2H_5$ | Cyclopropyl |
| 1-Chloroethyl | $CH_2-CH=NOC_2H_5$ | Cyclopropyl |
| Methoxymethyl | $CH_2-CH=NOC_2H_5$ | Cyclopropyl |
| 1-Methylmethoxymethyl | $CH_2-CH=NOC_2H_5$ | Cyclopropyl |
| Ethenyl | $CH_2-CH=NOC_2H_5$ | Cyclopropyl |
| 1-Methylethenyl | $CH_2-CH=NOC_2H_5$ | Cyclopropyl |
| 2-Propenyl | $CH_2-CH=NOC_2H_5$ | Cyclopropyl |
| Methoxy | $CH_2-CH=NOC_2H_5$ | Cyclopropyl |
| Ethoxy | $CH_2-CH=NOC_2H_5$ | Cyclopropyl |
| 1,1-Dimethylethoxy | $CH_2-CH=NOC_2H_5$ | Cyclopropyl |
| Furanyl | $CH_2-CH=NOC_2H_5$ | Cyclopropyl |
| Thienyl | $CH_2-CH=NOC_2H_5$ | Cyclopropyl |
| 3-Methyl-isoxazol-5-yl | $CH_2-CH=NOC_2H_5$ | Cyclopropyl |
| 3-Ethyl-isoxazol-5-yl | $CH_2-CH=NOC_2H_5$ | Cyclopropyl |
| 3-(1-Methylethyl)-isoxazol-5-yl | $CH_2-CH=NOC_2H_5$ | Cyclopropyl |
| 5-Methyl-isoxazol-3-yl | $CH_2-CH=NOC_2H_5$ | Cyclopropyl |
| Phenyl | $CH_2-CH=NOC_2H_5$ | Cyclopropyl |
| 4-Fluorophenyl | $CH_2-CH=NOC_2H_5$ | Cyclopropyl |
| 4-Chlorophenyl | $CH_2-CH=NOC_2H_5$ | Cyclopropyl |
| 2,4-Dichlorophenyl | $CH_2-CH=NOC_2H_5$ | Cyclopropyl |
| H | $CH_2-CH=NOC_3H_7$ | 1,1-Dimethylethyl |
| Methyl | $CH_2-CH=NOC_3H_7$ | 1,1-Dimethylethyl |
| Ethyl | $CH_2-CH=NOC_3H_7$ | 1,1-Dimethylethyl |
| Propyl | $CH_2-CH=NOC_3H_7$ | 1,1-Dimethylethyl |
| 1-Methylethyl | $CH_2-CH=NOC_3H_7$ | 1,1-Dimethylethyl |
| 1-Methylpropyl | $CH_2-CH=NOC_3H_7$ | 1,1-Dimethylethyl |
| 1,1-Dimethylethyl | $CH_2-CH=NOC_3H_7$ | 1,1-Dimethylethyl |

-continued

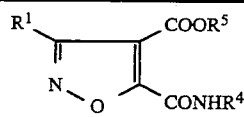

| R¹ | R⁵ | R⁴ |
|---|---|---|
| Cyclopropyl | $CH_2-CH=NOC_3H_7$ | 1,1-Dimethylethyl |
| Cyclopentyl | $CH_2-CH=NOC_3H_7$ | 1,1-Dimethylethyl |
| Cyclohexyl | $CH_2-CH=NOC_3H_7$ | 1,1-Dimethylethyl |
| 1-Methylcyclopropyl | $CH_2-CH=NOC_3H_7$ | 1,1-Dimethylethyl |
| Cyclopropylmethyl | $CH_2-CH=NOC_3H_7$ | 1,1-Dimethylethyl |
| 1-Cyclopropylethyl | $CH_2-CH=NOC_3H_7$ | 1,1-Dimethylethyl |
| Chloromethyl | $CH_2-CH=NOC_3H_7$ | 1,1-Dimethylethyl |
| 1-Chloroethyl | $CH_2-CH=NOC_3H_7$ | 1,1-Dimethylethyl |
| Methoxymethyl | $CH_2-CH=NOC_3H_7$ | 1,1-Dimethylethyl |
| 1-Methylmethoxymethyl | $CH_2-CH=NOC_3H_7$ | 1,1-Dimethylethyl |
| Ethenyl | $CH_2-CH=NOC_3H_7$ | 1,1-Dimethylethyl |
| 1-Methylethenyl | $CH_2-CH=NOC_3H_7$ | 1,1-Dimethylethyl |
| 2-Propenyl | $CH_2-CH=NOC_3H_7$ | 1,1-Dimethylethyl |
| Methoxy | $CH_2-CH=NOC_3H_7$ | 1,1-Dimethylethyl |
| Ethoxy | $CH_2-CH=NOC_3H_7$ | 1,1-Dimethylethyl |
| 1,1-Dimethylethoxy | $CH_2-CH=NOC_3H_7$ | 1,1-Dimethylethyl |
| Furanyl | $CH_2-CH=NOC_3H_7$ | 1,1-Dimethylethyl |
| Thienyl | $CH_2-CH=NOC_3H_7$ | 1,1-Dimethylethyl |
| 3-Methyl-isoxazol-5-yl | $CH_2-CH=NOC_3H_7$ | 1,1-Dimethylethyl |
| 3-Ethyl-isoxazol-5-yl | $CH_2-CH=NOC_3H_7$ | 1,1-Dimethylethyl |
| 3-(1-Methylethyl)-isoxazol-5-yl | $CH_2-CH=NOC_3H_7$ | 1,1-Dimethylethyl |
| 5-Methyl-isoxazol-3-yl | $CH_2-CH=NOC_3H_7$ | 1,1-Dimethylethyl |
| Phenyl | $CH_2-CH=NOC_3H_7$ | 1,1-Dimethylethyl |
| 4-Fluorophenyl | $CH_2-CH=NOC_3H_7$ | 1,1-Dimethylethyl |
| 4-Chlorophenyl | $CH_2-CH=NOC_3H_7$ | 1,1-Dimethylethyl |
| 2,4-Dichlorophenyl | $CH_2-CH=NOC_3H_7$ | 1,1-Dimethylethyl |
| H | $CH_2-CH=NOC_3H_7$ | 1,1-Dimethyl-2-propynyl |
| Methyl | $CH_2-CH=NOC_3H_7$ | 1,1-Dimethyl-2-propynyl |
| Ethyl | $CH_2-CH=NOC_3H_7$ | 1,1-Dimethyl-2-propynyl |
| Propyl | $CH_2-CH=NOC_3H_7$ | 1,1-Dimethyl-2-propynyl |
| 1-Methylethyl | $CH_2-CH=NOC_3H_7$ | 1,1-Dimethyl-2-propynyl |
| 1-Methylpropyl | $CH_2-CH=NOC_3H_7$ | 1,1-Dimethyl-2-propynyl |
| 1,1-Dimethylethyl | $CH_2-CH=NOC_3H_7$ | 1,1-Dimethyl-2-propynyl |
| Cyclopropyl | $CH_2-CH=NOC_3H_7$ | 1,1-Dimethyl-2-propynyl |
| Cyclopentyl | $CH_2-CH=NOC_3H_7$ | 1,1-Dimethyl-2-propynyl |
| Cyclohexyl | $CH_2-CH=NOC_3H_7$ | 1,1-Dimethyl-2-propynyl |
| 1-Methylcyclopropyl | $CH_2-CH=NOC_3H_7$ | 1,1-Dimethyl-2-propynyl |
| Cyclopropylmethyl | $CH_2-CH=NOC_3H_7$ | 1,1-Dimethyl-2-propynyl |
| 1-Cyclopropylethyl | $CH_2-CH=NOC_3H_7$ | 1,1-Dimethyl-2-propynyl |
| Chloromethyl | $CH_2-CH=NOC_3H_7$ | 1,1-Dimethyl-2-propynyl |
| 1-Chloroethyl | $CH_2-CH=NOC_3H_7$ | 1,1-Dimethyl-2-propynyl |
| Methoxymethyl | $CH_2-CH=NOC_3H_7$ | 1,1-Dimethyl-2-propynyl |
| 1-Methylmethoxymethyl | $CH_2-CH=NOC_3H_7$ | 1,1-Dimethyl-2-propynyl |
| Ethenyl | $CH_2-CH=NOC_3H_7$ | 1,1-Dimethyl-2-propynyl |
| 1-Methylethenyl | $CH_2-CH=NOC_3H_7$ | 1,1-Dimethyl-2-propynyl |
| 2-Propenyl | $CH_2-CH=NOC_3H_7$ | 1,1-Dimethyl-2-propynyl |
| Methoxy | $CH_2-CH=NOC_3H_7$ | 1,1-Dimethyl-2-propynyl |
| Ethoxy | $CH_2-CH=NOC_3H_7$ | 1,1-Dimethyl-2-propynyl |
| 1,1-Dimethylethoxy | $CH_2-CH=NOC_3H_7$ | 1,1-Dimethyl-2-propynyl |
| Furanyl | $CH_2-CH=NOC_3H_7$ | 1,1-Dimethyl-2-propynyl |
| Thienyl | $CH_2-CH=NOC_3H_7$ | 1,1-Dimethyl-2-propynyl |
| 3-Methyl-isoxazol-5-yl | $CH_2-CH=NOC_3H_7$ | 1,1-Dimethyl-2-propynyl |
| 3-Ethyl-isoxazol-5-yl | $CH_2-CH=NOC_3H_7$ | 1,1-Dimethyl-2-propynyl |
| 3-(1-Methylethyl)-isoxazol-5-yl | $CH_2-CH=NOC_3H_7$ | 1,1-Dimethyl-2-propynyl |
| 5-Methyl-isoxazol-3-yl | $CH_2-CH=NOC_3H_7$ | 1,1-Dimethyl-2-propynyl |
| Phenyl | $CH_2-CH=NOC_3H_7$ | 1,1-Dimethyl-2-propynyl |
| 4-Fluorophenyl | $CH_2-CH=NOC_3H_7$ | 1,1-Dimethyl-2-propynyl |
| 4-Chlorophenyl | $CH_2-CH=NOC_3H_7$ | 1,1-Dimethyl-2-propynyl |
| 2,4-Dichlorophenyl | $CH_2-CH=NOC_3H_7$ | 1,1-Dimethyl-2-propynyl |
| H | $CH_2-CH=NOC_3H_7$ | Cyclopropyl |
| Methyl | $CH_2-CH=NOC_3H_7$ | Cyclopropyl |
| Ethyl | $CH_2-CH=NOC_3H_7$ | Cyclopropyl |
| Propyl | $CH_2-CH=NOC_3H_7$ | Cyclopropyl |
| 1-Methylethyl | $CH_2-CH=NOC_3H_7$ | Cyclopropyl |
| 1-Methylpropyl | $CH_2-CH=NOC_3H_7$ | Cyclopropyl |
| 1,1-Dimethylethyl | $CH_2-CH=NOC_3H_7$ | Cyclopropyl |
| Cyclopropyl | $CH_2-CH=NOC_3H_7$ | Cyclopropyl |
| Cyclopentyl | $CH_2-CH=NOC_3H_7$ | Cyclopropyl |
| Cyclohexyl | $CH_2-CH=NOC_3H_7$ | Cyclopropyl |
| 1-Methylcyclopropyl | $CH_2-CH=NOC_3H_7$ | Cyclopropyl |
| Cyclopropylmethyl | $CH_2-CH=NOC_3H_7$ | Cyclopropyl |
| 1-Cyclopropylethyl | $CH_2-CH=NOC_3H_7$ | Cyclopropyl |
| Chloromethyl | $CH_2-CH=NOC_3H_7$ | Cyclopropyl |
| 1-Chloroethyl | $CH_2-CH=NOC_3H_7$ | Cyclopropyl |
| Methoxymethyl | $CH_2-CH=NOC_3H_7$ | Cyclopropyl |

-continued

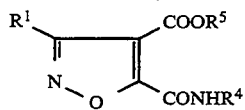

I

| R¹ | R⁵ | R⁴ |
|---|---|---|
| 1-Methylmethoxymethyl | CH₂—CH=NOC₃H₇ | Cyclopropyl |
| Ethenyl | CH₂—CH=NOC₃H₇ | Cyclopropyl |
| 1-Methylethenyl | CH₂—CH=NOC₃H₇ | Cyclopropyl |
| 2-Propenyl | CH₂—CH=NOC₃H₇ | Cyclopropyl |
| Methoxy | CH₂—CH=NOC₃H₇ | Cyclopropyl |
| Ethoxy | CH₂—CH=NOC₃H₇ | Cyclopropyl |
| 1,1-Dimethylethoxy | CH₂—CH=NOC₃H₇ | Cyclopropyl |
| Furanyl | CH₂—CH=NOC₃H₇ | Cyclopropyl |
| Thienyl | CH₂—CH=NOC₃H₇ | Cyclopropyl |
| 3-Methyl-isoxazol-5-yl | CH₂—CH=NOC₃H₇ | Cyclopropyl |
| 3-Ethyl-isoxazol-5-yl | CH₂—CH=NOC₃H₇ | Cyclopropyl |
| 3-(1-Methylethyl)-isoxazol-5-yl | CH₂—CH=NOC₃H₇ | Cyclopropyl |
| 5-Methyl-isoxazol-3-yl | CH₂—CH=NOC₃H₇ | Cyclopropyl |
| Phenyl | CH₂—CH=NOC₃H₇ | Cyclopropyl |
| 4-Fluorophenyl | CH₂—CH=NOC₃H₇ | Cyclopropyl |
| 4-Chlorophenyl | CH₂—CH=NOC₃H₇ | Cyclopropyl |
| 2,4-Dichlorophenyl | CH₂—CH=NOC₃H₇ | Cyclopropyl |
| H | CH₂—C(CH₃)=NOCH₃ | 1,1-Dimethylethyl |
| Methyl | CH₂—C(CH₃)=NOCH₃ | 1,1-Dimethylethyl |
| Ethyl | CH₂—C(CH₃)=NOCH₃ | 1,1-Dimethylethyl |
| Propyl | CH₂—C(CH₃)=NOCH₃ | 1,1-Dimethylethyl |
| 1-Methylethyl | CH₂—C(CH₃)=NOCH₃ | 1,1-Dimethylethyl |
| 1-Methylpropyl | CH₂—C(CH₃)=NOCH₃ | 1,1-Dimethylethyl |
| 1,1-Dimethylethyl | CH₂—C(CH₃)=NOCH₃ | 1,1-Dimethylethyl |
| Cyclopropyl | CH₂—C(CH₃)=NOCH₃ | 1,1-Dimethylethyl |
| Cyclopentyl | CH₂—C(CH₃)=NOCH₃ | 1,1-Dimethylethyl |
| Cyclohexyl | CH₂—C(CH₃)=NOCH₃ | 1,1-Dimethylethyl |
| 1-Methylcyclopropyl | CH₂—C(CH₃)=NOCH₃ | 1,1-Dimethylethyl |
| Cyclopropylmethyl | CH₂—C(CH₃)=NOCH₃ | 1,1-Dimethylethyl |
| 1-Cyclopropylethyl | CH₂—C(CH₃)=NOCH₃ | 1,1-Dimethylethyl |
| Chloromethyl | CH₂—C(CH₃)=NOCH₃ | 1,1-Dimethylethyl |
| 1-Chloroethyl | CH₂—C(CH₃)=NOCH₃ | 1,1-Dimethylethyl |
| Methoxymethyl | CH₂—C(CH₃)=NOCH₃ | 1,1-Dimethylethyl |
| 1-Methylmethoxymethyl | CH₂—C(CH₃)=NOCH₃ | 1,1-Dimethylethyl |
| Ethenyl | CH₂—C(CH₃)=NOCH₃ | 1,1-Dimethylethyl |
| 1-Methylethenyl | CH₂—C(CH₃)=NOCH₃ | 1,1-Dimethylethyl |
| 2-Propenyl | CH₂—C(CH₃)=NOCH₃ | 1,1-Dimethylethyl |
| Methoxy | CH₂—C(CH₃)=NOCH₃ | 1,1-Dimethylethyl |
| Ethoxy | CH₂—C(CH₃)=NOCH₃ | 1,1-Dimethylethyl |
| 1,1-Dimethylethoxy | CH₂—C(CH₃)=NOCH₃ | 1,1-Dimethylethyl |
| Furanyl | CH₂—C(CH₃)=NOCH₃ | 1,1-Dimethylethyl |
| Thienyl | CH₂—C(CH₃)=NOCH₃ | 1,1-Dimethylethyl |
| 3-Methyl-isoxazol-5-yl | CH₂—C(CH₃)=NOCH₃ | 1,1-Dimethylethyl |
| 3-Ethyl-isoxazol-5-yl | CH₂—C(CH₃)=NOCH₃ | 1,1-Dimethylethyl |
| 3-(1-Methylethyl)-isoxazol-5-yl | CH₂—C(CH₃)=NOCH₃ | 1,1-Dimethylethyl |
| 5-Methyl-isoxazol-3-yl | CH₂—C(CH₃)=NOCH₃ | 1,1-Dimethylethyl |
| Phenyl | CH₂—C(CH₃)=NOCH₃ | 1,1-Dimethylethyl |
| 4-Fluorophenyl | CH₂—C(CH₃)=NOCH₃ | 1,1-Dimethylethyl |
| 4-Chlorophenyl | CH₂—C(CH₃)=NOCH₃ | 1,1-Dimethylethyl |
| 2,4-Dichlorophenyl | CH₂—C(CH₃)=NOCH₃ | 1,1-Dimethylethyl |
| H | CH₂—C(CH₃)=NOCH₃ | 1,1-Dimethyl-2-propynyl |
| Methyl | CH₂—C(CH₃)=NOCH₃ | 1,1-Dimethyl-2-propynyl |
| Ethyl | CH₂—C(CH₃)=NOCH₃ | 1,1-Dimethyl-2-propynyl |
| Propyl | CH₂—C(CH₃)=NOCH₃ | 1,1-Dimethyl-2-propynyl |
| 1-Methylethyl | CH₂—C(CH₃)=NOCH₃ | 1,1-Dimethyl-2-propynyl |
| 1-Methylpropyl | CH₂—C(CH₃)=NOCH₃ | 1,1-Dimethyl-2-propynyl |
| 1,1-Dimethylethyl | CH₂—C(CH₃)=NOCH₃ | 1,1-Dimethyl-2-propynyl |
| Cyclopropyl | CH₂—C(CH₃)=NOCH₃ | 1,1-Dimethyl-2-propynyl |
| Cyclopentyl | CH₂—C(CH₃)=NOCH₃ | 1,1-Dimethyl-2-propynyl |
| Cyclohexyl | CH₂—C(CH₃)=NOCH₃ | 1,1-Dimethyl-2-propynyl |
| 1-Methylcyclopropyl | CH₂—C(CH₃)=NOCH₃ | 1,1-Dimethyl-2-propynyl |
| Cyclopropylmethyl | CH₂—C(CH₃)=NOCH₃ | 1,1-Dimethyl-2-propynyl |
| 1-Cyclopropylethyl | CH₂—C(CH₃)=NOCH₃ | 1,1-Dimethyl-2-propynyl |
| Chloromethyl | CH₂—C(CH₃)=NOCH₃ | 1,1-Dimethyl-2-propynyl |
| 1-Chloroethyl | CH₂—C(CH₃)=NOCH₃ | 1,1-Dimethyl-2-propynyl |
| Methoxymethyl | CH₂—C(CH₃)=NOCH₃ | 1,1-Dimethyl-2-propynyl |
| 1-Methylmethoxymethyl | CH₂—C(CH₃)=NOCH₃ | 1,1-Dimethyl-2-propynyl |
| Ethenyl | CH₂—C(CH₃)=NOCH₃ | 1,1-Dimethyl-2-propynyl |
| 1-Methylethenyl | CH₂—C(CH₃)=NOCH₃ | 1,1-Dimethyl-2-propynyl |
| 2-Propenyl | CH₂—C(CH₃)=NOCH₃ | 1,1-Dimethyl-2-propynyl |
| Methoxy | CH₂—C(CH₃)=NOCH₃ | 1,1-Dimethyl-2-propynyl |
| Ethoxy | CH₂—C(CH₃)=NOCH₃ | 1,1-Dimethyl-2-propynyl |
| 1,1-Dimethylethoxy | CH₂—C(CH₃)=NOCH₃ | 1,1-Dimethyl-2-propynyl |
| Furanyl | CH₂—C(CH₃)=NOCH₃ | 1,1-Dimethyl-2-propynyl |
| Thienyl | CH₂—C(CH₃)=NOCH₃ | 1,1-Dimethyl-2-propynyl |

-continued

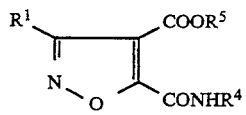   I

| R¹ | R⁵ | R⁴ |
|---|---|---|
| 3-Methyl-isoxazol-5-yl | $CH_2-C(CH_3)=NOCH_3$ | 1,1-Dimethyl-2-propynyl |
| 3-Ethyl-isoxazol-5-yl | $CH_2-C(CH_3)=NOCH_3$ | 1,1-Dimethyl-2-propynyl |
| 3-(1-Methylethyl)-isoxazol-5-yl | $CH_2-C(CH_3)=NOCH_3$ | 1,1-Dimethyl-2-propynyl |
| 5-Methyl-isoxazol-3-yl | $CH_2-C(CH_3)=NOCH_3$ | 1,1-Dimethyl-2-propynyl |
| Phenyl | $CH_2-C(CH_3)=NOCH_3$ | 1,1-Dimethyl-2-propynyl |
| 4-Fluorophenyl | $CH_2-C(CH_3)=NOCH_3$ | 1,1-Dimethyl-2-propynyl |
| 4-Chlorophenyl | $CH_2-C(CH_3)=NOCH_3$ | 1,1-Dimethyl-2-propynyl |
| 2,4-Dichlorophenyl | $CH_2-C(CH_3)=NOCH_3$ | 1,1-Dimethyl-2-propynyl |
| H | $CH_2-C(CH_3)=NOCH_3$ | Cyclopropyl |
| Methyl | $CH_2-C(CH_3)=NOCH_3$ | Cyclopropyl |
| Ethyl | $CH_2-C(CH_3)=NOCH_3$ | Cyclopropyl |
| Propyl | $CH_2-C(CH_3)=NOCH_3$ | Cyclopropyl |
| 1-Methylethyl | $CH_2-C(CH_3)=NOCH_3$ | Cyclopropyl |
| 1-Methylpropyl | $CH_2-C(CH_3)=NOCH_3$ | Cyclopropyl |
| 1,1-Dimethylethyl | $CH_2-C(CH_3)=NOCH_3$ | Cyclopropyl |
| Cyclopropyl | $CH_2-C(CH_3)=NOCH_3$ | Cyclopropyl |
| Cyclopentyl | $CH_2-C(CH_3)=NOCH_3$ | Cyclopropyl |
| Cyclohexyl | $CH_2-C(CH_3)=NOCH_3$ | Cyclopropyl |
| 1-Methylcyclopropyl | $CH_2-C(CH_3)=NOCH_3$ | Cyclopropyl |
| Cyclopropylmethyl | $CH_2-C(CH_3)=NOCH_3$ | Cyclopropyl |
| 1-Cyclopropylethyl | $CH_2-C(CH_3)=NOCH_3$ | Cyclopropyl |
| Chloromethyl | $CH_2-C(CH_3)=NOCH_3$ | Cyclopropyl |
| 1-Chloroethyl | $CH_2-C(CH_3)=NOCH_3$ | Cyclopropyl |
| Methoxymethyl | $CH_2-C(CH_3)=NOCH_3$ | Cyclopropyl |
| 1-Methylmethoxymethyl | $CH_2-C(CH_3)=NOCH_3$ | Cyclopropyl |
| Ethenyl | $CH_2-C(CH_3)=NOCH_3$ | Cyclopropyl |
| 1-Methylethenyl | $CH_2-C(CH_3)=NOCH_3$ | Cyclopropyl |
| 2-Propenyl | $CH_2-C(CH_3)=NOCH_3$ | Cyclopropyl |
| Methoxy | $CH_2-C(CH_3)=NOCH_3$ | Cyclopropyl |
| Ethoxy | $CH_2-C(CH_3)=NOCH_3$ | Cyclopropyl |
| 1,1-Dimethylethoxy | $CH_2-C(CH_3)=NOCH_3$ | Cyclopropyl |
| Furanyl | $CH_2-C(CH_3)=NOCH_3$ | Cyclopropyl |
| Thienyl | $CH_2-C(CH_3)=NOCH_3$ | Cyclopropyl |
| 3-Methyl-isoxazol-5-yl | $CH_2-C(CH_3)=NOCH_3$ | Cyclopropyl |
| 3-Ethyl-isoxazol-5-yl | $CH_2-C(CH_3)=NOCH_3$ | Cyclopropyl |
| 3-(1-Methylethyl)-isoxazol-5-yl | $CH_2-C(CH_3)=NOCH_3$ | Cyclopropyl |
| 5-Methyl-isoxazol-3-yl | $CH_2-C(CH_3)=NOCH_3$ | Cyclopropyl |
| Phenyl | $CH_2-C(CH_3)=NOCH_3$ | Cyclopropyl |
| 4-Fluorophenyl | $CH_2-C(CH_3)=NOCH_3$ | Cyclopropyl |
| 4-Chlorophenyl | $CH_2-C(CH_3)=NOCH_3$ | Cyclopropyl |
| 2,4-Dichlorophenyl | $CH_2-C(CH_3)=NOCH_3$ | Cyclopropyl |
| H | $CH_2-CH=NOCH_2-CH=CH_2$ | 1,1-Dimethylethyl |
| Methyl | $CH_2-CH=NOCH_2-CH=CH_2$ | 1,1-Dimethylethyl |
| Ethyl | $CH_2-CH=NOCH_2-CH=CH_2$ | 1,1-Dimethylethyl |
| Propyl | $CH_2-CH=NOCH_2-CH=CH_2$ | 1,1-Dimethylethyl |
| 1-Methylethyl | $CH_2-CH=NOCH_2-CH=CH_2$ | 1,1-Dimethylethyl |
| 1-Methylpropyl | $CH_2-CH=NOCH_2-CH=CH_2$ | 1,1-Dimethylethyl |
| 1,1-Dimethylethyl | $CH_2-CH=NOCH_2-CH=CH_2$ | 1,1-Dimethylethyl |
| Cyclopropyl | $CH_2-CH=NOCH_2-CH=CH_2$ | 1,1-Dimethylethyl |
| Cyclopentyl | $CH_2-CH=NOCH_2-CH=CH_2$ | 1,1-Dimethylethyl |
| Cyclohexyl | $CH_2-CH=NOCH_2-CH=CH_2$ | 1,1-Dimethylethyl |
| 1-Methylcyclopropyl | $CH_2-CH=NOCH_2-CH=CH_2$ | 1,1-Dimethylethyl |
| Cyclopropylmethyl | $CH_2-CH=NOCH_2-CH=CH_2$ | 1,1-Dimethylethyl |
| 1-Cyclopropylethyl | $CH_2-CH=NOCH_2-CH=CH_2$ | 1,1-Dimethylethyl |
| Chloromethyl | $CH_2-CH=NOCH_2-CH=CH_2$ | 1,1-Dimethylethyl |
| 1-Chloroethyl | $CH_2-CH=NOCH_2-CH=CH_2$ | 1,1-Dimethylethyl |
| Methoxymethyl | $CH_2-CH=NOCH_2-CH=CH_2$ | 1,1-Dimethylethyl |
| 1-Methylmethoxymethyl | $CH_2-CH=NOCH_2-CH=CH_2$ | 1,1-Dimethylethyl |
| Ethenyl | $CH_2-CH=NOCH_2-CH=CH_2$ | 1,1-Dimethylethyl |
| 1-Methylethenyl | $CH_2-CH=NOCH_2-CH=CH_2$ | 1,1-Dimethylethyl |
| 2-Propenyl | $CH_2-CH=NOCH_2-CH=CH_2$ | 1,1-Dimethylethyl |
| Methoxy | $CH_2-CH=NOCH_2-CH=CH_2$ | 1,1-Dimethylethyl |
| Ethoxy | $CH_2-CH=NOCH_2-CH=CH_2$ | 1,1-Dimethylethyl |
| 1,1-Dimethylethoxy | $CH_2-CH=NOCH_2-CH=CH_2$ | 1,1-Dimethylethyl |
| Furanyl | $CH_2-CH=NOCH_2-CH=CH_2$ | 1,1-Dimethylethyl |
| Thienyl | $CH_2-CH=NOCH_2-CH=CH_2$ | 1,1-Dimethylethyl |
| 3-Methyl-isoxazol-5-yl | $CH_2-CH=NOCH_2-CH=CH_2$ | 1,1-Dimethylethyl |
| 3-Ethyl-isoxazol-5-yl | $CH_2-CH=NOCH_2-CH=CH_2$ | 1,1-Dimethylethyl |
| 3-(1-Methylethyl)-isoxazol-5-yl | $CH_2-CH=NOCH_2-CH=CH_2$ | 1,1-Dimethylethyl |
| 5-Methyl-isoxazol-3-yl | $CH_2-CH=NOCH_2-CH=CH_2$ | 1,1-Dimethylethyl |
| Phenyl | $CH_2-CH=NOCH_2-CH=CH_2$ | 1,1-Dimethylethyl |
| 4-Fluorophenyl | $CH_2-CH=NOCH_2-CH=CH_2$ | 1,1-Dimethylethyl |
| 4-Chlorophenyl | $CH_2-CH=NOCH_2-CH=CH_2$ | 1,1-Dimethylethyl |
| 2,4-Dichlorophenyl | $CH_2-CH=NOCH_2-CH=CH_2$ | 1,1-Dimethylethyl |
| H | $CH_2-CH=NOCH_2-CH=CH_2$ | 1,1-Dimethyl-2-propynyl |

-continued

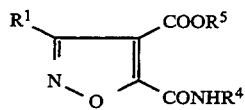

I

| $R^1$ | $R^5$ | $R^4$ |
|---|---|---|
| Methyl | $CH_2-CH=NOCH_2-CH=CH_2$ | 1,1-Dimethyl-2-propynyl |
| Ethyl | $CH_2-CH=NOCH_2-CH=CH_2$ | 1,1-Dimethyl-2-propynyl |
| Propyl | $CH_2-CH=NOCH_2-CH=CH_2$ | 1,1-Dimethyl-2-propynyl |
| 1-Methylethyl | $CH_2-CH=NOCH_2-CH=CH_2$ | 1,1-Dimethyl-2-propynyl |
| 1-Methylpropyl | $CH_2-CH=NOCH_2-CH=CH_2$ | 1,1-Dimethyl-2-propynyl |
| 1,1-Dimethylethyl | $CH_2-CH=NOCH_2-CH=CH_2$ | 1,1-Dimethyl-2-propynyl |
| Cyclopropyl | $CH_2-CH=NOCH_2-CH=CH_2$ | 1,1-Dimethyl-2-propynyl |
| Cyclopentyl | $CH_2-CH=NOCH_2-CH=CH_2$ | 1,1-Dimethyl-2-propynyl |
| Cyclohexyl | $CH_2-CH=NOCH_2-CH=CH_2$ | 1,1-Dimethyl-2-propynyl |
| 1-Methylcyclopropyl | $CH_2-CH=NOCH_2-CH=CH_2$ | 1,1-Dimethyl-2-propynyl |
| Cyclopropylmethyl | $CH_2-CH=NOCH_2-CH=CH_2$ | 1,1-Dimethyl-2-propynyl |
| 1-Cyclopropylethyl | $CH_2-CH=NOCH_2-CH=CH_2$ | 1,1-Dimethyl-2-propynyl |
| Chloromethyl | $CH_2-CH=NOCH_2-CH=CH_2$ | 1,1-Dimethyl-2-propynyl |
| 1-Chloroethyl | $CH_2-CH=NOCH_2-CH=CH_2$ | 1,1-Dimethyl-2-propynyl |
| Methoxymethyl | $CH_2-CH=NOCH_2-CH=CH_2$ | 1,1-Dimethyl-2-propynyl |
| 1-Methylmethoxymethyl | $CH_2-CH=NOCH_2-CH=CH_2$ | 1,1-Dimethyl-2-propynyl |
| Ethenyl | $CH_2-CH=NOCH_2-CH=CH_2$ | 1,1-Dimethyl-2-propynyl |
| 1-Methylethenyl | $CH_2-CH=NOCH_2-CH=CH_2$ | 1,1-Dimethyl-2-propynyl |
| 2-Propenyl | $CH_2-CH=NOCH_2-CH=CH_2$ | 1,1-Dimethyl-2-propynyl |
| Methoxy | $CH_2-CH=NOCH_2-CH=CH_2$ | 1,1-Dimethyl-2-propynyl |
| Ethoxy | $CH_2-CH=NOCH_2-CH=CH_2$ | 1,1-Dimethyl-2-propynyl |
| 1,1-Dimethylethoxy | $CH_2-CH=NOCH_2-CH=CH_2$ | 1,1-Dimethyl-2-propynyl |
| Furanyl | $CH_2-CH=NOCH_2-CH=CH_2$ | 1,1-Dimethyl-2-propynyl |
| Thienyl | $CH_2-CH=NOCH_2-CH=CH_2$ | 1,1-Dimethyl-2-propynyl |
| 3-Methyl-isoxazol-5-yl | $CH_2-CH=NOCH_2-CH=CH_2$ | 1,1-Dimethyl-2-propynyl |
| 3-Ethyl-isoxazol-5-yl | $CH_2-CH=NOCH_2-CH=CH_2$ | 1,1-Dimethyl-2-propynyl |
| 3-(1-Methylethyl)-isoxazol-5-yl | $CH_2-CH=NOCH_2-CH=CH_2$ | 1,1-Dimethyl-2-propynyl |
| 5-Methyl-isoxazol-3-yl | $CH_2-CH=NOCH_2-CH=CH_2$ | 1,1-Dimethyl-2-propynyl |
| Phenyl | $CH_2-CH=NOCH_2-CH=CH_2$ | 1,1-Dimethyl-2-propynyl |
| 4-Fluorophenyl | $CH_2-CH=NOCH_2-CH=CH_2$ | 1,1-Dimethyl-2-propynyl |
| 4-Chlorophenyl | $CH_2-CH=NOCH_2-CH=CH_2$ | 1,1-Dimethyl-2-propynyl |
| 2,4-Dichlorophenyl | $CH_2-CH=NOCH_2-CH=CH_2$ | 1,1-Dimethyl-2-propynyl |
| H | $CH_2-CH=NOCH_2-CH=CH_2$ | Cyclopropyl |
| Methyl | $CH_2-CH=NOCH_2-CH=CH_2$ | Cyclopropyl |
| Ethyl | $CH_2-CH=NOCH_2-CH=CH_2$ | Cyclopropyl |
| Propyl | $CH_2-CH=NOCH_2-CH=CH_2$ | Cyclopropyl |
| 1-Methylethyl | $CH_2-CH=NOCH_2-CH=CH_2$ | Cyclopropyl |
| 1-Methylpropyl | $CH_2-CH=NOCH_2-CH=CH_2$ | Cyclopropyl |
| 1,1-Dimethylethyl | $CH_2-CH=NOCH_2-CH=CH_2$ | Cyclopropyl |
| Cyclopropyl | $CH_2-CH=NOCH_2-CH=CH_2$ | Cyclopropyl |
| Cyclopentyl | $CH_2-CH=NOCH_2-CH=CH_2$ | Cyclopropyl |
| Cyclohexyl | $CH_2-CH=NOCH_2-CH=CH_2$ | Cyclopropyl |
| 1-Methylcyclopropyl | $CH_2-CH=NOCH_2-CH=CH_2$ | Cyclopropyl |
| Cyclopropylmethyl | $CH_2-CH=NOCH_2-CH=CH_2$ | Cyclopropyl |
| 1-Cyclopropylethyl | $CH_2-CH=NOCH_2-CH=CH_2$ | Cyclopropyl |
| Chloromethyl | $CH_2-CH=NOCH_2-CH=CH_2$ | Cyclopropyl |
| 1-Chloroethyl | $CH_2-CH=NOCH_2-CH=CH_2$ | Cyclopropyl |
| Methoxymethyl | $CH_2-CH=NOCH_2-CH=CH_2$ | Cyclopropyl |
| 1-Methylmethoxymethyl | $CH_2-CH=NOCH_2-CH=CH_2$ | Cyclopropyl |
| Ethenyl | $CH_2-CH=NOCH_2-CH=CH_2$ | Cyclopropyl |
| 1-Methylethenyl | $CH_2-CH=NOCH_2-CH=CH_2$ | Cyclopropyl |
| 2-Propenyl | $CH_2-CH=NOCH_2-CH=CH_2$ | Cyclopropyl |
| Methoxy | $CH_2-CH=NOCH_2-CH=CH_2$ | Cyclopropyl |
| Ethoxy | $CH_2-CH=NOCH_2-CH=CH_2$ | Cyclopropyl |
| 1,1-Dimethylethoxy | $CH_2-CH=NOCH_2-CH=CH_2$ | Cyclopropyl |
| Furanyl | $CH_2-CH=NOCH_2-CH=CH_2$ | Cyclopropyl |
| Thienyl | $CH_2-CH=NOCH_2-CH=CH_2$ | Cyclopropyl |
| 3-Methyl-isoxazol-5-yl | $CH_2-CH=NOCH_2-CH=CH_2$ | Cyclopropyl |
| 3-Ethyl-isoxazol-5-yl | $CH_2-CH=NOCH_2-CH=CH_2$ | Cyclopropyl |
| 3-(1-Methylethyl)-isoxazol-5-yl | $CH_2-CH=NOCH_2-CH=CH_2$ | Cyclopropyl |
| 5-Methyl-isoxazol-3-yl | $CH_2-CH=NOCH_2-CH=CH_2$ | Cyclopropyl |
| Phenyl | $CH_2-CH=NOCH_2-CH=CH_2$ | Cyclopropyl |
| 4-Fluorophenyl | $CH_2-CH=NOCH_2-CH=CH_2$ | Cyclopropyl |
| 4-Chlorophenyl | $CH_2-CH=NOCH_2-CH=CH_2$ | Cyclopropyl |
| 2,4-Dichlorophenyl | $CH_2-CH=NOCH_2-CH=CH_2$ | Cyclopropyl |
| H | $CH_2-CH=NOCH_2-C\equiv CH$ | 1,1-Dimethylethyl |
| Methyl | $CH_2-CH=NOCH_2-C\equiv CH$ | 1,1-Dimethylethyl |
| Ethyl | $CH_2-CH=NOCH_2-C\equiv CH$ | 1,1-Dimethylethyl |
| Propyl | $CH_2-CH=NOCH_2-C\equiv CH$ | 1,1-Dimethylethyl |
| 1-Methylethyl | $CH_2-CH=NOCH_2-C\equiv CH$ | 1,1-Dimethylethyl |
| 1-Methylpropyl | $CH_2-CH=NOCH_2-C\equiv CH$ | 1,1-Dimethylethyl |
| 1,1-Dimethylethyl | $CH_2-CH=NOCH_2-C\equiv CH$ | 1,1-Dimethylethyl |
| Cyclopropyl | $CH_2-CH=NOCH_2-C\equiv CH$ | 1,1-Dimethylethyl |
| Cyclopentyl | $CH_2-CH=NOCH_2-C\equiv CH$ | 1,1-Dimethylethyl |
| Cyclohexyl | $CH_2-CH=NOCH_2-C\equiv CH$ | 1,1-Dimethylethyl |

-continued

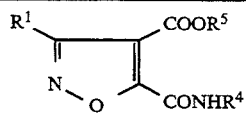

| R¹ | R⁵ | R⁴ |
| --- | --- | --- |
| 1-Methylcyclopropyl | $CH_2-CH=NOCH_2-C\equiv CH$ | 1,1-Dimethylethyl |
| Cyclopropylmethyl | $CH_2-CH=NOCH_2-C\equiv CH$ | 1,1-Dimethylethyl |
| 1-Cyclopropylethyl | $CH_2-CH=NOCH_2-C\equiv CH$ | 1,1-Dimethylethyl |
| Chloromethyl | $CH_2-CH=NOCH_2-C\equiv CH$ | 1,1-Dimethylethyl |
| 1-Chloroethyl | $CH_2-CH=NOCH_2-C\equiv CH$ | 1,1-Dimethylethyl |
| Methoxymethyl | $CH_2-CH=NOCH_2-C\equiv CH$ | 1,1-Dimethylethyl |
| 1-Methylmethoxymethyl | $CH_2-CH=NOCH_2-C\equiv CH$ | 1,1-Dimethylethyl |
| Ethenyl | $CH_2-CH=NOCH_2-C\equiv CH$ | 1,1-Dimethylethyl |
| 1-Methylethenyl | $CH_2-CH=NOCH_2-C\equiv CH$ | 1,1-Dimethylethyl |
| 2-Propenyl | $CH_2-CH=NOCH_2-C\equiv CH$ | 1,1-Dimethylethyl |
| Methoxy | $CH_2-CH=NOCH_2-C\equiv CH$ | 1,1-Dimethylethyl |
| Ethoxy | $CH_2-CH=NOCH_2-C\equiv CH$ | 1,1-Dimethylethyl |
| 1,1-Dimethylethoxy | $CH_2-CH=NOCH_2-C\equiv CH$ | 1,1-Dimethylethyl |
| Furanyl | $CH_2-CH=NOCH_2-C\equiv CH$ | 1,1-Dimethylethyl |
| Thienyl | $CH_2-CH=NOCH_2-C\equiv CH$ | 1,1-Dimethylethyl |
| 3-Methyl-isoxazol-5-yl | $CH_2-CH=NOCH_2-C\equiv CH$ | 1,1-Dimethylethyl |
| 3-Ethyl-isoxazol-5-yl | $CH_2-CH=NOCH_2-C\equiv CH$ | 1,1-Dimethylethyl |
| 3-(1-Methylethyl)-isoxazol-5-yl | $CH_2-CH=NOCH_2-C\equiv CH$ | 1,1-Dimethylethyl |
| 5-Methyl-isoxazol-3-yl | $CH_2-CH=NOCH_2-C\equiv CH$ | 1,1-Dimethylethyl |
| Phenyl | $CH_2-CH=NOCH_2-C\equiv CH$ | 1,1-Dimethylethyl |
| 4-Fluorophenyl | $CH_2-CH=NOCH_2-C\equiv CH$ | 1,1-Dimethylethyl |
| 4-Chlorophenyl | $CH_2-CH=NOCH_2-C\equiv CH$ | 1,1-Dimethylethyl |
| 2,4-Dichlorophenyl | $CH_2-CH=NOCH_2-C\equiv CH$ | 1,1-Dimethylethyl |
| H | $CH_2-CH=NOCH_2-C\equiv CH$ | 1,1-Dimethyl-2-propynyl |
| Methyl | $CH_2-CH=NOCH_2-C\equiv CH$ | 1,1-Dimethyl-2-propynyl |
| Ethyl | $CH_2-CH=NOCH_2-C\equiv CH$ | 1,1-Dimethyl-2-propynyl |
| Propyl | $CH_2-CH=NOCH_2-C\equiv CH$ | 1,1-Dimethyl-2-propynyl |
| 1-Methylethyl | $CH_2-CH=NOCH_2-C\equiv CH$ | 1,1-Dimethyl-2-propynyl |
| 1-Methylpropyl | $CH_2-CH=NOCH_2-C\equiv CH$ | 1,1-Dimethyl-2-propynyl |
| 1,1-Dimethylethyl | $CH_2-CH=NOCH_2-C\equiv CH$ | 1,1-Dimethyl-2-propynyl |
| Cyclopropyl | $CH_2-CH=NOCH_2-C\equiv CH$ | 1,1-Dimethyl-2-propynyl |
| Cyclopentyl | $CH_2-CH=NOCH_2-C\equiv CH$ | 1,1-Dimethyl-2-propynyl |
| Cyclohexyl | $CH_2-CH=NOCH_2-C\equiv CH$ | 1,1-Dimethyl-2-propynyl |
| 1-Methylcyclopropyl | $CH_2-CH=NOCH_2-C\equiv CH$ | 1,1-Dimethyl-2-propynyl |
| Cyclopropylmethyl | $CH_2-CH=NOCH_2-C\equiv CH$ | 1,1-Dimethyl-2-propynyl |
| 1-Cyclopropylethyl | $CH_2-CH=NOCH_2-C\equiv CH$ | 1,1-Dimethyl-2-propynyl |
| Chloromethyl | $CH_2-CH=NOCH_2-C\equiv CH$ | 1,1-Dimethyl-2-propynyl |
| 1-Chloroethyl | $CH_2-CH=NOCH_2-C\equiv CH$ | 1,1-Dimethyl-2-propynyl |
| Methoxymethyl | $CH_2-CH=NOCH_2-C\equiv CH$ | 1,1-Dimethyl-2-propynyl |
| 1-Methylmethoxymethyl | $CH_2-CH=NOCH_2-C\equiv CH$ | 1,1-Dimethyl-2-propynyl |
| Ethenyl | $CH_2-CH=NOCH_2-C\equiv CH$ | 1,1-Dimethyl-2-propynyl |
| 1-Methylethenyl | $CH_2-CH=NOCH_2-C\equiv CH$ | 1,1-Dimethyl-2-propynyl |
| 2-Propenyl | $CH_2-CH=NOCH_2-C\equiv CH$ | 1,1-Dimethyl-2-propynyl |
| Methoxy | $CH_2-CH=NOCH_2-C\equiv CH$ | 1,1-Dimethyl-2-propynyl |
| Ethoxy | $CH_2-CH=NOCH_2-C\equiv CH$ | 1,1-Dimethyl-2-propynyl |
| 1,1-Dimethylethoxy | $CH_2-CH=NOCH_2-C\equiv CH$ | 1,1-Dimethyl-2-propynyl |
| Furanyl | $CH_2-CH=NOCH_2-C\equiv CH$ | 1,1-Dimethyl-2-propynyl |
| Thienyl | $CH_2-CH=NOCH_2-C\equiv CH$ | 1,1-Dimethyl-2-propynyl |
| 3-Methyl-isoxazol-5-yl | $CH_2-CH=NOCH_2-C\equiv CH$ | 1,1-Dimethyl-2-propynyl |
| 3-Ethyl-isoxazol-5-yl | $CH_2-CH=NOCH_2-C\equiv CH$ | 1,1-Dimethyl-2-propynyl |
| 3-(1-Methylethyl)-isoxazol-5-yl | $CH_2-CH=NOCH_2-C\equiv CH$ | 1,1-Dimethyl-2-propynyl |
| 5-Methyl-isoxazol-3-yl | $CH_2-CH=NOCH_2-C\equiv CH$ | 1,1-Dimethyl-2-propynyl |
| Phenyl | $CH_2-CH=NOCH_2-C\equiv CH$ | 1,1-Dimethyl-2-propynyl |
| 4-Fluorophenyl | $CH_2-CH=NOCH_2-C\equiv CH$ | 1,1-Dimethyl-2-propynyl |
| 4-Chlorophenyl | $CH_2-CH=NOCH_2-C\equiv CH$ | 1,1-Dimethyl-2-propynyl |
| 2,4-Dichlorophenyl | $CH_2-CH=NOCH_2-C\equiv CH$ | 1,1-Dimethyl-2-propynyl |
| H | $CH_2-CH=NOCH_2-C\equiv CH$ | Cyclopropyl |
| Methyl | $CH_2-CH=NOCH_2-C\equiv CH$ | Cyclopropyl |
| Ethyl | $CH_2-CH=NOCH_2-C\equiv CH$ | Cyclopropyl |
| Propyl | $CH_2-CH=NOCH_2-C\equiv CH$ | Cyclopropyl |
| 1-Methylethyl | $CH_2-CH=NOCH_2-C\equiv CH$ | Cyclopropyl |
| 1-Methylpropyl | $CH_2-CH=NOCH_2-C\equiv CH$ | Cyclopropyl |
| 1,1-Dimethylethyl | $CH_2-CH=NOCH_2-C\equiv CH$ | Cyclopropyl |
| Cyclopropyl | $CH_2-CH=NOCH_2-C\equiv CH$ | Cyclopropyl |
| Cyclopentyl | $CH_2-CH=NOCH_2-C\equiv CH$ | Cyclopropyl |
| Cyclohexyl | $CH_2-CH=NOCH_2-C\equiv CH$ | Cyclopropyl |
| 1-Methylcyclopropyl | $CH_2-CH=NOCH_2-C\equiv CH$ | Cyclopropyl |
| Cyclopropylmethyl | $CH_2-CH=NOCH_2-C\equiv CH$ | Cyclopropyl |
| 1-Cyclopropylethyl | $CH_2-CH=NOCH_2-C\equiv CH$ | Cyclopropyl |
| Chloromethyl | $CH_2-CH=NOCH_2-C\equiv CH$ | Cyclopropyl |
| 1-Chloroethyl | $CH_2-CH=NOCH_2-C\equiv CH$ | Cyclopropyl |
| Methoxymethyl | $CH_2-CH=NOCH_2-C\equiv CH$ | Cyclopropyl |
| 1-Methylmethoxymethyl | $CH_2-CH=NOCH_2-C\equiv CH$ | Cyclopropyl |
| Ethenyl | $CH_2-CH=NOCH_2-C\equiv CH$ | Cyclopropyl |
| 1-Methylethenyl | $CH_2-CH=NOCH_2-C\equiv CH$ | Cyclopropyl |

-continued $$\begin{array}{c} R^1 \diagdown \quad \diagup COOR^5 \\ \| \quad \| \\ N \diagdown_O \diagup CONHR^4 \end{array} \quad I$$

| R¹ | R⁵ | R⁴ |
|---|---|---|
| 2-Propenyl | CH₂—CH=NOCH₂—C≡CH | Cyclopropyl |
| Methoxy | CH₂—CH=NOCH₂—C≡CH | Cyclopropyl |
| Ethoxy | CH₂—CH=NOCH₂—C≡CH | Cyclopropyl |
| 1,1-Dimethylethoxy | CH₂—CH=NOCH₂—C≡CH | Cyclopropyl |
| Furanyl | CH₂—CH=NOCH₂—C≡CH | Cyclopropyl |
| Thienyl | CH₂—CH=NOCH₂—C≡CH | Cyclopropyl |
| 3-Methyl-isoxazol-5-yl | CH₂—CH=NOCH₂—C≡CH | Cyclopropyl |
| 3-Ethyl-isoxazol-5-yl | CH₂—CH=NOCH₂—C≡CH | Cyclopropyl |
| 3-(1-Methylethyl)-isoxazol-5-yl | CH₂—CH=NOCH₂—C≡CH | Cyclopropyl |
| 5-Methyl-isoxazol-3-yl | CH₂—CH=NOCH₂—C≡CH | Cyclopropyl |
| Phenyl | CH₂—CH=NOCH₂—C≡CH | Cyclopropyl |
| 4-Fluorophenyl | CH₂—CH=NOCH₂—C≡CH | Cyclopropyl |
| 4-Chlorophenyl | CH₂—CH=NOCH₂—C≡CH | Cyclopropyl |
| 2,4-Dichlorophenyl | CH₂—CH=NOCH₂—C≡CH | Cyclopropyl |
| H | CH₂—CH=NO(CH₂)₂—CH=CH—C₆H₄—F | 1,1-Dimethylethyl |
| Methyl | CH₂—CH=NO(CH₂)₂—CH=CH—C₆H₄—F | 1,1-Dimethylethyl |
| Ethyl | CH₂—CH=NO(CH₂)₂—CH=CH—C₆H₄—F | 1,1-Dimethylethyl |
| Propyl | CH₂—CH=NO(CH₂)₂—CH=CH—C₆H₄—F | 1,1-Dimethylethyl |
| 1-Methylethyl | CH₂—CH=NO(CH₂)₂—CH=CH—C₆H₄—F | 1,1-Dimethylethyl |
| 1-Methylpropyl | CH₂—CH=NO(CH₂)₂—CH=CH—C₆H₄—F | 1,1-Dimethylethyl |
| 1,1-Dimethylethyl | CH₂—CH=NO(CH₂)₂—CH=CH—C₆H₄—F | 1,1-Dimethylethyl |
| Cyclopropyl | CH₂—CH=NO(CH₂)₂—CH=CH—C₆H₄—F | 1,1-Dimethylethyl |
| Cyclopentyl | CH₂—CH=NO(CH₂)₂—CH=CH—C₆H₄—F | 1,1-Dimethylethyl |
| Cyclohexyl | CH₂—CH=NO(CH₂)₂—CH=CH—C₆H₄—F | 1,1-Dimethylethyl |
| 1-Methylcyclopropyl | CH₂—CH=NO(CH₂)₂—CH=CH—C₆H₄—F | 1,1-Dimethylethyl |
| Cyclopropylmethyl | CH₂—CH=NO(CH₂)₂—CH=CH—C₆H₄—F | 1,1-Dimethylethyl |
| 1-Cyclopropylethyl | CH₂—CH=NO(CH₂)₂—CH=CH—C₆H₄—F | 1,1-Dimethylethyl |
| Chloromethyl | CH₂—CH=NO(CH₂)₂—CH=CH—C₆H₄—F | 1,1-Dimethylethyl |
| 1-Chloroethyl | CH₂—CH=NO(CH₂)₂—CH=CH—C₆H₄—F | 1,1-Dimethylethyl |

-continued $$\underset{N\diagdown O}{\overset{R^1}{\|}}\!\!\!\!\!\!\!\!\!\!\!\!\!\!\!\!\!\!\!\!\!\!\!\!\!\!\!\!\!\!\!\!\overset{COOR^5}{\underset{CONHR^4}{}}$$  I

| R¹ | R⁵ | R⁴ |
|---|---|---|
| Methoxymethyl | CH₂—CH=NO(CH₂)₂—CH=CH—C₆H₄—F | 1,1-Dimethylethyl |
| 1-Methylmethoxymethyl | CH₂—CH=NO(CH₂)₂—CH=CH—C₆H₄—F | 1,1-Dimethylethyl |
| Ethenyl | CH₂—CH=NO(CH₂)₂—CH=CH—C₆H₄—F | 1,1-Dimethylethyl |
| 1-Methylethenyl | CH₂—CH=NO(CH₂)₂—CH=CH—C₆H₄—F | 1,1-Dimethylethyl |
| 2-Propenyl | CH₂—CH=NO(CH₂)₂—CH=CH—C₆H₄—F | 1,1-Dimethylethyl |
| Methoxy | CH₂—CH=NO(CH₂)₂—CH=CH—C₆H₄—F | 1,1-Dimethylethyl |
| Ethoxy | CH₂—CH=NO(CH₂)₂—CH=CH—C₆H₄—F | 1,1-Dimethylethyl |
| 1,1-Dimethylethoxy | CH₂—CH=NO(CH₂)₂—CH=CH—C₆H₄—F | 1,1-Dimethylethyl |
| Furanyl | CH₂—CH=NO(CH₂)₂—CH=CH—C₆H₄—F | 1,1-Dimethylethyl |
| Thienyl | CH₂—CH=NO(CH₂)₂—CH=CH—C₆H₄—F | 1,1-Dimethylethyl |
| 3-Methyl-isoxazol-5-yl | CH₂—CH=NO(CH₂)₂—CH=CH—C₆H₄—F | 1,1-Dimethylethyl |
| 3-Ethyl-isoxazol-5-yl | CH₂—CH=NO(CH₂)₂—CH=CH—C₆H₄—F | 1,1-Dimethylethyl |
| 3-(1-Methylethyl)-isoxazol-5-yl | CH₂—CH=NO(CH₂)₂—CH=CH—C₆H₄—F | 1,1-Dimethylethyl |
| 5-Methyl-isoxazol-3-yl | CH₂—CH=NO(CH₂)₂—CH=CH—C₆H₄—F | 1,1-Dimethylethyl |
| Phenyl | CH₂—CH=NO(CH₂)₂—CH=CH—C₆H₄—F | 1,1-Dimethylethyl |
| 4-Fluorophenyl | CH₂—CH=NO(CH₂)₂—CH=CH—C₆H₄—F | 1,1-Dimethylethyl |
| 4-Chlorophenyl | CH₂—CH=NO(CH₂)₂—CH=CH—C₆H₄—F | 1,1-Dimethylethyl |
| 2,4-Dichlorophenyl | CH₂—CH=NO(CH₂)₂—CH=CH—C₆H₄—F | 1,1-Dimethylethyl |
| H | CH₂—CH=NO(CH₂)₂—CH=CH—C₆H₄—F | 1,1-Dimethyl-2-propynyl |

-continued $$\begin{array}{c} R^1 \quad COOR^5 \\ \| \\ N\diagdown_O \diagdown CONHR^4 \end{array} \qquad I$$

| R¹ | R⁵ | R⁴ |
|---|---|---|
| Methyl | CH₂—CH=NO(CH₂)₂—CH=CH—⟨C₆H₄⟩—F | 1,1-Dimethyl-2-propynyl |
| Ethyl | CH₂—CH=NO(CH₂)₂—CH=CH—⟨C₆H₄⟩—F | 1,1-Dimethyl-2-propynyl |
| Propyl | CH₂—CH=NO(CH₂)₂—CH=CH—⟨C₆H₄⟩—F | 1,1-Dimethyl-2-propynyl |
| 1-Methylethyl | CH₂—CH=NO(CH₂)₂—CH=CH—⟨C₆H₄⟩—F | 1,1-Dimethyl-2-propynyl |
| 1-Methylpropyl | CH₂—CH=NO(CH₂)₂—CH=CH—⟨C₆H₄⟩—F | 1,1-Dimethyl-2-propynyl |
| 1,1-Dimethylethyl | CH₂—CH=NO(CH₂)₂—CH=CH—⟨C₆H₄⟩—F | 1,1-Dimethyl-2-propynyl |
| Cyclopropyl | CH₂—CH=NO(CH₂)₂—CH=CH—⟨C₆H₄⟩—F | 1,1-Dimethyl-2-propynyl |
| Cyclopentyl | CH₂—CH=NO(CH₂)₂—CH=CH—⟨C₆H₄⟩—F | 1,1-Dimethyl-2-propynyl |
| Cyclohexyl | CH₂—CH=NO(CH₂)₂—CH=CH—⟨C₆H₄⟩—F | 1,1-Dimethyl-2-propynyl |
| 1-Methylcyclopropyl | CH₂—CH=NO(CH₂)₂—CH=CH—⟨C₆H₄⟩—F | 1,1-Dimethyl-2-propynyl |
| Cyclopropylmethyl | CH₂—CH=NO(CH₂)₂—CH=CH—⟨C₆H₄⟩—F | 1,1-Dimethyl-2-propynyl |
| 1-Cyclopropylethyl | CH₂—CH=NO(CH₂)₂—CH=CH—⟨C₆H₄⟩—F | 1,1-Dimethyl-2-propynyl |
| Chloromethyl | CH₂—CH=NO(CH₂)₂—CH=CH—⟨C₆H₄⟩—F | 1,1-Dimethyl-2-propynyl |
| 1-Chloroethyl | CH₂—CH=NO(CH₂)₂—CH=CH—⟨C₆H₄⟩—F | 1,1-Dimethyl-2-propynyl |
| Methoxymethyl | CH₂—CH=NO(CH₂)₂—CH=CH—⟨C₆H₄⟩—F | 1,1-Dimethyl-2-propynyl |
| 1-Methylmethoxymethyl | CH₂—CH=NO(CH₂)₂—CH=CH—⟨C₆H₄⟩—F | 1,1-Dimethyl-2-propynyl |
| Ethenyl | CH₂—CH=NO(CH₂)₂—CH=CH—⟨C₆H₄⟩—F | 1,1-Dimethyl-2-propynyl |
| 1-Methylethenyl | CH₂—CH=NO(CH₂)₂—CH=CH—⟨C₆H₄⟩—F | 1,1-Dimethyl-2-propynyl |

-continued $$\begin{array}{c} R^1 \quad COOR^5 \\ \diagdown \diagup \\ \| \\ N \\ \diagdown O \diagup CONHR^4 \end{array} \qquad I$$

| R¹ | R⁵ | R⁴ |
|---|---|---|
| 2-Propenyl | CH₂—CH=NO(CH₂)₂—CH=CH—⟨C₆H₄⟩—F | 1,1-Dimethyl-2-propynyl |
| Methoxy | CH₂—CH=NO(CH₂)₂—CH=CH—⟨C₆H₄⟩—F | 1,1-Dimethyl-2-propynyl |
| Ethoxy | CH₂—CH=NO(CH₂)₂—CH=CH—⟨C₆H₄⟩—F | 1,1-Dimethyl-2-propynyl |
| 1,1-Dimethylethoxy | CH₂—CH=NO(CH₂)₂—CH=CH—⟨C₆H₄⟩—F | 1,1-Dimethyl-2-propynyl |
| Furanyl | CH₂—CH=NO(CH₂)₂—CH=CH—⟨C₆H₄⟩—F | 1,1-Dimethyl-2-propynyl |
| Thienyl | CH₂—CH=NO(CH₂)₂—CH=CH—⟨C₆H₄⟩—F | 1,1-Dimethyl-2-propynyl |
| 3-Methyl-isoxazol-5-yl | CH₂—CH=NO(CH₂)₂—CH=CH—⟨C₆H₄⟩—F | 1,1-Dimethyl-2-propynyl |
| 3-Ethyl-isoxazol-5-yl | CH₂—CH=NO(CH₂)₂—CH=CH—⟨C₆H₄⟩—F | 1,1-Dimethyl-2-propynyl |
| 3-(1-Methylethyl)-isoxazol-5-yl | CH₂—CH=NO(CH₂)₂—CH=CH—⟨C₆H₄⟩—F | 1,1-Dimethyl-2-propynyl |
| 5-Methyl-isoxazol-3-yl | CH₂—CH=NO(CH₂)₂—CH=CH—⟨C₆H₄⟩—F | 1,1-Dimethyl-2-propynyl |
| Phenyl | CH₂—CH=NO(CH₂)₂—CH=CH—⟨C₆H₄⟩—F | 1,1-Dimethyl-2-propynyl |
| 4-Fluorophenyl | CH₂—CH=NO(CH₂)₂—CH=CH—⟨C₆H₄⟩—F | 1,1-Dimethyl-2-propynyl |
| 4-Chlorophenyl | CH₂—CH=NO(CH₂)₂—CH=CH—⟨C₆H₄⟩—F | 1,1-Dimethyl-2-propynyl |
| 2,4-Dichlorophenyl | CH₂—CH=NO(CH₂)₂—CH=CH—⟨C₆H₄⟩—F | 1,1-Dimethyl-2-propynyl |
| H | CH₂—CH=NO(CH₂)₂—CH=CH—⟨C₆H₄⟩—F | Cyclopropyl |
| Methyl | CH₂—CH=NO(CH₂)₂—CH=CH—⟨C₆H₄⟩—F | Cyclopropyl |
| Ethyl | CH₂—CH=NO(CH₂)₂—CH=CH—⟨C₆H₄⟩—F | Cyclopropyl |
| Propyl | CH₂—CH=NO(CH₂)₂—CH=CH—⟨C₆H₄⟩—F | Cyclopropyl |
| 1-Methylethyl | CH₂—CH=NO(CH₂)₂—CH=CH—⟨C₆H₄⟩—F | Cyclopropyl |

-continued $$\text{I}$$

Structure: isoxazole ring with R¹ at 3-position, COOR⁵ at 4-position, CONHR⁴ at 5-position.

| R¹ | R⁵ | R⁴ |
|---|---|---|
| 1-Methylpropyl | CH$_2$—CH=NO(CH$_2$)$_2$—CH=CH—C$_6$H$_4$—F | Cyclopropyl |
| 1,1-Dimethylethyl | CH$_2$—CH=NO(CH$_2$)$_2$—CH=CH—C$_6$H$_4$—F | Cyclopropyl |
| Cyclopropyl | CH$_2$—CH=NO(CH$_2$)$_2$—CH=CH—C$_6$H$_4$—F | Cyclopropyl |
| Cyclopentyl | CH$_2$—CH=NO(CH$_2$)$_2$—CH=CH—C$_6$H$_4$—F | Cyclopropyl |
| Cyclohexyl | CH$_2$—CH=NO(CH$_2$)$_2$—CH=CH—C$_6$H$_4$—F | Cyclopropyl |
| 1-Methylcyclopropyl | CH$_2$—CH=NO(CH$_2$)$_2$—CH=CH—C$_6$H$_4$—F | Cyclopropyl |
| Cyclopropylmethyl | CH$_2$—CH=NO(CH$_2$)$_2$—CH=CH—C$_6$H$_4$—F | Cyclopropyl |
| 1-Cyclopropylethyl | CH$_2$—CH=NO(CH$_2$)$_2$—CH=CH—C$_6$H$_4$—F | Cyclopropyl |
| Chloromethyl | CH$_2$—CH=NO(CH$_2$)$_2$—CH=CH—C$_6$H$_4$—F | Cyclopropyl |
| 1-Chloroethyl | CH$_2$—CH=NO(CH$_2$)$_2$—CH=CH—C$_6$H$_4$—F | Cyclopropyl |
| Methoxymethyl | CH$_2$—CH=NO(CH$_2$)$_2$—CH=CH—C$_6$H$_4$—F | Cyclopropyl |
| 1-Methylmethoxymethyl | CH$_2$—CH=NO(CH$_2$)$_2$—CH=CH—C$_6$H$_4$—F | Cyclopropyl |
| Ethenyl | CH$_2$—CH=NO(CH$_2$)$_2$—CH=CH—C$_6$H$_4$—F | Cyclopropyl |
| 1-Methylethenyl | CH$_2$—CH=NO(CH$_2$)$_2$—CH=CH—C$_6$H$_4$—F | Cyclopropyl |
| 2-Propenyl | CH$_2$—CH=NO(CH$_2$)$_2$—CH=CH—C$_6$H$_4$—F | Cyclopropyl |
| Methoxy | CH$_2$—CH=NO(CH$_2$)$_2$—CH=CH—C$_6$H$_4$—F | Cyclopropyl |
| Ethoxy | CH$_2$—CH=NO(CH$_2$)$_2$—CH=CH—C$_6$H$_4$—F | Cyclopropyl |
| 1,1-Dimethylethoxy | CH$_2$—CH=NO(CH$_2$)$_2$—CH=CH—C$_6$H$_4$—F | Cyclopropyl |

-continued $$\begin{array}{c} R^1 \\ \parallel \\ N_{\diagdown O} \end{array} \begin{array}{c} COOR^5 \\ CONHR^4 \end{array} \qquad I$$

| R¹ | R⁵ | R⁴ |
|---|---|---|
| Furanyl | CH₂—CH=NO(CH₂)₂—CH=CH—C₆H₄—F | Cyclopropyl |
| Thienyl | CH₂—CH=NO(CH₂)₂—CH=CH—C₆H₄—F | Cyclopropyl |
| 3-Methyl-isoxazol-5-yl | CH₂—CH=NO(CH₂)₂—CH=CH—C₆H₄—F | Cyclopropyl |
| 3-Ethyl-isoxazol-5-yl | CH₂—CH=NO(CH₂)₂—CH=CH—C₆H₄—F | Cyclopropyl |
| 3-(1-Methylethyl)-isoxazol-5-yl | CH₂—CH=NO(CH₂)₂—CH=CH—C₆H₄—F | Cyclopropyl |
| 5-Methyl-isoxazol-3-yl | CH₂—CH=NO(CH₂)₂—CH=CH—C₆H₄—F | Cyclopropyl |
| Phenyl | CH₂—CH=NO(CH₂)₂—CH=CH—C₆H₄—F | Cyclopropyl |
| 4-Fluorophenyl | CH₂—CH=NO(CH₂)₂—CH=CH—C₆H₄—F | Cyclopropyl |
| 4-Chlorophenyl | CH₂—CH=NO(CH₂)₂—CH=CH—C₆H₄—F | Cyclopropyl |
| 2,4-Dichlorophenyl | CH₂—CH=NO(CH₂)₂—CH=CH—C₆H₄—F | Cyclopropyl |
| H | CH₂—CH=NO—C₆H₅ | 1,1-Dimethylethyl |
| Methyl | CH₂—CH=NO—C₆H₅ | 1,1-Dimethylethyl |
| Ethyl | CH₂—CH=NO—C₆H₅ | 1,1-Dimethylethyl |
| Propyl | CH₂—CH=NO—C₆H₅ | 1,1-Dimethylethyl |
| 1-Methylethyl | CH₂—CH=NO—C₆H₅ | 1,1-Dimethylethyl |
| 1-Methylpropyl | CH₂—CH=NO—C₆H₅ | 1,1-Dimethylethyl |
| 1,1-Dimethylethyl | CH₂—CH=NO—C₆H₅ | 1,1-Dimethylethyl |
| Cyclopropyl | CH₂—CH=NO—C₆H₅ | 1,1-Dimethylethyl |
| Cyclopentyl | CH₂—CH=NO—C₆H₅ | 1,1-Dimethylethyl |
| Cyclohexyl | CH₂—CH=NO—C₆H₅ | 1,1-Dimethylethyl |
| 1-Methylcyclopropyl | CH₂—CH=NO—C₆H₅ | 1,1-Dimethylethyl |
| Cyclopropylmethyl | CH₂—CH=NO—C₆H₅ | 1,1-Dimethylethyl |
| 1-Cyclopropylethyl | CH₂—CH=NO—C₆H₅ | 1,1-Dimethylethyl |
| Chloromethyl | CH₂—CH=NO—C₆H₅ | 1,1-Dimethylethyl |
| 1-Chloroethyl | CH₂—CH=NO—C₆H₅ | 1,1-Dimethylethyl |
| Methoxymethyl | CH₂—CH=NO—C₆H₅ | 1,1-Dimethylethyl |
| 1-Methylmethoxymethyl | CH₂—CH=NO—C₆H₅ | 1,1-Dimethylethyl |
| Ethenyl | CH₂—CH=NO—C₆H₅ | 1,1-Dimethylethyl |
| 1-Methylethenyl | CH₂—CH=NO—C₆H₅ | 1,1-Dimethylethyl |
| 2-Propenyl | CH₂—CH=NO—C₆H₅ | 1,1-Dimethylethyl |
| Methoxy | CH₂—CH=NO—C₆H₅ | 1,1-Dimethylethyl |
| Ethoxy | CH₂—CH=NO—C₆H₅ | 1,1-Dimethylethyl |
| 1,1-Dimethylethoxy | CH₂—CH=NO—C₆H₅ | 1,1-Dimethylethyl |
| Furanyl | CH₂—CH=NO—C₆H₅ | 1,1-Dimethylethyl |
| Thienyl | CH₂—CH=NO—C₆H₅ | 1,1-Dimethylethyl |
| 3-Methyl-isoxazol-5-yl | CH₂—CH=NO—C₆H₅ | 1,1-Dimethylethyl |
| 3-Ethyl-isoxazol-5-yl | CH₂—CH=NO—C₆H₅ | 1,1-Dimethylethyl |
| 3-(1-Methylethyl)-isoxazol-5-yl | CH₂—CH=NO—C₆H₅ | 1,1-Dimethylethyl |
| 5-Methyl-isoxazol-3-yl | CH₂—CH=NO—C₆H₅ | 1,1-Dimethylethyl |
| Phenyl | CH₂—CH=NO—C₆H₅ | 1,1-Dimethylethyl |
| 4-Fluorophenyl | CH₂—CH=NO—C₆H₅ | 1,1-Dimethylethyl |
| 4-Chlorophenyl | CH₂—CH=NO—C₆H₅ | 1,1-Dimethylethyl |
| 2,4-Dichlorophenyl | CH₂—CH=NO—C₆H₅ | 1,1-Dimethylethyl |
| H | CH₂—CH=NO—C₆H₅ | 1,1-Dimethyl-2-propynyl |
| Methyl | CH₂—CH=NO—C₆H₅ | 1,1-Dimethyl-2-propynyl |

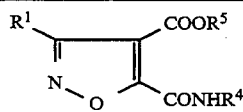

| R¹ | R⁵ | R⁴ |
|---|---|---|
| Ethyl | $CH_2-CH=NO-C_6H_5$ | 1,1-Dimethyl-2-propynyl |
| Propyl | $CH_2-CH=NO-C_6H_5$ | 1,1-Dimethyl-2-propynyl |
| 1-Methylethyl | $CH_2-CH=NO-C_6H_5$ | 1,1-Dimethyl-2-propynyl |
| 1-Methylpropyl | $CH_2-CH=NO-C_6H_5$ | 1,1-Dimethyl-2-propynyl |
| 1,1-Dimethylethyl | $CH_2-CH=NO-C_6H_5$ | 1,1-Dimethyl-2-propynyl |
| Cyclopropyl | $CH_2-CH=NO-C_6H_5$ | 1,1-Dimethyl-2-propynyl |
| Cyclopentyl | $CH_2-CH=NO-C_6H_5$ | 1,1-Dimethyl-2-propynyl |
| Cyclohexyl | $CH_2-CH=NO-C_6H_5$ | 1,1-Dimethyl-2-propynyl |
| 1-Methylcyclopropyl | $CH_2-CH=NO-C_6H_5$ | 1,1-Dimethyl-2-propynyl |
| Cyclopropylmethyl | $CH_2-CH=NO-C_6H_5$ | 1,1-Dimethyl-2-propynyl |
| 1-Cyclopropylethyl | $CH_2-CH=NO-C_6H_5$ | 1,1-Dimethyl-2-propynyl |
| Chloromethyl | $CH_2-CH=NO-C_6H_5$ | 1,1-Dimethyl-2-propynyl |
| 1-Chloroethyl | $CH_2-CH=NO-C_6H_5$ | 1,1-Dimethyl-2-propynyl |
| Methoxymethyl | $CH_2-CH=NO-C_6H_5$ | 1,1-Dimethyl-2-propynyl |
| 1-Methylmethoxymethyl | $CH_2-CH=NO-C_6H_5$ | 1,1-Dimethyl-2-propynyl |
| Ethenyl | $CH_2-CH=NO-C_6H_5$ | 1,1-Dimethyl-2-propynyl |
| 1-Methylethenyl | $CH_2-CH=NO-C_6H_5$ | 1,1-Dimethyl-2-propynyl |
| 2-Propenyl | $CH_2-CH=NO-C_6H_5$ | 1,1-Dimethyl-2-propynyl |
| Methoxy | $CH_2-CH=NO-C_6H_5$ | 1,1-Dimethyl-2-propynyl |
| Ethoxy | $CH_2-CH=NO-C_6H_5$ | 1,1-Dimethyl-2-propynyl |
| 1,1-Dimethylethoxy | $CH_2-CH=NO-C_6H_5$ | 1,1-Dimethyl-2-propynyl |
| Furanyl | $CH_2-CH=NO-C_6H_5$ | 1,1-Dimethyl-2-propynyl |
| Thienyl | $CH_2-CH=NO-C_6H_5$ | 1,1-Dimethyl-2-propynyl |
| 3-Methyl-isoxazol-5-yl | $CH_2-CH=NO-C_6H_5$ | 1,1-Dimethyl-2-propynyl |
| 3-Ethyl-isoxazol-5-yl | $CH_2-CH=NO-C_6H_5$ | 1,1-Dimethyl-2-propynyl |
| 3-(1-Methylethyl)-isoxazol-5-yl | $CH_2-CH=NO-C_6H_5$ | 1,1-Dimethyl-2-propynyl |
| 5-Methyl-isoxazol-3-yl | $CH_2-CH=NO-C_6H_5$ | 1,1-Dimethyl-2-propynyl |
| Phenyl | $CH_2-CH=NO-C_6H_5$ | 1,1-Dimethyl-2-propynyl |
| 4-Fluorophenyl | $CH_2-CH=NO-C_6H_5$ | 1,1-Dimethyl-2-propynyl |
| 4-Chlorophenyl | $CH_2-CH=NO-C_6H_5$ | 1,1-Dimethyl-2-propynyl |
| 2,4-Dichlorophenyl | $CH_2-CH=NO-C_6H_5$ | 1,1-Dimethyl-2-propynyl |
| H | $CH_2-CH=NO-C_6H_5$ | Cyclopropyl |
| Methyl | $CH_2-CH=NO-C_6H_5$ | Cyclopropyl |
| Ethyl | $CH_2-CH=NO-C_6H_5$ | Cyclopropyl |
| Propyl | $CH_2-CH=NO-C_6H_5$ | Cyclopropyl |
| 1-Methylethyl | $CH_2-CH=NO-C_6H_5$ | Cyclopropyl |
| 1-Methylpropyl | $CH_2-CH=NO-C_6H_5$ | Cyclopropyl |
| 1,1-Dimethylethyl | $CH_2-CH=NO-C_6H_5$ | Cyclopropyl |
| Cyclopropyl | $CH_2-CH=NO-C_6H_5$ | Cyclopropyl |
| Cyclopentyl | $CH_2-CH=NO-C_6H_5$ | Cyclopropyl |
| Cyclohexyl | $CH_2-CH=NO-C_6H_5$ | Cyclopropyl |
| 1-Methylcyclopropyl | $CH_2-CH=NO-C_6H_5$ | Cyclopropyl |
| Cyclopropylmethyl | $CH_2-CH=NO-C_6H_5$ | Cyclopropyl |
| 1-Cyclopropylethyl | $CH_2-CH=NO-C_6H_5$ | Cyclopropyl |
| Chloromethyl | $CH_2-CH=NO-C_6H_5$ | Cyclopropyl |
| 1-Chloroethyl | $CH_2-CH=NO-C_6H_5$ | Cyclopropyl |
| Methoxymethyl | $CH_2-CH=NO-C_6H_5$ | Cyclopropyl |
| 1-Methylmethoxymethyl | $CH_2-CH=NO-C_6H_5$ | Cyclopropyl |
| Ethenyl | $CH_2-CH=NO-C_6H_5$ | Cyclopropyl |
| 1-Methylethenyl | $CH_2-CH=NO-C_6H_5$ | Cyclopropyl |
| 2-Propenyl | $CH_2-CH=NO-C_6H_5$ | Cyclopropyl |
| Methoxy | $CH_2-CH=NO-C_6H_5$ | Cyclopropyl |
| Ethoxy | $CH_2-CH=NO-C_6H_5$ | Cyclopropyl |
| 1,1-Dimethylethoxy | $CH_2-CH=NO-C_6H_5$ | Cyclopropyl |
| Furanyl | $CH_2-CH=NO-C_6H_5$ | Cyclopropyl |
| Thienyl | $CH_2-CH=NO-C_6H_5$ | Cyclopropyl |
| 3-Methyl-isoxazol-5-yl | $CH_2-CH=NO-C_6H_5$ | Cyclopropyl |
| 3-Ethyl-isoxazol-5-yl | $CH_2-CH=NO-C_6H_5$ | Cyclopropyl |
| 3-(1-Methylethyl)-isoxazol-5-yl | $CH_2-CH=NO-C_6H_5$ | Cyclopropyl |
| 5-Methyl-isoxazol-3-yl | $CH_2-CH=NO-C_6H_5$ | Cyclopropyl |
| Phenyl | $CH_2-CH=NO-C_6H_5$ | Cyclopropyl |
| 4-Fluorophenyl | $CH_2-CH=NO-C_6H_5$ | Cyclopropyl |
| 4-Chlorophenyl | $CH_2-CH=NO-C_6H_5$ | Cyclopropyl |
| 2,4-Dichlorophenyl | $CH_2-CH=NO-C_6H_5$ | Cyclopropyl |
| H | $CH_2-CH=N-N-CH_3$ | 1,1-Dimethylethyl |
| Methyl | $CH_2-CH=N-N-CH_3$ | 1,1-Dimethylethyl |
| Ethyl | $CH_2-CH=N-N-CH_3$ | 1,1-Dimethylethyl |
| Propyl | $CH_2-CH=N-N-CH_3$ | 1,1-Dimethylethyl |
| 1-Methylethyl | $CH_2-CH=N-N-CH_3$ | 1,1-Dimethylethyl |
| 1-Methylpropyl | $CH_2-CH=N-N-CH_3$ | 1,1-Dimethylethyl |
| 1,1-Dimethylethyl | $CH_2-CH=N-N-CH_3$ | 1,1-Dimethylethyl |
| Cyclopropyl | $CH_2-CH=N-N-CH_3$ | 1,1-Dimethylethyl |
| Cyclopentyl | $CH_2-CH=N-N-CH_3$ | 1,1-Dimethylethyl |
| Cyclohexyl | $CH_2-CH=N-N-CH_3$ | 1,1-Dimethylethyl |
| 1-Methylcyclopropyl | $CH_2-CH=N-N-CH_3$ | 1,1-Dimethylethyl |

-continued

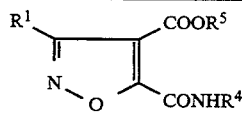 I

| R¹ | R⁵ | R⁴ |
|---|---|---|
| Cyclopropylmethyl | $CH_2-CH=N-N-CH_3$ | 1,1-Dimethylethyl |
| 1-Cyclopropylethyl | $CH_2-CH=N-N-CH_3$ | 1,1-Dimethylethyl |
| Chloromethyl | $CH_2-CH=N-N-CH_3$ | 1,1-Dimethylethyl |
| 1-Chloroethyl | $CH_2-CH=N-N-CH_3$ | 1,1-Dimethylethyl |
| Methoxymethyl | $CH_2-CH=N-N-CH_3$ | 1,1-Dimethylethyl |
| 1-Methylmethoxymethyl | $CH_2-CH=N-N-CH_3$ | 1,1-Dimethylethyl |
| Ethenyl | $CH_2-CH=N-N-CH_3$ | 1,1-Dimethylethyl |
| 1-Methylethenyl | $CH_2-CH=N-N-CH_3$ | 1,1-Dimethylethyl |
| 2-Propenyl | $CH_2-CH=N-N-CH_3$ | 1,1-Dimethylethyl |
| Methoxy | $CH_2-CH=N-N-CH_3$ | 1,1-Dimethylethyl |
| Ethoxy | $CH_2-CH=N-N-CH_3$ | 1,1-Dimethylethyl |
| 1,1-Dimethylethoxy | $CH_2-CH=N-N-CH_3$ | 1,1-Dimethylethyl |
| Furanyl | $CH_2-CH=N-N-CH_3$ | 1,1-Dimethylethyl |
| Thienyl | $CH_2-CH=N-N-CH_3$ | 1,1-Dimethylethyl |
| 3-Methyl-isoxazol-5-yl | $CH_2-CH=N-N-CH_3$ | 1,1-Dimethylethyl |
| 3-Ethyl-isoxazol-5-yl | $CH_2-CH=N-N-CH_3$ | 1,1-Dimethylethyl |
| 3-(1-Methylethyl)-isoxazol-5-yl | $CH_2-CH=N-N-CH_3$ | 1,1-Dimethylethyl |
| 5-Methyl-isoxazol-3-yl | $CH_2-CH=N-N-CH_3$ | 1,1-Dimethylethyl |
| Phenyl | $CH_2-CH=N-N-CH_3$ | 1,1-Dimethylethyl |
| 4-Fluorophenyl | $CH_2-CH=N-N-CH_3$ | 1,1-Dimethylethyl |
| 4-Chlorophenyl | $CH_2-CH=N-N-CH_3$ | 1,1-Dimethylethyl |
| 2,4-Dichlorophenyl | $CH_2-CH=N-N-CH_3$ | 1,1-Dimethylethyl |
| H | $CH_2-CH=N-N-CH_3$ | 1,1-Dimethyl-2-propynyl |
| Methyl | $CH_2-CH=N-N-CH_3$ | 1,1-Dimethyl-2-propynyl |
| Ethyl | $CH_2-CH=N-N-CH_3$ | 1,1-Dimethyl-2-propynyl |
| Propyl | $CH_2-CH=N-N-CH_3$ | 1,1-Dimethyl-2-propynyl |
| 1-Methylethyl | $CH_2-CH=N-N-CH_3$ | 1,1-Dimethyl-2-propynyl |
| 1-Methylpropyl | $CH_2-CH=N-N-CH_3$ | 1,1-Dimethyl-2-propynyl |
| 1,1-Dimethylethyl | $CH_2-CH=N-N-CH_3$ | 1,1-Dimethyl-2-propynyl |
| Cyclopropyl | $CH_2-CH=N-N-CH_3$ | 1,1-Dimethyl-2-propynyl |
| Cyclopentyl | $CH_2-CH=N-N-CH_3$ | 1,1-Dimethyl-2-propynyl |
| Cyclohexyl | $CH_2-CH=N-N-CH_3$ | 1,1-Dimethyl-2-propynyl |
| 1-Methylcyclopropyl | $CH_2-CH=N-N-CH_3$ | 1,1-Dimethyl-2-propynyl |
| Cyclopropylmethyl | $CH_2-CH=N-N-CH_3$ | 1,1-Dimethyl-2-propynyl |
| 1-Cyclopropylethyl | $CH_2-CH=N-N-CH_3$ | 1,1-Dimethyl-2-propynyl |
| Chloromethyl | $CH_2-CH=N-N-CH_3$ | 1,1-Dimethyl-2-propynyl |
| 1-Chloroethyl | $CH_2-CH=N-N-CH_3$ | 1,1-Dimethyl-2-propynyl |
| Methoxymethyl | $CH_2-CH=N-N-CH_3$ | 1,1-Dimethyl-2-propynyl |
| 1-Methylmethoxymethyl | $CH_2-CH=N-N-CH_3$ | 1,1-Dimethyl-2-propynyl |
| Ethenyl | $CH_2-CH=N-N-CH_3$ | 1,1-Dimethyl-2-propynyl |
| 1-Methylethenyl | $CH_2-CH=N-N-CH_3$ | 1,1-Dimethyl-2-propynyl |
| 2-Propenyl | $CH_2-CH=N-N-CH_3$ | 1,1-Dimethyl-2-propynyl |
| Methoxy | $CH_2-CH=N-N-CH_3$ | 1,1-Dimethyl-2-propynyl |
| Ethoxy | $CH_2-CH=N-N-CH_3$ | 1,1-Dimethyl-2-propynyl |
| 1,1-Dimethylethoxy | $CH_2-CH=N-N-CH_3$ | 1,1-Dimethyl-2-propynyl |
| Furanyl | $CH_2-CH=N-N-CH_3$ | 1,1-Dimethyl-2-propynyl |
| Thienyl | $CH_2-CH=N-N-CH_3$ | 1,1-Dimethyl-2-propynyl |
| 3-Methyl-isoxazol-5-yl | $CH_2-CH=N-N-CH_3$ | 1,1-Dimethyl-2-propynyl |
| 3-Ethyl-isoxazol-5-yl | $CH_2-CH=N-N-CH_3$ | 1,1-Dimethyl-2-propynyl |
| 3-(1-Methylethyl)-isoxazol-5-yl | $CH_2-CH=N-N-CH_3$ | 1,1-Dimethyl-2-propynyl |
| 5-Methyl-isoxazol-3-yl | $CH_2-CH=N-N-CH_3$ | 1,1-Dimethyl-2-propynyl |
| Phenyl | $CH_2-CH=N-N-CH_3$ | 1,1-Dimethyl-2-propynyl |
| 4-Fluorophenyl | $CH_2-CH=N-N-CH_3$ | 1,1-Dimethyl-2-propynyl |
| 4-Chlorophenyl | $CH_2-CH=N-N-CH_3$ | 1,1-Dimethyl-2-propynyl |
| 2,4-Dichlorophenyl | $CH_2-CH=N-N-CH_3$ | 1,1-Dimethyl-2-propynyl |
| H | $CH_2-CH=N-N-CH_3$ | Cyclopropyl |
| Methyl | $CH_2-CH=N-N-CH_3$ | Cyclopropyl |
| Ethyl | $CH_2-CH=N-N-CH_3$ | Cyclopropyl |
| Propyl | $CH_2-CH=N-N-CH_3$ | Cyclopropyl |
| 1-Methylethyl | $CH_2-CH=N-N-CH_3$ | Cyclopropyl |
| 1-Methylpropyl | $CH_2-CH=N-N-CH_3$ | Cyclopropyl |
| 1,1-Dimethylethyl | $CH_2-CH=N-N-CH_3$ | Cyclopropyl |
| Cyclopropyl | $CH_2-CH=N-N-CH_3$ | Cyclopropyl |
| Cyclopentyl | $CH_2-CH=N-N-CH_3$ | Cyclopropyl |
| Cyclohexyl | $CH_2-CH=N-N-CH_3$ | Cyclopropyl |
| 1-Methylcyclopropyl | $CH_2-CH=N-N-CH_3$ | Cyclopropyl |
| Cyclopropylmethyl | $CH_2-CH=N-N-CH_3$ | Cyclopropyl |
| 1-Cyclopropylethyl | $CH_2-CH=N-N-CH_3$ | Cyclopropyl |
| Chloromethyl | $CH_2-CH=N-N-CH_3$ | Cyclopropyl |
| 1-Chloroethyl | $CH_2-CH=N-N-CH_3$ | Cyclopropyl |
| Methoxymethyl | $CH_2-CH=N-N-CH_3$ | Cyclopropyl |
| 1-Methylmethoxymethyl | $CH_2-CH=N-N-CH_3$ | Cyclopropyl |
| Ethenyl | $CH_2-CH=N-N-CH_3$ | Cyclopropyl |
| 1-Methylethenyl | $CH_2-CH=N-N-CH_3$ | Cyclopropyl |
| 2-Propenyl | $CH_2-CH=N-N-CH_3$ | Cyclopropyl |

-continued $$\underset{N\diagdown O}{\overset{R^1}{\diagup}}\overset{COOR^5}{\underset{CONHR^4}{\diagdown}}\quad I$$

| R¹ | R⁵ | R⁴ |
|---|---|---|
| Methoxy | CH₂—CH=N—N—CH₃ | Cyclopropyl |
| Ethoxy | CH₂—CH=N—N—CH₃ | Cyclopropyl |
| 1,1-Dimethylethoxy | CH₂—CH=N—N—CH₃ | Cyclopropyl |
| Furanyl | CH₂—CH=N—N—CH₃ | Cyclopropyl |
| Thienyl | CH₂—CH=N—N—CH₃ | Cyclopropyl |
| 3-Methyl-isoxazol-5-yl | CH₂—CH=N—N—CH₃ | Cyclopropyl |
| 3-Ethyl-isoxazol-5-yl | CH₂—CH=N—N—CH₃ | Cyclopropyl |
| 3-(1-Methylethyl)-isoxazol-5-yl | CH₂—CH=N—N—CH₃ | Cyclopropyl |
| 5-Methyl-isoxazol-3-yl | CH₂—CH=N—N—CH₃ | Cyclopropyl |
| Phenyl | CH₂—CH=N—N—CH₃ | Cyclopropyl |
| 4-Fluorophenyl | CH₂—CH=N—N—CH₃ | Cyclopropyl |
| 4-Chlorophenyl | CH₂—CH=N—N—CH₃ | Cyclopropyl |
| 2,4-Dichlorophenyl | CH₂—CH=N—N—CH₃ | Cyclopropyl |
| H | CH₂—CH=N—N—C₆H₅ | 1,1-Dimethylethyl |
| Methyl | CH₂—CH=N—N—C₆H₅ | 1,1-Dimethylethyl |
| Ethyl | CH₂—CH=N—N—C₆H₅ | 1,1-Dimethylethyl |
| Propyl | CH₂—CH=N—N—C₆H₅ | 1,1-Dimethylethyl |
| 1-Methylethyl | CH₂—CH=N—N—C₆H₅ | 1,1-Dimethylethyl |
| 1-Methylpropyl | CH₂—CH=N—N—C₆H₅ | 1,1-Dimethylethyl |
| 1,1-Dimethylethyl | CH₂—CH=N—N—C₆H₅ | 1,1-Dimethylethyl |
| Cyclopropyl | CH₂—CH=N—N—C₆H₅ | 1,1-Dimethylethyl |
| Cyclopentyl | CH₂—CH=N—N—C₆H₅ | 1,1-Dimethylethyl |
| Cyclohexyl | CH₂—CH=N—N—C₆H₅ | 1,1-Dimethylethyl |
| 1-Methylcyclopropyl | CH₂—CH=N—N—C₆H₅ | 1,1-Dimethylethyl |
| Cyclopropylmethyl | CH₂—CH=N—N—C₆H₅ | 1,1-Dimethylethyl |
| 1-Cyclopropylethyl | CH₂—CH=N—N—C₆H₅ | 1,1-Dimethylethyl |
| Chloromethyl | CH₂—CH=N—N—C₆H₅ | 1,1-Dimethylethyl |
| 1-Chloroethyl | CH₂—CH=N—N—C₆H₅ | 1,1-Dimethylethyl |
| Methoxymethyl | CH₂—CH=N—N—C₆H₅ | 1,1-Dimethylethyl |
| 1-Methylmethoxymethyl | CH₂—CH=N—N—C₆H₅ | 1,1-Dimethylethyl |
| Ethenyl | CH₂—CH=N—N—C₆H₅ | 1,1-Dimethylethyl |
| 1-Methylethenyl | CH₂—CH=N—N—C₆H₅ | 1,1-Dimethylethyl |
| 2-Propenyl | CH₂—CH=N—N—C₆H₅ | 1,1-Dimethylethyl |
| Methoxy | CH₂—CH=N—N—C₆H₅ | 1,1-Dimethylethyl |
| Ethoxy | CH₂—CH=N—N—C₆H₅ | 1,1-Dimethylethyl |
| 1,1-Dimethylethoxy | CH₂—CH=N—N—C₆H₅ | 1,1-Dimethylethyl |
| Furanyl | CH₂—CH=N—N—C₆H₅ | 1,1-Dimethylethyl |
| Thienyl | CH₂—CH=N—N—C₆H₅ | 1,1-Dimethylethyl |
| 3-Methyl-isoxazol-5-yl | CH₂—CH=N—N—C₆H₅ | 1,1-Dimethylethyl |
| 3-Ethyl-isoxazol-5-yl | CH₂—CH=N—N—C₆H₅ | 1,1-Dimethylethyl |
| 3-(1-Methylethyl)-isoxazol-5-yl | CH₂—CH=N—N—C₆H₅ | 1,1-Dimethylethyl |
| 5-Methyl-isoxazol-3-yl | CH₂—CH=N—N—C₆H₅ | 1,1-Dimethylethyl |
| Phenyl | CH₂—CH=N—N—C₆H₅ | 1,1-Dimethylethyl |
| 4-Fluorophenyl | CH₂—CH=N—N—C₆H₅ | 1,1-Dimethylethyl |
| 4-Chlorophenyl | CH₂—CH=N—N—C₆H₅ | 1,1-Dimethylethyl |
| 2,4-Dichlorophenyl | CH₂—CH=N—N—C₆H₅ | 1,1-Dimethylethyl |
| H | CH₂—CH=N—N—C₆H₅ | 1,1-Dimethyl-2-propynyl |
| Methyl | CH₂—CH=N—N—C₆H₅ | 1,1-Dimethyl-2-propynyl |
| Ethyl | CH₂—CH=N—N—C₆H₅ | 1,1-Dimethyl-2-propynyl |
| Propyl | CH₂—CH=N—N—C₆H₅ | 1,1-Dimethyl-2-propynyl |
| 1-Methylethyl | CH₂—CH=N—N—C₆H₅ | 1,1-Dimethyl-2-propynyl |
| 1-Methylpropyl | CH₂—CH=N—N—C₆H₅ | 1,1-Dimethyl-2-propynyl |
| 1,1-Dimethylethyl | CH₂—CH=N—N—C₆H₅ | 1,1-Dimethyl-2-propynyl |
| Cyclopropyl | CH₂—CH=N—N—C₆H₅ | 1,1-Dimethyl-2-propynyl |
| Cyclopentyl | CH₂—CH=N—N—C₆H₅ | 1,1-Dimethyl-2-propynyl |
| Cyclohexyl | CH₂—CH=N—N—C₆H₅ | 1,1-Dimethyl-2-propynyl |
| 1-Methylcyclopropyl | CH₂—CH=N—N—C₆H₅ | 1,1-Dimethyl-2-propynyl |
| Cyclopropylmethyl | CH₂—CH=N—N—C₆H₅ | 1,1-Dimethyl-2-propynyl |
| 1-Cyclopropylethyl | CH₂—CH=N—N—C₆H₅ | 1,1-Dimethyl-2-propynyl |
| Chloromethyl | CH₂—CH=N—N—C₆H₅ | 1,1-Dimethyl-2-propynyl |
| 1-Chloroethyl | CH₂—CH=N—N—C₆H₅ | 1,1-Dimethyl-2-propynyl |
| Methoxymethyl | CH₂—CH=N—N—C₆H₅ | 1,1-Dimethyl-2-propynyl |
| 1-Methylmethoxymethyl | CH₂—CH=N—N—C₆H₅ | 1,1-Dimethyl-2-propynyl |
| Ethenyl | CH₂—CH=N—N—C₆H₅ | 1,1-Dimethyl-2-propynyl |
| 1-Methylethenyl | CH₂—CH=N—N—C₆H₅ | 1,1-Dimethyl-2-propynyl |
| 2-Propenyl | CH₂—CH=N—N—C₆H₅ | 1,1-Dimethyl-2-propynyl |
| Methoxy | CH₂—CH=N—N—C₆H₅ | 1,1-Dimethyl-2-propynyl |
| Ethoxy | CH₂—CH=N—N—C₆H₅ | 1,1-Dimethyl-2-propynyl |
| 1,1-Dimethylethoxy | CH₂—CH=N—N—C₆H₅ | 1,1-Dimethyl-2-propynyl |
| Furanyl | CH₂—CH=N—N—C₆H₅ | 1,1-Dimethyl-2-propynyl |
| Thienyl | CH₂—CH=N—N—C₆H₅ | 1,1-Dimethyl-2-propynyl |
| 3-Methyl-isoxazol-5-yl | CH₂—CH=N—N—C₆H₅ | 1,1-Dimethyl-2-propynyl |
| 3-Ethyl-isoxazol-5-yl | CH₂—CH=N—N—C₆H₅ | 1,1-Dimethyl-2-propynyl |
| 3-(1-Methylethyl)-isoxazol-5-yl | CH₂—CH=N—N—C₆H₅ | 1,1-Dimethyl-2-propynyl |
| 5-Methyl-isoxazol-3-yl | CH₂—CH=N—N—C₆H₅ | 1,1-Dimethyl-2-propynyl |

-continued

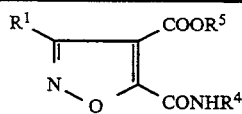

I

| R$^1$ | R$^5$ | R$^4$ |
|---|---|---|
| Phenyl | CH$_2$—CH=N—N—C$_6$H$_5$ | 1,1-Dimethyl-2-propynyl |
| 4-Fluorophenyl | CH$_2$—CH=N—N—C$_6$H$_5$ | 1,1-Dimethyl-2-propynyl |
| 4-Chlorophenyl | CH$_2$—CH=N—N—C$_6$H$_5$ | 1,1-Dimethyl-2-propynyl |
| 2,4-Dichlorophenyl | CH$_2$—CH=N—N—C$_6$H$_5$ | 1,1-Dimethyl-2-propynyl |
| H | CH$_2$—CH=N—N—C$_6$H$_5$ | Cyclopropyl |
| Methyl | CH$_2$—CH=N—N—C$_6$H$_5$ | Cyclopropyl |
| Ethyl | CH$_2$—CH=N—N—C$_6$H$_5$ | Cyclopropyl |
| Propyl | CH$_2$—CH=N—N—C$_6$H$_5$ | Cyclopropyl |
| 1-Methylethyl | CH$_2$—CH=N—N—C$_6$H$_5$ | Cyclopropyl |
| 1-Methylpropyl | CH$_2$—CH=N—N—C$_6$H$_5$ | Cyclopropyl |
| 1,1-Dimethylethyl | CH$_2$—CH=N—N—C$_6$H$_5$ | Cyclopropyl |
| Cyclopropyl | CH$_2$—CH=N—N—C$_6$H$_5$ | Cyclopropyl |
| Cyclopentyl | CH$_2$—CH=N—N—C$_6$H$_5$ | Cyclopropyl |
| Cyclohexyl | CH$_2$—CH=N—N—C$_6$H$_5$ | Cyclopropyl |
| 1-Methylcyclopropyl | CH$_2$—CH=N—N—C$_6$H$_5$ | Cyclopropyl |
| Cyclopropylmethyl | CH$_2$—CH=N—N—C$_6$H$_5$ | Cyclopropyl |
| 1-Cyclopropylethyl | CH$_2$—CH=N—N—C$_6$H$_5$ | Cyclopropyl |
| Chloromethyl | CH$_2$—CH=N—N—C$_6$H$_5$ | Cyclopropyl |
| 1-Chloroethyl | CH$_2$—CH=N—N—C$_6$H$_5$ | Cyclopropyl |
| Methoxymethyl | CH$_2$—CH=N—N—C$_6$H$_5$ | Cyclopropyl |
| 1-Methylmethoxymethyl | CH$_2$—CH=N—N—C$_6$H$_5$ | Cyclopropyl |
| Ethenyl | CH$_2$—CH=N—N—C$_6$H$_5$ | Cyclopropyl |
| 1-Methylethenyl | CH$_2$—CH=N—N—C$_6$H$_5$ | Cyclopropyl |
| 2-Propenyl | CH$_2$—CH=N—N—C$_6$H$_5$ | Cyclopropyl |
| Methoxy | CH$_2$—CH=N—N—C$_6$H$_5$ | Cyclopropyl |
| Ethoxy | CH$_2$—CH=N—N—C$_6$H$_5$ | Cyclopropyl |
| 1,1-Dimethylethoxy | CH$_2$—CH=N—N—C$_6$H$_5$ | Cyclopropyl |
| Furanyl | CH$_2$—CH=N—N—C$_6$H$_5$ | Cyclopropyl |
| Thienyl | CH$_2$—CH=N—N—C$_6$H$_5$ | Cyclopropyl |
| 3-Methyl-isoxazol-5-yl | CH$_2$—CH=N—N—C$_6$H$_5$ | Cyclopropyl |
| 3-Ethyl-isoxazol-5-yl | CH$_2$—CH=N—N—C$_6$H$_5$ | Cyclopropyl |
| 3-(1-Methylethyl)-isoxazol-5-yl | CH$_2$—CH=N—N—C$_6$H$_5$ | Cyclopropyl |
| 5-Methyl-isoxazol-3-yl | CH$_2$—CH=N—N—C$_6$H$_5$ | Cyclopropyl |
| Phenyl | CH$_2$—CH=N—N—C$_6$H$_5$ | Cyclopropyl |
| 4-Fluorophenyl | CH$_2$—CH=N—N—C$_6$H$_5$ | Cyclopropyl |
| 4-Chlorophenyl | CH$_2$—CH=N—N—C$_6$H$_5$ | Cyclopropyl |
| 2,4-Dichlorophenyl | CH$_2$—CH=N—N—C$_6$H$_5$ | Cyclopropyl |
| H | CH$_2$—CH=N—N—C$_6$H$_3$(NO$_2$)$_2$ (2,4-dinitrophenyl) | 1,1-Dimethylethyl |
| Methyl | CH$_2$—CH=N—N—C$_6$H$_3$(NO$_2$)$_2$ (2,4-dinitrophenyl) | 1,1-Dimethylethyl |
| Ethyl | CH$_2$—CH=N—N—C$_6$H$_3$(NO$_2$)$_2$ (2,4-dinitrophenyl) | 1,1-Dimethylethyl |
| Propyl | CH$_2$—CH=N—N—C$_6$H$_3$(NO$_2$)$_2$ (2,4-dinitrophenyl) | 1,1-Dimethylethyl |
| 1-Methylethyl | CH$_2$—CH=N—N—C$_6$H$_3$(NO$_2$)$_2$ (2,4-dinitrophenyl) | 1,1-Dimethylethyl |
| 1-Methylpropyl | CH$_2$—CH=N—N—C$_6$H$_3$(NO$_2$)$_2$ (2,4-dinitrophenyl) | 1,1-Dimethylethyl |
| 1,1-Dimethylethyl | CH$_2$—CH=N—N—C$_6$H$_3$(NO$_2$)$_2$ (2,4-dinitrophenyl) | 1,1-Dimethylethyl |

-continued $$\underset{N\diagdown_O}{\overset{R^1}{\diagup}}\hspace{-4pt}\begin{array}{c}COOR^5\\CONHR^4\end{array}\qquad I$$

| R¹ | R⁵ | R⁴ |
|---|---|---|
| Cyclopropyl | CH₂—CH=N—N—C₆H₃(NO₂)₂ | 1,1-Dimethylethyl |
| Cyclopentyl | CH₂—CH=N—N—C₆H₃(NO₂)₂ | 1,1-Dimethylethyl |
| Cyclohexyl | CH₂—CH=N—N—C₆H₃(NO₂)₂ | 1,1-Dimethylethyl |
| 1-Methylcyclopropyl | CH₂—CH=N—N—C₆H₃(NO₂)₂ | 1,1-Dimethylethyl |
| Cyclopropylmethyl | CH₂—CH=N—N—C₆H₃(NO₂)₂ | 1,1-Dimethylethyl |
| 1-Cyclopropylethyl | CH₂—CH=N—N—C₆H₃(NO₂)₂ | 1,1-Dimethylethyl |
| Chloromethyl | CH₂—CH=N—N—C₆H₃(NO₂)₂ | 1,1-Dimethylethyl |
| 1-Chloroethyl | CH₂—CH=N—N—C₆H₃(NO₂)₂ | 1,1-Dimethylethyl |
| Methoxymethyl | CH₂—CH=N—N—C₆H₃(NO₂)₂ | 1,1-Dimethylethyl |
| 1-Methylmethoxymethyl | CH₂—CH=N—N—C₆H₃(NO₂)₂ | 1,1-Dimethylethyl |
| Ethenyl | CH₂—CH=N—N—C₆H₃(NO₂)₂ | 1,1-Dimethylethyl |
| 1-Methylethenyl | CH₂—CH=N—N—C₆H₃(NO₂)₂ | 1,1-Dimethylethyl |
| 2-Propenyl | CH₂—CH=N—N—C₆H₃(NO₂)₂ | 1,1-Dimethylethyl |
| Methoxy | CH₂—CH=N—N—C₆H₃(NO₂)₂ | 1,1-Dimethylethyl |

-continued

| | | I |
|---|---|---|

Structure I:

$$\begin{array}{c} R^1 \quad COOR^5 \\ \diagdown \quad \diagup \\ \| \quad \| \\ N \quad CONHR^4 \\ \diagdown O \diagup \end{array}$$

| R¹ | R⁵ | R⁴ |
|---|---|---|
| Ethoxy | CH₂—CH=N—N—(2-NO₂, 4-NO₂-phenyl) | 1,1-Dimethylethyl |
| 1,1-Dimethylethoxy | CH₂—CH=N—N—(2-NO₂, 4-NO₂-phenyl) | 1,1-Dimethylethyl |
| Furanyl | CH₂—CH=N—N—(2-NO₂, 4-NO₂-phenyl) | 1,1-Dimethylethyl |
| Thienyl | CH₂—CH=N—N—(2-NO₂, 4-NO₂-phenyl) | 1,1-Dimethylethyl |
| 3-Methyl-isoxazol-5-yl | CH₂—CH=N—N—(2-NO₂, 4-NO₂-phenyl) | 1,1-Dimethylethyl |
| 3-Ethyl-isoxazol-5-yl | CH₂—CH=N—N—(2-NO₂, 4-NO₂-phenyl) | 1,1-Dimethylethyl |
| 3-(1-Methylethyl)-isoxazol-5-yl | CH₂—CH=N—N—(2-NO₂, 4-NO₂-phenyl) | 1,1-Dimethylethyl |
| 5-Methyl-isoxazol-3-yl | CH₂—CH=N—N—(2-NO₂, 4-NO₂-phenyl) | 1,1-Dimethylethyl |
| Phenyl | CH₂—CH=N—N—(2-NO₂, 4-NO₂-phenyl) | 1,1-Dimethylethyl |
| 4-Fluorophenyl | CH₂—CH=N—N—(2-NO₂, 4-NO₂-phenyl) | 1,1-Dimethylethyl |
| 4-Chlorophenyl | CH₂—CH=N—N—(2-NO₂, 4-NO₂-phenyl) | 1,1-Dimethylethyl |
| 2,4-Dichlorophenyl | CH₂—CH=N—N—(2-NO₂, 4-NO₂-phenyl) | 1,1-Dimethylethyl |
| H | CH₂—CH=N—N—(2-NO₂, 4-NO₂-phenyl) | 1,1-Dimethyl-2-propynyl |
| Methyl | CH₂—CH=N—N—(2-NO₂, 4-NO₂-phenyl) | 1,1-Dimethyl-2-propynyl |

-continued $$\begin{array}{c} R^1 \quad COOR^5 \\ \diagdown \diagup \\ \mid \quad \mid \\ N \quad CONHR^4 \\ \diagdown O \diagup \end{array} \qquad I$$

| R¹ | R⁵ | R⁴ |
|---|---|---|
| Ethyl | CH₂—CH=N—N-(2-NO₂,4-NO₂-phenyl) | 1,1-Dimethyl-2-propynyl |
| Propyl | CH₂—CH=N—N-(2-NO₂,4-NO₂-phenyl) | 1,1-Dimethyl-2-propynyl |
| 1-Methylethyl | CH₂—CH=N—N-(2-NO₂,4-NO₂-phenyl) | 1,1-Dimethyl-2-propynyl |
| 1-Methylpropyl | CH₂—CH=N—N-(2-NO₂,4-NO₂-phenyl) | 1,1-Dimethyl-2-propynyl |
| 1,1-Dimethylethyl | CH₂—CH=N—N-(2-NO₂,4-NO₂-phenyl) | 1,1-Dimethyl-2-propynyl |
| Cyclopropyl | CH₂—CH=N—N-(2-NO₂,4-NO₂-phenyl) | 1,1-Dimethyl-2-propynyl |
| Cyclopentyl | CH₂—CH=N—N-(2-NO₂,4-NO₂-phenyl) | 1,1-Dimethyl-2-propynyl |
| Cyclohexyl | CH₂—CH=N—N-(2-NO₂,4-NO₂-phenyl) | 1,1-Dimethyl-2-propynyl |
| 1-Methylcyclopropyl | CH₂—CH=N—N-(2-NO₂,4-NO₂-phenyl) | 1,1-Dimethyl-2-propynyl |
| Cyclopropylmethyl | CH₂—CH=N—N-(2-NO₂,4-NO₂-phenyl) | 1,1-Dimethyl-2-propynyl |
| 1-Cyclopropylethyl | CH₂—CH=N—N-(2-NO₂,4-NO₂-phenyl) | 1,1-Dimethyl-2-propynyl |
| Chloromethyl | CH₂—CH=N—N-(2-NO₂,4-NO₂-phenyl) | 1,1-Dimethyl-2-propynyl |
| 1-Chloroethyl | CH₂—CH=N—N-(2-NO₂,4-NO₂-phenyl) | 1,1-Dimethyl-2-propynyl |
| Methoxymethyl | CH₂—CH=N—N-(2-NO₂,4-NO₂-phenyl) | 1,1-Dimethyl-2-propynyl |

-continued $$\underset{N\diagdown O}{\overset{R^1}{\underset{}{\bigtriangleup}}}\overset{COOR^5}{\underset{CONHR^4}{}}$$  I

| R¹ | R⁵ | R⁴ |
|---|---|---|
| 1-Methylmethoxymethyl | CH₂—CH=N—N—C₆H₃(NO₂)₂ | 1,1-Dimethyl-2-propynyl |
| Ethenyl | CH₂—CH=N—N—C₆H₃(NO₂)₂ | 1,1-Dimethyl-2-propynyl |
| 1-Methylethenyl | CH₂—CH=N—N—C₆H₃(NO₂)₂ | 1,1-Dimethyl-2-propynyl |
| 2-Propenyl | CH₂—CH=N—N—C₆H₃(NO₂)₂ | 1,1-Dimethyl-2-propynyl |
| Methoxy | CH₂—CH=N—N—C₆H₃(NO₂)₂ | 1,1-Dimethyl-2-propynyl |
| Ethoxy | CH₂—CH=N—N—C₆H₃(NO₂)₂ | 1,1-Dimethyl-2-propynyl |
| 1,1-Dimethylethoxy | CH₂—CH=N—N—C₆H₃(NO₂)₂ | 1,1-Dimethyl-2-propynyl |
| Furanyl | CH₂—CH=N—N—C₆H₃(NO₂)₂ | 1,1-Dimethyl-2-propynyl |
| Thienyl | CH₂—CH=N—N—C₆H₃(NO₂)₂ | 1,1-Dimethyl-2-propynyl |
| 3-Methyl-isoxazol-5-yl | CH₂—CH=N—N—C₆H₃(NO₂)₂ | 1,1-Dimethyl-2-propynyl |
| 3-Ethyl-isoxazol-5-yl | CH₂—CH=N—N—C₆H₃(NO₂)₂ | 1,1-Dimethyl-2-propynyl |
| 3-(1-Methylethyl)-isoxazol-5-yl | CH₂—CH=N—N—C₆H₃(NO₂)₂ | 1,1-Dimethyl-2-propynyl |
| 5-Methyl-isoxazol-3-yl | CH₂—CH=N—N—C₆H₃(NO₂)₂ | 1,1-Dimethyl-2-propynyl |
| Phenyl | CH₂—CH=N—N—C₆H₃(NO₂)₂ | 1,1-Dimethyl-2-propynyl |

-continued $$\begin{array}{c} R^1 \diagdown\!\!\!\diagup COOR^5 \\ N\!\!\diagdown_O\diagup\!\!\!\diagdown CONHR^4 \end{array} \quad I$$

| $R^1$ | $R^5$ | $R^4$ |
|---|---|---|
| 4-Fluorophenyl | $CH_2-CH=N-N$–(2-$NO_2$,4-$NO_2$-phenyl) | 1,1-Dimethyl-2-propynyl |
| 4-Chlorophenyl | $CH_2-CH=N-N$–(2-$NO_2$,4-$NO_2$-phenyl) | 1,1-Dimethyl-2-propynyl |
| 2,4-Dichlorophenyl | $CH_2-CH=N-N$–(2-$NO_2$,4-$NO_2$-phenyl) | 1,1-Dimethyl-2-propynyl |
| H | $CH_2-CH=N-N$–(2-$NO_2$,4-$NO_2$-phenyl) | Cyclopropyl |
| Methyl | $CH_2-CH=N-N$–(2-$NO_2$,4-$NO_2$-phenyl) | Cyclopropyl |
| Ethyl | $CH_2-CH=N-N$–(2-$NO_2$,4-$NO_2$-phenyl) | Cyclopropyl |
| Propyl | $CH_2-CH=N-N$–(2-$NO_2$,4-$NO_2$-phenyl) | Cyclopropyl |
| 1-Methylethyl | $CH_2-CH=N-N$–(2-$NO_2$,4-$NO_2$-phenyl) | Cyclopropyl |
| 1-Methylpropyl | $CH_2-CH=N-N$–(2-$NO_2$,4-$NO_2$-phenyl) | Cyclopropyl |
| 1,1-Dimethylethyl | $CH_2-CH=N-N$–(2-$NO_2$,4-$NO_2$-phenyl) | Cyclopropyl |
| Cyclopropyl | $CH_2-CH=N-N$–(2-$NO_2$,4-$NO_2$-phenyl) | Cyclopropyl |
| Cyclopentyl | $CH_2-CH=N-N$–(2-$NO_2$,4-$NO_2$-phenyl) | Cyclopropyl |
| Cyclohexyl | $CH_2-CH=N-N$–(2-$NO_2$,4-$NO_2$-phenyl) | Cyclopropyl |
| 1-Methylcyclopropyl | $CH_2-CH=N-N$–(2-$NO_2$,4-$NO_2$-phenyl) | Cyclopropyl |

-continued $$\underset{N\diagdown O}{\overset{R^1}{\underset{}{\bigg|}}}\overset{COOR^5}{\underset{CONHR^4}{\bigg|}}\quad I$$

| R¹ | R⁵ | R⁴ |
|---|---|---|
| Cyclopropylmethyl | CH₂—CH=N—N—(2-NO₂,4-NO₂-C₆H₃) | Cyclopropyl |
| 1-Cyclopropylethyl | CH₂—CH=N—N—(2-NO₂,4-NO₂-C₆H₃) | Cyclopropyl |
| Chloromethyl | CH₂—CH=N—N—(2-NO₂,4-NO₂-C₆H₃) | Cyclopropyl |
| 1-Chloroethyl | CH₂—CH=N—N—(2-NO₂,4-NO₂-C₆H₃) | Cyclopropyl |
| Methoxymethyl | CH₂—CH=N—N—(2-NO₂,4-NO₂-C₆H₃) | Cyclopropyl |
| 1-Methylmethoxymethyl | CH₂—CH=N—N—(2-NO₂,4-NO₂-C₆H₃) | Cyclopropyl |
| Ethenyl | CH₂—CH=N—N—(2-NO₂,4-NO₂-C₆H₃) | Cyclopropyl |
| 1-Methylethenyl | CH₂—CH=N—N—(2-NO₂,4-NO₂-C₆H₃) | Cyclopropyl |
| 2-Propenyl | CH₂—CH=N—N—(2-NO₂,4-NO₂-C₆H₃) | Cyclopropyl |
| Methoxy | CH₂—CH=N—N—(2-NO₂,4-NO₂-C₆H₃) | Cyclopropyl |
| Ethoxy | CH₂—CH=N—N—(2-NO₂,4-NO₂-C₆H₃) | Cyclopropyl |
| 1,1-Dimethylethoxy | CH₂—CH=N—N—(2-NO₂,4-NO₂-C₆H₃) | Cyclopropyl |
| Furanyl | CH₂—CH=N—N—(2-NO₂,4-NO₂-C₆H₃) | Cyclopropyl |
| Thienyl | CH₂—CH=N—N—(2-NO₂,4-NO₂-C₆H₃) | Cyclopropyl |

-continued $$\text{I}$$

Structure I: isoxazoline ring with $R^1$ substituent at C, $COOR^5$ and $CONHR^4$ groups.

| $R^1$ | $R^5$ | $R^4$ |
|---|---|---|
| 3-Methyl-isoxazol-5-yl | $CH_2-CH=N-N-$(2-$NO_2$,4-$NO_2$-phenyl) | Cyclopropyl |
| 3-Ethyl-isoxazol-5-yl | $CH_2-CH=N-N-$(2-$NO_2$,4-$NO_2$-phenyl) | Cyclopropyl |
| 3-(1-Methylethyl)-isoxazol-5-yl | $CH_2-CH=N-N-$(2-$NO_2$,4-$NO_2$-phenyl) | Cyclopropyl |
| 5-Methyl-isoxazol-3-yl | $CH_2-CH=N-N-$(2-$NO_2$,4-$NO_2$-phenyl) | Cyclopropyl |
| Phenyl | $CH_2-CH=N-N-$(2-$NO_2$,4-$NO_2$-phenyl) | Cyclopropyl |
| 4-Fluorophenyl | $CH_2-CH=N-N-$(2-$NO_2$,4-$NO_2$-phenyl) | Cyclopropyl |
| 4-Chlorophenyl | $CH_2-CH=N-N-$(2-$NO_2$,4-$NO_2$-phenyl) | Cyclopropyl |
| 2,4-Dichlorophenyl | $CH_2-CH=N-N-$(2-$NO_2$,4-$NO_2$-phenyl) | Cyclopropyl |

The compounds Z, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as Kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, i-sophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NHR spectrum).

The compounds I according to the invention may be formulated as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.008 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.012 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.001 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.001 is intimately mixed with 97 parts by weight of particulate kaolin. A dust is obtained containing 3% by weight of the active ingredient.

VII. 30 parts by weight of compound no. 1.001 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.001 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 1, preferably 0.01 to 0.5, kg of active ingredient per hectare. In view of the numerous application methods possible, the compounds according to the invention may be used in a large number of crops. Those which follow are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Camellia sinensis* | tea plants |
| *Carthamus tinctorius* | safflower |
| *Carya illinoinensis* | pecan trees |
| *Citrus limon* | lemons |
| *Citrus sinensis* | oranges |
| *Coffea arabica* (*Coffea canephora, Coffea liberica*) | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |

-continued

| Botanical name | Common name |
|---|---|
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To increase the spectrum of action and to achieve synergistic effects, the isoxazole- and isothiazole-5-carboxamides I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamares, halocarboxylic acids, triazines, amides, ureas, diphenyl ethers, triazinones, uracils, benzofuran derivatives, cyclohexane-1,3-dione derivatives, quinolinecarboxylic acids, sulfonylureas, (hetero)-aryloxyphenoxypropionic acids and salts, esters, amides thereof, etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

MANUFACTURING EXAMPLES

1. 2-Ethoxyiminoethyl 5-tert-butylaminocarbonyl-3-methylisoxazole-4-carboxylate

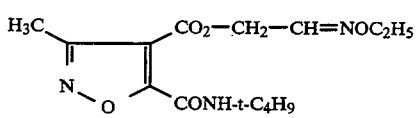

At room temperature 110 g (0.796 mol) of potassium carbonate was added to a solution of 180.0 g (0.796 mot) of 5-tert.-butylaminocarbonyt-3-methyl-isoxazole-4-carboxylic acid in 1 liter of dimethyl sulfoxide; the whole was stirred for 1 hour. 96.8 g (0.796 mol) of 2-ethoxyiminoethyl chloride in 300 mi of dimethyl sulfoxide was then dripped in and the whole was then heated for 16 hours at 50° C. After the mixture had been allowed to cool, ice was added, extraction was carried out with ethyl acetate, the combined organic phases were washed with water and dried, and the solvent was removed under reduced pressure. There was obtained 222.9 g (90%) of 2-ethoxymtnoethyl 5-tert-butylaminocarbonyl-3-methylisoxazole-4-carboxylate (Example No. 1.001).

$^1$H-NMR (CDCl$_3$, 250 MHz) δ=main isomer: 1.28 (t; 3H), 1.47 is; 9H), 2.50 (s; 3H), 4.18 (q; 2H), 4.92 (d; 2H), 7.54 (t; 1H), 9.16 (bs; 1H, NH); secondary isomer: 1.29 (t; 3H), 1.47 (s; 9H), 2.52 (s; 3H), 4.17 (q; 2H), 5.14 (d; 2H), 6.88 (t; 1H), 9.12 (bs; 1H, NH).

2-Methoxyimino-1-methylethyl 5-tert.-butylaminocarbonyl-3-methylisoxazole-4-carboxylate

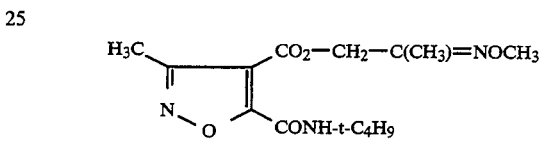

At room temperature, 6.8 g (67.3 mmol) of 4-methylmorpholine and 2.2 g (18 mmol) of -dimethylaminopyridine were dripped into a solution of 4.1 g (18.1 mmol) of 5-tert.-butylaminocarbonyl-3-methylisoxazote-4-carboxylic acid and 2.4 g (23.3 mmol) of 2-methoxyimino-1-methylethyl alcohol in 250 ml of ethyl acetate; after the mixture had been stirred for 5 minutes 15.9 g (25 mmol) of a 50% strength solution of propanephosphonic anhydride in ethyl acetate was added. The solution was heated for 8 hours at 60° C. and evaporated down; the residue was taken up in 250 ml of dichloroethane and extracted twice with saturated sodium bicarbonate solution and once with 5% strength citric acid solution, once with saturated sodium carbonate solution and once with sodium chloride solution. Drying over magnesium sulfate was followed by removal of the solvent under reduced pressure. There was obtained 3.9 g (69%) of 2-methoxyimino-1-methylethyl 5-tert.-butylaminocarbonyl-3-methyl-isoxazole-4-carboxylate (Example No. 1.003).

$^1$H-NMR (COCl3, 250 MHZ) δ=main isomer: 1.48 (s; 9H), 1.96 (s; 3H), 2.47 (s; 3H), 3.92 (s; 3H), 4.86 (s; 2H), 9.12 (bs; 1H, NH).

3-Iodopropargyl 5-tert-butylaminocarbonyl-3-methyl-isoxazole-carboxylate was prepared analogously (Example No. 1.010). Yield: 65%; M.p. =55°–60° C.

1,4-Bis-(5-tert-butylaminocarbonyl-3-isopropyl-4-carbonyloxyisoxazole)-butane

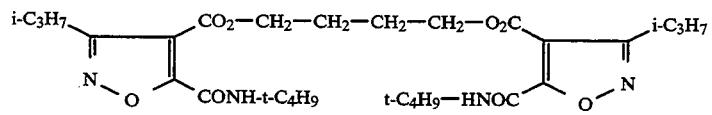

At 10° C., 2 g (19.8 mmol) of triethylamine was dripped into a solution of 5 g (18.3 mmol) of 5-tert-butylaminocarbonyl-3-isopropylisoxazole-4-carboxylic chloride in 200 ml of dichloromethane; over a period of 3 hours, 0.82 g (9.5 mmol) of 1,-butanediol in 100 ml of dichloromethane was dripped in and the whole was stirred for 12 hours at room temperature. The reaction mixture was extracted twice with saturated sodium bicarbonate solution, the organic phase was dried over magnesium sulfate and the solvent was removed under reduced pressure. The residue was purified chromatographically ($SiO_2$; cyclohexane/ethyl acetate 3:1). There was obtained 2.5 g (47%) of 1,4-bis-(5-tert-butylaminocarbonyl-3-isopropyl-4-carbonyloxyisoxazote)-butane of m.p. 117°–120° C. (Example No. 2.002).

The manufacture of the isoxazolecarboxylic acids used as starting materials is described in detail in DE-A 38 12 225.1.

TABLE 1

$$R^1 \diagdown \diagup CO_2-R^5$$
$$\diagup \diagdown$$
$$N\diagdown_O \diagup CONHR^4$$

| No. | R¹ | R² | R⁴ | mp [°C.]/¹H-NMR (250 MHz; CDCl₃ or DMSO, δ in ppm) |
|---|---|---|---|---|
| 1.001 | Methyl | CH₂CH=NOC₂H₅ | tert.-Butyl | Main isomer: 1.28 (t; 3H), 1.47 (s; 9H), 2.50 (s; 3H), 4.18 (q; 2H), 4.92 (d; 2H), 7.54 (t; 1H), 9.16 (bs; 1H, NH) Secondary isomer: 1.29 (t; 3H), 1.47 (s; 9H), 2.52 (s; 3H), 4.17 (q;2H), 5.14 (d; 2H), 6.88 (t; 1H), 9.12 (bs; 1H, NH) |
| 1.002 | Methyl | (CH₂)₃CH=NOCH₃ | tert.-Butyl | Main isomer: 1.46 (s; 9H), 1.90 to 2.50 (m; 4H), 2.50 (s; 3H), 3.80 (s; 3H), 4.40 (q; 2H), 7.41 (t; 1H), 9.34 (bs; 1H, NH) |
| 1.003 | Methyl | CH₂C(CH₃)=NOCH₃ | tert.-Butyl | Main isomer: 1.48 (s; 9H), 1.96(s; 3H), 2.47 (s; 3H), 3.92 (s; 3H), 4.86 (s; 2H) 9.12 (bs; 1H, NH) |
| 1.004 | Methyl | CH₂—CH=NOCH₃ | tert.-Butyl | Main isomer: 1.48 (s; 9H), 2.48 (s; 3H), 3.92 (s; 3H), 4.92 (d; 2H), 7.54 (t; 1H) 9.08 (bs; 1H, NH) Secondary isomer: 1.48 (s; 9H), 2.50 (s; 3H), 3.96 (s; 3H), 5.14 (d; 2H), 6.85 (t; 1H) 9.04 (bs; 1H, NH) |
| 1.005 | Ethyl | CH₂CH=NOC₂H₅ | tert.-Butyl | Main isomer: 1.29 (t; 3H), 1.47 (s; 9H), 2.92 (q; 2H), 4.18 (q; 2H), 4.92 (d; 2H) 7.56 (t; 1H), 8.98 (bs; 1H; NH) |
| 1.006 | Ethyl | (CH₂)₃CH=NOCH₃ | tert.-Butyl | Main isomer: 1.32 (t; 3H), 1.48 (g; 9H) 1.80–2.60 (m; 4H), 2.92 (q; 2H), 3.80 (s; 3H), 4.40 (q; 2H), 7.41 (t; 1H), 9.20 (bs; 1H; NH) |
| 1.007 | Ethyl | CH₂C(CH₃)=NOCH₃ | tert.-Butyl | Main isomer: 1.30 (t; 3H), 1.46 (s; 9H), 1.96 (s; 3H), 2.92 (q; 2H), 3.90 (s; 3H) 4.86 (s, 2H), 8.97 (bs; 1H, NH) |
| 1.008 | 1-Methyl-ethyl | CH₂CH=NOC₂H₅ | tert.-Butyl | 58–61 |
| 1.009 | 1-Methyl-ethyl | CH₂C(CH₃)₂CH=NOCH₃ | tert.-Butyl | Main isomer: 1.22 (s; 6H), 1.36 (d; 6H) 1.46 (s; 9H), 3.42 (m; 1H), 3.82 (s; 3H) 4.28 (s; 2H), 7.32 (s; 1H), 8.98 (bs; 1H; NH) |
| 1.010 | 1-Methyl-ethyl | 3-Iodopropargyl | tert.-Butyl | 55–60 |
| 1.011 | Methyl | CH₂—CH=NO—C₂H₅ | C(CH₃)₂—C≡CH | 79–82 |
| 1.012 | Methyl | CH₂—CH=NO—CH₃ | C(CH₃)₂—C≡CH | 99–102 |
| 1.013 | Ethyl | CH₂—CH=NO—CH₃ | C(CH₃)₂—C≡CH | 70–73 |
| 1.014 | Ethyl | CH₂—CH=NO—C₂H₅ | C(CH₃)₂—C≡CH | 49–51 |
| 1.015 | tert.-Butyl | CH₂—CH=NO—C₂H₅ | Cyclopropyl | 0.62–0.93 (m; 4H), 1.37 (s; 9H), 7.56 (t; 1H) |
| 1.016 | Cyclopropyl | CH₂—CH=NO—CH₃ | Cyclopropyl | 93–95 |
| 1.017 | Isobutyl | CH₂—CH=NO—C₂H₅ | Cyclopropyl | 78–80 |
| 1.018 | Methyl | CH₂—CH=NO-tert.-Butyl | tert.-Butyl | 65–67 |
| 1.019 | Methyl | CH₂—CH=NO—CH₂—CH=CH₂ | tert.-Butyl | 1.47 (s; 9H), 2.48 (s; 3H), 7.64 (t; 1H) |
| 1.020 | Methyl | CH₂—CH=NO—CH₂—CH=CH—CH₃ (trans) | tert.-Butyl | 1.48 (s; 9H), 2.48 (s; 3H), 7.55 (t; 1H) |
| 1.021 | tert.-Butyl | CH₂—CH=NO—C₂H₅ | tert.-Butyl | 1.37 (s; 9H), 1.47 (s; 9H), 7.52 (t; 1H) |
| 1.022 | Cyclopropyl | CH₂—CH=NO—CH₃ | Cyclopentyl | 92–94 |
| 1.023 | 1-Methoxyethyl | CH₂—CH=NO—C₂H₅ | tert.-Butyl | 1.48 (s; 9H), 3.33 (s; 3H), 7.52 (t; 1H), 8.24 (bs; 1H, NH) |
| 1.024 | Ethyl | CH₂—CH=NO—C₂H₅ | C(CH₃)₂CH=CH₂ | 1.55 (s; 6H), 6.12 (m; 1H), 7.54 (t; 1H), 9.10 (bs; 1H, NH) |
| 1.025 | sec.-Butyl | CH₂—CH=NOCH₂—CH=CH₂ | isopropyl | 0.80 (t; 3H), 1.30 (d; 3H), 7.50 (t; 1H) |
| 1.026 | sec.-Butyl | CH₂—CH=NOCH₂—CH=CH₂ | isopropyl | 50–51 |
| 1.027 | sec.-Butyl | CH₂—CH=NOC₂H₅ | Isopropyl | 72–73 |
| 1.028 | sec.-Butyl | CH₂—CH=NOCH₃ | Isopropyl | 87–89 |

TABLE 1-continued $$R^1 \diagdown \diagup CO_2-R^5$$
$$\phantom{R^1} \diagup \diagdown CONHR^4$$
$$N-O$$

| No. | $R^1$ | $R^2$ | $R^4$ | mp [°C.]/$^1$H-NMR (250 MHz; CDCl$_3$ or DMSO, δ in ppm) |
|---|---|---|---|---|
| 1.029 | sec.-Butyl | CH$_2$—CH=NOCH$_3$ | tert.-Butyl | 0.80 (t; 3H), 1.25 (d; 3H), 7.55 (t; 3H) |
| 1.030 | sec.-Butyl | CH$_2$—CH=NOCH$_2$—CH=CH—CH$_3$ | tert.-Butyl | 0.85 (t; 3H), 1.25 (d; 3H), 7.5 (t; 3H) |
| 1.031 | sec.-Butyl | CH$_2$—CH=NO-tert.-Butyl | tert.-Butyl | 1.20 (s; 9H), 7.45 (t; 1H) |
| 1.032 | sec.-Butyl | CH$_2$—CH=NOC$_2$H$_5$ | tert.-Butyl | 0.85 (t; 3H), 1.30 (d; 3H), 7.50 (t; 1H) |
| 1.033 | Ethyl | CH$_2$—CH=NOCH$_3$ | tert.-Butyl | 1.35 (s; 9H), 2.9 (q; 2H), 7.55 (t; 1H) |
| 1.034 | Ethyl | CH$_2$—CH=NO—CH$_2$—CH=CH$_2$ | tert.-Butyl | 100–101 |
| 1.035 | Ethyl | CH$_2$—CH=NO-tert.-Butyl | tert.-Butyl | 2.85 (q; 2H), 7.60 (t; 1H) |
| 1.036 | Ethyl | CH$_2$—CH=NO-n-Propyl | tert.-Butyl | 1.20 (t; 3H), 2.90 (q; 2H), 7.55 (t; 1H) |
| 1.037 | Ethyl | CH$_2$—CH=NOCH$_2$—CH=CH—Cl | tert.-Butyl | 3.85 (q; 2H), 7.60 (t; 1H) |
| 1.038 | Ethyl | CH$_2$—CH=NO-isopropyl | tert.-Butyl | 4.25 (sept., 1H), 7.45 (t; 1H) |
| 1.039 | Isopropyl | CH$_2$—CH=NOCH$_3$ | tert.-Butyl | 53–54 |
| 1.040 | Isopropyl | CH$_2$—CH=NO-tert.-Butyl | tert.-Butyl | 104–105 |
| 1.041 | Isopropyl | CH$_2$—CH=NOCH$_3$ | C(CH$_3$)$_2$—C≡CH | 1.40 (s; 3H), 3.30 (s; 3H), 7.50 (t; 1H) |
| 1.042 | Isopropyl | CH$_2$—CH=NO-isopropyl | C(CH$_3$)$_2$—C$_2$≡CH | 4.80 (d; 1H), 7.50 (t; 1H) |
| 1.043 | Ethyl | CH$_2$—CH=NOC$_2$H$_5$ | sec.-Butyl | 65–67 |
| 1.044 | Ethyl | CH$_2$—CH=NOC$_2$H$_5$ | C(CH$_3$)$_2$—C$_2$H$_5$ | 1.44 (s; 6H), 7.56 (t; 1H), 8.85 (bs; 1H, NH) |
| 1.045 | Ethyl | CH$_2$—CH=NOC$_2$H$_5$ | Cyclopentyl | 117–119 |
| 1.046 | Ethyl | CH$_2$—CH=NOC$_2$H$_5$ | Ethyl | 82–85 |
| 1.047 | Ethyl | CH$_2$—CH=NOC$_2$H$_5$ | Cyclohexyl | 129–131 |
| 1.048 | Ethyl | CH$_2$—CH=NOC$_2$H$_5$ | C(CH$_3$)$_2$—CH(CH$_3$)$_2$ | 0.92 (d; 6H), 2.37 (m; 1H), 7.55 (t; 1H), 8.88 (bs;1H,NH) |
| 1.049 | Ethyl | CH$_2$—CH=NOCH$_3$ | —CH$_2$—C(CH$_3$)$_3$ | 1.00 (s; 9H), 3.29 (d; 2H), 7.56 (t; 1H), 9.33 (bs; 1H, NH) |
| 1.050 | Ethyl | CH$_2$—CH=NOC$_2$H$_5$ | Benzyl | 88–91 |
| 1.051 | 1-Chloroethyl | CH$_2$—CH=NOC$_2$H$_5$ | C(CH$_3$)$_2$—CH=CH$_2$ | 1.56 (s; 6H), 6.10 (m; )H), 7.56 (t; 1H), 8.86 (bs; 1H, NH) |
| 1.052 | 1-Chloroethyl | CH$_2$—CH=NOC$_2$H$_5$ | 1-Cyclopropylethyl | 54–56 |
| 1.053 | Ethyl | CH$_2$—CH=NOC$_2$H$_5$ | 1-Phenylethyl | 84–86 |
| 1.054 | Isopropyl | CH$_2$—CH=NOCH$_2$—CH=CH—Cl | C(CH$_3$)$_2$C≡CH | 1.25 (d; 6H), 1.55 (s; 6H), 7.55 (m; 1H) |
| 1.055 | Ethyl | CH$_2$—CH=NOCH$_3$ | C(CH$_3$)$_2$C≡CH | 1.35 (s; 6H), 4.75 (d; 1H) |
| 1.056 | n-Propyl | CH$_2$—CH=NO-tert.-Butyl | C(CH$_3$)$_2$C≡CH | 0.90 (t; 3H), 1.15 (s; 9H), 7.45 (t; 1H) |
| 1.057 | n-Propyl | CH$_2$—CH=NOCH$_3$ | Isopropyl | 67–68 |
| 1.058 | n-Propyl | CH$_2$—CH=NOC$_2$H$_5$ | Isopropyl | 66–67 |
| 1.059 | n-Propyl | CH$_2$—CH=NOCH$_2$—CH=CH-Phenyl | Isopropyl | 1.15 (d; 6H), 4.80 (d; 1H), 7.2-7.4 (m; 5H) |
| 1.060 | n-Propyl | CH$_2$—CH=NOCH$_3$ | Cyclopropyl | 68–69 |
| 1.061 | n-Propyl | CH$_2$—CH=NO-isopropyl | Cyclopropyl | 96–98 |
| 1.062 | n-Propyl | CH$_2$—CH=NOCH$_3$ | 1-Cyclopropylethyl | 62–65 |
| 1.063 | n-Propyl | CH$_2$—CH=NOC$_2$H$_5$ | 1-Cyclopropylethyl | 62–63 |
| 1.064 | n-Propyl | CH$_2$—CH=N-OCH$_2$—CH=CH$_2$ | 1-Cyclopropylethyl | 62–63 |
| 1.065 | sec.-Butyl | CH$_2$—CH=NOCH$_3$ | Cyclopropyl | 58–63 |
| 1.066 | sec.-Butyl | CH$_2$—CH=N-OCH$_2$—CH=CH—Cl | Cyclopropyl | |
| 1.067 | Ethyl | —N=C$<^{OC_2H_5}_{C_2H_5}$ | tert.-Butyl | 1.48 (s; 9H), 4.43 (q; 2H), 9.35 (bs,)H,NH) |
| 1.068 | Phenyl | CH$_2$—CH=N—O—C$_2$H$_5$ | tert.-Butyl | 7.23 (t; 1H), 8.18 (bs; 1H, NH) |
| 1.069 | n-Propyl | CH$_2$—CH=N—OCH$_3$ | tert.-Butyl | 0.95 (t; 3H), 1.15 (s; 9H), 7.50 (t; 1H) |

TABLE 2

Structure: R¹-C(=N-O-)=C(CO₂-W-Z)(CONH-tert.-Butyl)

| No. | R¹ | W | Z | mp [°C.]/¹H-NMR (250 MHZ; CDCl₃, δ in ppm) |
|---|---|---|---|---|
| 2.001 | Methyl | —CH₂—C≡C—CH₂— | —O₂C—C(CH₃)=C(CONHtBu)—O—N (ring) | 117 to 121 |
| 2.002 | 1-Methylethyl | —(CH₂)₄— | —O₂C—C(iC₃H₇)=C(CONHtBu)—O—N (ring) | 117 to 120 |
| 2.003 | 1-Methylethyl | —CH₂—CH=CH—CH₂— (cis) | —O₂C—C(iC₃H₇)=C(CONHtBu)—O—N (ring) | 1.34 (d; 12H), 1.48 (s; 18H), 3.40 (m; 2H), 5.05 (d; 4H), 5.98 (t; 2H), 8.60 (bs; 2H, NH) |
| 2.004 | 1-Methylethyl | —CH₂—C≡C—CH₂— | —O₂C—C(iC₃H₇)=C(CONHtBu)—O—N (ring) | 1.36 (d; 12H), 1.48 (s; 18H), 3.40 (m; 2H), 5.05 (s; 4H), 8.34 (bs; 2H, NH) |

USE EXAMPLES

The herbicidal action of compounds I according to the invention is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. The vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. Application rates for postemergence treatment were 1 and 0.5 kg/ha.

The pots were set up in the greenhouse, heat-loving species at 20 to 35° C., and species from moderate climates at 10 to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plant species used in the greenhouse experiments were Zea mays Amaranthus retroflexus, Cassia tora and Veronica spp.

Example No. 1,001, used postemergence at rates of 1.0 and 0.5 kg/ha, combated unwanted broadleaved plants very well and was tolerated by Indian corn used as an example of a crop.

When compound 1.008 was applied postemergence at rates of 1.0 and 0.5 kg/ha, it had an excellent action on unwanted plants such as Chenopodium album, Polygonum persicaria and Veronica spp., and was excellently tolerated by winter wheat and Indian corn as examples of crops.

Compound 1.0012 is extremely selective in groundnuts and provides effective control of unwanted broadleaved plants such as Amaranthus retroflexus, Chenopodium album and Solanum nigrum.

Compound 1,003 is extremely effective at the abovementioned application rates on Amaranthus retroflexus, Solanum nigrum and Veronica spp., and is well tolerated by Indian corn.

Compared with prior art compound A

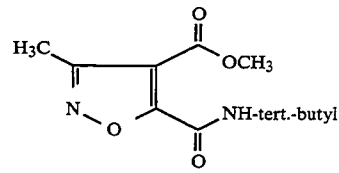

disclosed in DE-A 38 12 225, the herbicidal-action on injurious broadleaved plants is significantly superior, as is clear from a comparison with compound 1.001 according to the invention:

| Test plants | Damage in % | | | |
|---|---|---|---|---|
| | 1.001 | | A | |
| | 1 kg/ha | 0.5 kg/ha | 1 kg/ha | 0.5 kg/ha |
| Zea mays | 20 | 10 | 15 | 10 |
| Amaranthus retroflexus | 90 | 50 | 10 | 0 |
| Cassia tora | 100 | 90 | 70 | 10 |

| | Damage in % | | | |
|---|---|---|---|---|
| | 1.001 | | A | |
| Test plants | 1 kg/ha | 0.5 kg/ha | 1 kg/ha | 0.5 kg/ha |
| Veronica spp. | 100 | 95 | 55 | 40 |

We claim:

1. An isoxazole- or isothiazole-5-carboxamide of the formula I

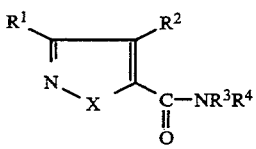

where

X is oxygen or sulfur;

$R^1$ is hydrogen, $C_1$–$C_6$-alkyl which can carry from one to five halogen atoms and/or one or two of the following: $C_1$–$C_3$-alkoxy, $C_1$–$C_3$-haloalkoxy, cyano or phenyl which can be up to trisubstituted by halogen, $C_1$–$C_3$-alkyl, $C_1$–$C_3$-haloalkyl, $C_1$–$C_3$-alkoxy, $C_1$–$C_3$-haloalkoxy, cyano or nitro;

$C_3$–$C_8$-cycloalkyl-substituted $C_1$–$C_6$-alkyl;

$C_3$–$C_8$-cycloalkyl or $C_3$–$C_6$-cycloalkenyl, each of which can be mono- to trisubstituted by $C_1$–$C_4$-alkyl or halogen;

$C_2$–$C_6$-alkenyl whose double bond can be epoxidized, or $C_2$–$C_6$-alkynyl, where both groups can be mono- to trisubstituted by halogen, $C_1$–$C_3$-alkoxy and/or monosubstituted by cyclopropyl or phenyl, where the phenyl can additionally carry up to three of the following substituents: $C_1$–$C_4$-alkyl, $C_1$–$C_4$-haloalkyl, $C_1$–$C_4$-alkoxy, $C_1$–$C_4$-haloalkoxy, halogen, cyano or nitro;

$C_1$–$C_4$-alkoxy;

a 5- or 6-membered heterocyclic radical with one or two hetero atoms selected from oxygen, sulfur and nitrogen, which can carry one or two of the following substituents: $C_1$–$C_3$-alkyl, halogen, $C_1$–$C_3$-alkoxy, carboxyl or $C_1$–$C_3$-alkoxycarbonyl;

phenyl which can carry from one to three of the following: $C_1$–$C_3$-alkyl, $C_1$–$C_3$-haloalkyl, $C_1$–$C_3$-alkoxy, $C_1$–$C_3$-haloalkoxy, $C_1$–$C_3$-alkylthio, $C_1$–$C_3$-haloalkylthio, halogen, nitro and cyano, $R^2$ is $COYR^5$, where Y is oxygen or sulfur $R^5$ is $C_3$–$C_6$-haloalkynyl or $C_1$–$C_4$-alkyl which carries —$CR^{10}$=N—$R^{11}$ where $R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyloxy, each of which can carry up to three halogen atoms and/or one phenyl with, if desired, up to three of the following: halogen, nitro, cyano, $C_1$–$C_3$-alkyl or $C_1$–$C_3$-alkoxy; phenoxy which can carry up to three of the following substituents: halogen, nitro, cyano, $C_1$–$C_3$-alkyl or $C_1$–$C_3$-alkoxy; $C_1$–$C_3$-alkylamino, di($C_1$–$C_6$-alkyl)amino or phenylamino, where the aromatic ring can carry up to three of the following: halogen, nitro, cyano, $C_1$–$C_3$-alkyl or $C_1$–$C_3$-alkoxy;

$R^3$ is hydrogen;

$C_1$–$C_6$-alkyl which can carry from one to three of the following substituents: hydroxyl, halogen, $C_1$–$C_4$-alkoxy, $C_1$–$C_4$-alkylthio or di-($C_1$–$C_4$)-alkylamino;

$C_3$–$C_8$-cycloalkyl which can be mono- to trisubstituted by halogen, $C_1$–$C_4$-alkyl and partially or completely halogenated $C_1$–$C_4$-alkyl;

$R^4$ is hydrogen, hydroxyl, $C_1$–$C_4$-alkoxy;

$C_1$–$C_6$-alkyl which can carry from one to three of the following: halogen, cyano, $C_1$–$C_4$-alkoxy, partially or completely halogenated $C_1$–$C_4$-alkoxy, $C_1$–$C_4$-alkylthio, partially or completely halogenated $C_1$–$C_4$-alkylthio, di-$C_1$–$C_4$-alkylamino, $C_3$–$C_8$-cycloalkyl or phenyl, where the phenyl ring in turn can carry one to three of the following: halogen, cyano, nitro, $C_1$–$C_4$-alkyl, partially or completely halogenated $C_1$–$C_4$-alkyl, $C_1$–$C_4$-alkoxy, $C_1$–$C_4$-alkylthio or partially or completely halogenated $C_1$–$C_4$-alkoxy or $C_1$–$C_4$-alkylthio;

$C_3$–$C_8$-cycloalkyl which can carry from one to three of the following: halogen, nitro, cyano, $C_1$–$C_6$-alkyl, partially or completely halogenated $C_1$–$C_6$-alkyl, $C_1$–$C_4$-alkoxy or partially or completely halogenated $C_1$–$C_4$-alkoxy;

$C_3$–$C_6$-alkenyl whose double bond can be epoxidized, or $C_3$–$C_6$-alkynyl, each of which can be mono- to trisubstituted by halogen and/or monosubstituted by phenyl, where the phenyl in turn can carry from one to three of the following: $C_1$–$C_4$-alkyl, $C_1$–$C_4$-halo-alkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;

di-($C_1$–$C_4$)-alkylamino;

a 5- or 6-membered heterocyclic, saturated or aromatic radical with one or two hetero atoms selected from oxygen, sulfur and nitrogen, which can be mono- to trisubstituted by $C_1$–$C_4$-alkyl or halogen;

phenyl which can carry from one to four of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, $C_2$–$C_4$-alkanoyl, $C_2$–$C_4$-haloalkanoyl or $C_1$–$C_4$-alkoxycarbonyl;

naphthyl which can be mono- to trisubstituted by $C_1$–$C_4$-alkyl or halogen;

or $R^3$ and $R^4$ together form a tetra- to heptamethylene chain which can be interrupted by oxygen, sulfur or N-methyl, or —($CH_2)_3$—CO—, with the proviso that $R^5$ is not $C_3$–$C_8$-haloalkynyl when $R^1$ is unsubstituted or substituted $C_2$–$C_6$-alkenyl, whose double bond can be epoxidized, unsubstituted or substituted $C_3$–$C_6$-cycloalkenyl, unsubstituted or substituted $C_2$–$C_6$-alkynyl or $C_3$–$C_8$-cycloalkyl-substituted $C_1$–$C_6$-alkyl;

and the environmentally acceptable salts of the compound I.

2. A carboxamide of the formula I as claimed in claim 1, where X is oxygen and $R^3$ is hydrogen.

3. A carboxamide of the formula I as claimed in claim 1, where X is oxygen, $R^3$ is hydrogen, $R^2$ is $COOR^5$ where $R^5$ is $C_1$–$C_6$-alkyl which is substituted by $CR^{10}$=N—$R^{11}$ where $R^{10}$ is hydrogen or $C_1$–$C_6$-alkyl and $R^{11}$ is $C_1$–$C_6$-alkoxy, $C_3$–$C_6$-alkenyloxy or $C_3$–$C_6$-alkynyl.

4. A herbicidal composition comprising a inert carrier and a herbicidally effective amount of at least one carboxamide of the formula I as claimed in claim 1.

5. A method for controlling unwanted plant growth, which comprises treating the unwanted plants and/or their habitat with a herbicidally effective amount of a carboxamide of the formula I as claimed in claim 1.

* * * * *